United States Patent
El-Araby et al.

(10) Patent No.: US 11,142,493 B1
(45) Date of Patent: Oct. 12, 2021

(54) PHARMACEUTICAL COMPOSITION FOR TREATING CANCER

(71) Applicant: King Abdulaziz University, Jeddah (SA)

(72) Inventors: Moustafa E. El-Araby, Jeddah (SA); Abdelsattar M. Omar, Jeddah (SA); Maan T. Khayat, Jeddah (SA); Dhaval Shah, Jeddah (SA); Martin K. Safo, Jeddah (SA); Azizah M. Malebari, Jeddah (SA); Farid Ahmed, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 17/355,614

(22) Filed: Jun. 23, 2021

Related U.S. Application Data

(62) Division of application No. 17/191,818, filed on Mar. 4, 2021, which is a division of application No. 16/431,291, filed on Jun. 4, 2019, now Pat. No. 10,988,439.

(51) Int. Cl.
  *C07C 233/64* (2006.01)
  *C07D 295/192* (2006.01)
  *A61P 35/00* (2006.01)
  *A61P 35/02* (2006.01)

(52) U.S. Cl.
  CPC ............ *C07C 233/64* (2013.01); *A61P 35/00* (2018.01); *A61P 35/02* (2018.01); *C07D 295/192* (2013.01)

(58) Field of Classification Search
  CPC ... C07C 233/64; C07D 295/192; A61P 35/00; A61P 35/02
  See application file for complete search history.

(56) References Cited

FOREIGN PATENT DOCUMENTS

WO  WO 2019196111 A1  10/2019

OTHER PUBLICATIONS

RN 1794852-22-4, registry database compound, 2015. (Year: 2015).*
Lu, et al. ; Discovery of potent and novel smoothened antagonists via structure-based virtual screening and biological assays ; European Journal of Medicinal Chemistry vol. 155 ; pp. 34-48 ; Jul. 15, 2018 ; Abstract Only ; 4 Pages.
Hu, et al. ; Discovery of novel nonpeptide allosteric inhibitors interrupting the interaction of CDK2/cyclin A3 by virtual screening and bioassays ; Bioorganic & Medicinal Chemistry letters, vol. 25, Issue 19 ; pp. 4069-4073 ; Oct. 1, 2015 ; Abstract Only ; 3 Pages.
Hanessian, et al. ; Phenolic P2 /P3 core motif as thrombin inhibitors—Design, synthesis, and X-ray co-crystal structure ; Bioorganic & Medicinal Chemistry Letters vol. 16, Issue 4 ; pp. 1032-1036 ; Feb. 15, 2006 ; Abstract Only ; 2 Pages.
Bisset, 1965, caplus an 1965:439288.
RN2203090-33-7, Apr. 1, 2018, file registry compound.
Kudryashova et al., 1973, cpalus an 1 973:546127.
RN2207482, Apr. 6, 2018, file registry compound.
RN878569-1 8-7, registry database compound, 2006.
RN1794852-22-4, registry database compound, 2015.
Bertinato et al., 2004, caplus an 2004:546481.
Cancer-Prevention, 2021, https://www.mdanderson.org/publications/focused-on-health/can-you-prevent-cancer-- a-conversation-with-ernest-hawk--m-d-.h 10-1593780.html.
Cancer-cure, 2021, https://www.medicalnewstoday.com/articles/322700#hodgkin-lymphoma.

* cited by examiner

*Primary Examiner* — Erich A Leeser
(74) *Attorney, Agent, or Firm* — Oblon, McClelland, Maier & Neustadt, L.L.P.

(57) ABSTRACT

Therapeutic compounds containing a phenyl core and amide link(s). Also described are pharmaceutical compositions incorporating the therapeutic compounds and a method for treating cancer with the compounds. These compounds are cytotoxic to stomach, colon, breast, and leukemia cancer cell lines via dual inhibition of Src kinases and tubulin.

3 Claims, 36 Drawing Sheets

Conditions: (a) Oxalyl chloride, dichloromethane, N,N-dimethylformamide (cat. amount). (b) $R_1NH_2$, Ethyl diisopropylamine, dichloromethane. (c) Tin chloride II dihydrate, ethylacetate, water, heat, or H-Cube Pro, Pd-C (10%), 10 atm, 40 °C, ethyl acetate

PHARMACEUTICAL COMPOSITION FOR TREATING CANCER

CROSS-REFERENCE TO RELATED APPLICATIONS

The present application is a Divisional of U.S. application Ser. No. 17/191,818, pending, having a filing date of Mar. 4, 2021 which is a Division of U.S. application Ser. No. 16/431,291, now U.S. Pat. No. 10,988,439, having a filing date of Jun. 4, 2019.

STATEMENT OF FUNDING ACKNOWLEDGEMENT

This project was funded by the Deanship of Scientific Research (DSR), King Abdulaziz University, Jeddah, the Kingdom of Saudi Arabia, under grant number RG-1-166-39.

BACKGROUND OF THE INVENTION

Technical Field

The present disclosure relates to a family of therapeutic compounds having a phenyl core and amide link(s). A pharmaceutical composition containing the compounds and a method for treating cancer are also disclosed.

Description of the Related Art

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly or impliedly admitted as prior art against the present invention.

The abnormal expression of protein tyrosine kinases (PTK) leads to cell proliferation disorder and is associated with tumor invasion, metastasis, and angiogenesis. Consequently, a variety of PTKs have been used as targets for screening anti-tumor drugs [Drake, J. M.; Lee, J. K.; Witte, O. N., Clinical targeting of mutated and wild-type protein tyrosine kinases in cancer. *Molecular and cellular biology* 2014, 34 (10), 1722-32]. Currently, all PTK inhibitors that are clinically available are those that occupy ATP pockets. Since ATP is inherently concentrated (mM) in cells, large quantities of the inhibitor must be delivered to ATP pockets to achieve adequate selectivity and affinity. A practical and under-utilized approach is to develop kinase inhibitors that bind to the substrate site. This approach might be effective because each kinase is specific to a unique peptide sequence.

The Src family of kinase enzymes (SFK) are non-receptor tyrosine kinases essential in signaling machinery [Guo, W.; Giancotti, F. G., Integrin signalling during tumour progression. *Nature reviews Molecular cell biology* 2004, 5 (10), 816]. Members of SFKs include Src, Yes, Fyn, Fgr, Lck, Hck, Blk, Yrk, and Lyn. SFKs are important for fundamental cellular processes such as cell growth, functions, survival, proliferation, differentiation, and migration [Lieu, C.; Kopetz, S., The SRC family of protein tyrosine kinases: a new and promising target for colorectal cancer therapy. *Clinical colorectal cancer* 2010, 9 (2), 89-94]. Aberrant activities of SFKs have been linked to a variety of cancers including those of the prostate, breast, colon, lungs, pancreas, brain, melanocytes and bone marrow [Frame, M. C.; Roskoski, R., Src Family Tyrosine Kinases. In *Reference Module in Life Sciences*, Elsevier: 2017]. Inhibitors of Src kinases such as dasatinib, bosutinib, saracatinib, KX-01, and KX-02 have been recently developed [Elsberger, B.; Stewart, B.; Tatarov, O.; Edwards, J., Is Src a viable target for treating solid tumours? *Current cancer drug targets* 2010, 10 (7), 683-694; Rothschild, S. I.; Gautschi, O.; Haura, E. B.; Johnson, F. M., Src inhibitors in lung cancer: current status and future directions. *Clinical lung cancer* 2010, 11 (4), 238-42; and Smolinski, M. P.; Bu, Y.; Clements, J.; Gelman, I. H.; Hegab, T.; Cutler, D. L.; Fang, J. W. S.; Fetterly, G.; Kwan, R.; Barnett, A.; Lau, J. Y. N.; Hangauer, D. G., Discovery of Novel Dual Mechanism of Action Src Signaling and Tubulin Polymerization Inhibitors (KX2-391 and KX2-361). *Journal of medicinal chemistry* 2018, 61 (11), 4704-4719, each incorporated herein by reference in their entirety]. In particular, KX-01 and KX-02 developed by Athenex possess intriguing biological mechanisms against cancer cells. In addition to Src inhibition, these two compounds also prevent cancer cell division via interference with tubulin [Tu, C.; Li, J.; Bu, Y.; Hangauer, D.; Qu, J., An ion-current-based, comprehensive and reproducible proteomic strategy for comparative characterization of the cellular responses to novel anticancer agents in a prostate cell model. *Journal of proteomics* 2012, 77, 187-201; and Anbalagan, M.; Ali, A.; Jones, R. K.; Marsden, C. G.; Sheng, M.; Carrier, L.; Bu, Y.; Hangauer, D.; Rowan, B. G., Peptidomimetic Src/pretubulin inhibitor KX-01 alone and in combination with paclitaxel suppresses growth, metastasis in human ER/PR/HER2-negative tumor xenografts. *Molecular cancer therapeutics* 2012, 11 (9), 1936-1947, each incorporated herein by reference in their entirety]. Despite these efforts there is still a need to develop more effective non-ATP competitive inhibitors as anticancer agents.

In view of the forgoing, one objective of the present disclosure is to provide therapeutic compounds with antiproliferative activities, a pharmaceutical composition comprising thereof, and a method for treating cancer.

BRIEF SUMMARY OF THE INVENTION

According to a first aspect, the present disclosure relates to a compound of formula

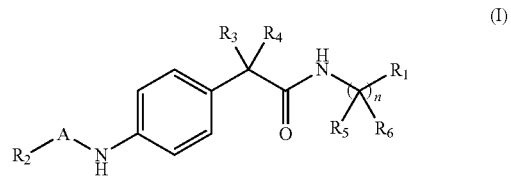

(I)

or a salt thereof, a solvate thereof, a tautomer thereof, a stereoisomer thereof, or a mixture thereof, wherein (i) $R_1$ is an optionally substituted aryl, or an optionally substituted heteroaryl, (ii) $R_2$ is selected from the group consisting of an optionally substituted alkyl, an optionally substituted cycloalkyl, an optionally substituted arylalkyl, an optionally substituted aryl, and an optionally substituted heteroaryl, (iii) $R_3$, $R_4$, $R_5$, and $R_6$ are independently selected from the group consisting of a hydrogen, an optionally substituted alkyl, and an optionally substituted cycloalkyl, (iv) A is .—C(O)—. or .—S(O)$_2$—., and (v) n is an integer in a range of 1-3.

In one embodiment, R₁ is selected from the group consisting of phenyl, p-methoxyphenyl, p-fluorophenyl, and 2-furanyl.

In one embodiment, R₁ is phenyl.

In one embodiment, R₂ is an optionally substituted alkyl, or an optionally substituted phenyl.

In one embodiment, R₂ is selected from the group consisting of methyl, ethyl, phenyl, p-aminophenyl, p-chlorophenyl, m-chlorophenyl, m-fluorophenyl, p-methylphenyl,

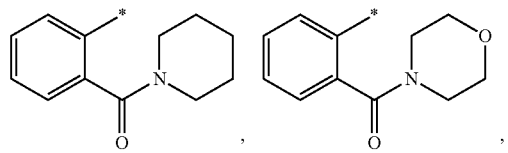

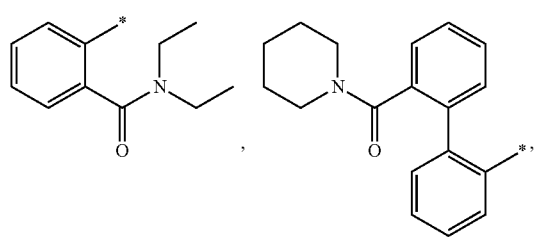

, and

In one embodiment, R₂ is selected from the group consisting of ethyl, phenyl, m-chlorophenyl, m-fluorophenyl, and

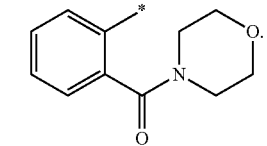 [SMILES: *c1ccccc1C(=O)N1CCOCC1]

In one embodiment, A is .—C(O)—.

In one embodiment, R₁ is phenyl, and R₂ is selected from the group consisting of ethyl, phenyl, m-chlorophenyl, m-fluorophenyl, and

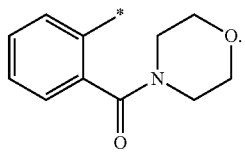 [SMILES: *c1ccccc1C(=O)N1CCOCC1]

In one embodiment, R₃, R₄, R₅, R₆ are hydrogen.

In one embodiment, n is 1.

In one embodiment, the compound of formula (I) of the first aspect is selected from the group consisting of According to a second aspect, the present disclosure relates to a pharmaceutical composition involving the compound of formula (I) of the first aspect, and a pharmaceutically acceptable carrier and/or excipient.

In one embodiment, the pharmaceutically acceptable carrier and/or excipient is at least one selected from the group consisting of a buffer, an inorganic salt, a fatty acid, a vegetable oil, a synthetic fatty ester, a surfactant, and a polymer.

In one embodiment, the pharmaceutical composition contains 0.1-90 wt % of the compound of formula (I) relative to a total weight of the pharmaceutical composition.

In one embodiment, the compound of formula (I) is selected from the group consisting of

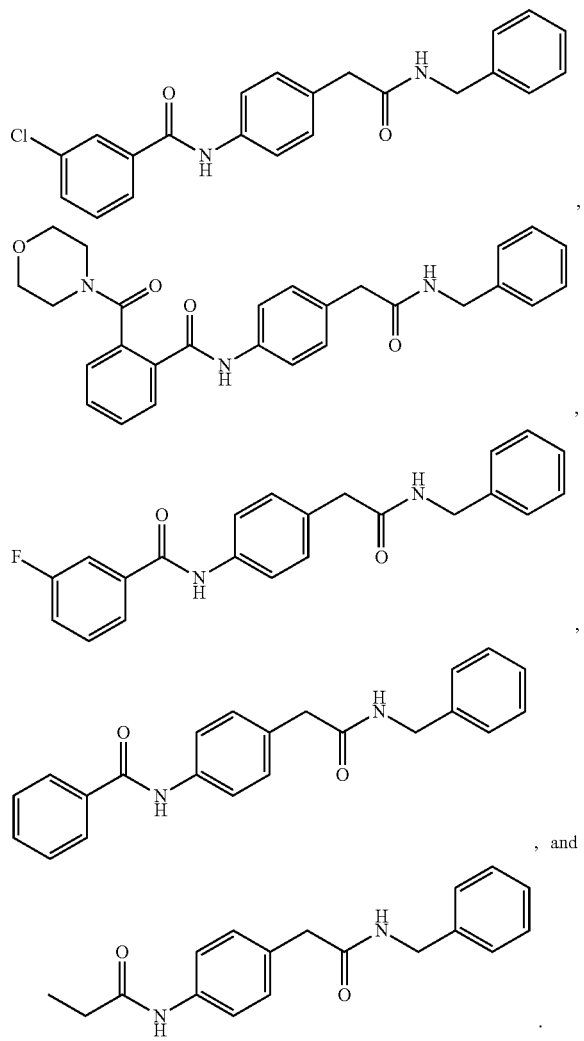

, and

According to a third aspect, the present disclosure relates to a method for treating a proliferative disorder. The method involves administering the pharmaceutical composition of the second aspect to a subject in need of therapy.

In one embodiment, 0.1-200 mg/kg of the compound of formula (I) is administered per body weight of the subject.

In one embodiment, the proliferative disorder is cancer.

In one embodiment, the cancer is at least one selected from the group consisting of breast cancer, stomach cancer, colon cancer, and leukemia.

In one embodiment, the subject is a mammal.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A more complete appreciation of the disclosure and many of the attendant advantages thereof will be readily obtained as the same becomes better understood by reference to the following detailed description when considered in connection with the accompanying drawings, wherein.

DETAILED DESCRIPTION OF THE EMBODIMENTS

Figure 1:
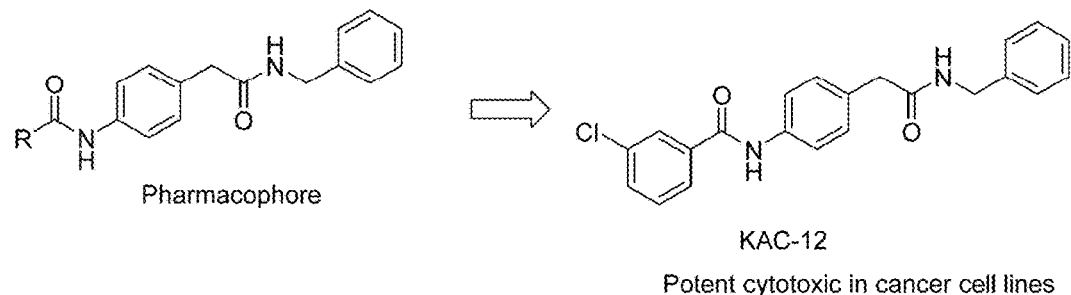
FIG. 1 is a schematic summary of the design of compounds of the present disclosure.

Embodiments of the present disclosure will now be described more fully hereinafter with reference to the accompanying drawings, in which some, but not all embodiments of the disclosure are shown.

As used herein, the words "a" and "an" and the like carry the meaning of "one or more". Within the description of this disclosure, where a numerical limit or range is stated, the endpoints are included unless stated otherwise. Also, all values and subranges within a numerical limit or range are specifically included as if explicitly written out.

As used herein, the terms "compound", "complex", and "product" are used interchangeably, and are intended to refer to a chemical entity, whether in the solid, liquid or gaseous phase, and whether in a crude mixture or purified and isolated.

As used herein, the term "solvate" refers to a physical association of a compound of this disclosure with one or more solvent molecules, whether organic or inorganic. This physical association includes hydrogen bonding. In certain instances, the solvate will be capable of isolation, for example when one or more solvent molecules are incorporated in the crystal lattice of the crystalline solid. The solvent molecules in the solvate may be present in a regular arrangement and/or a non-ordered arrangement. The solvate may comprise either a stoichiometric or nonstoichiometric amount of the solvent molecules. Solvate encompasses both solution phase and isolable solvates. Exemplary solvents include, but are not limited to, water, methanol, ethanol, n-propanol, isopropanol, n-butanol, isobutanol, tert-butanol, ethyl acetate and other lower alkanols, glycerine, acetone, dichloromethane (DCM), dimethyl sulfoxide (DMSO), dimethyl acetate (DMA), dimethylformamide (DMF), isopropyl ether, acetonitrile, toluene, N-methylpyrrolidone (NMP), tetrahydrofuran (THF), tetrahydropyran, other cyclic mono-, di- and tri-ethers, polyalkylene glycols (e.g. polyethylene glycol, polypropylene glycol, propylene glycol), and mixtures thereof in suitable proportions. Exemplary solvates include, but are not limited to, hydrates, ethanolates, methanolates, isopropanolates and mixtures thereof. Methods of solvation are generally known to those of ordinary skill in the art.

As used herein, the term "tautomer" refers to constitutional isomers of organic compounds that readily convert by tautomerization or tautomerism. The interconversion commonly results in the formal migration of a hydrogen atom or proton, accompanied by a switch of a single bond and adjacent double bond. Tautomerism is a special case of structural isomerism, and because of the rapid interconversion, tautomers are generally considered to be the same chemical compound. In solutions in which tautomerization is possible, a chemical equilibrium of the tautomers will be reached. The exact ratio of the tautomers depends on several factors including, but not limited to, temperature, solvent and pH. Exemplary common tautomeric pairs include, but are not limited to, ketone and enol, enamine and imine, ketene and ynol, nitroso and oxime, amide and imidic acid, lactam and lactim (an amide and imidic tautomerism in heterocyclic rings), and open-chain and cyclic forms of an acetal or hemiacetal (e.g., in reducing sugars).

As used herein, the term "stereoisomer" refers to isomeric molecules that have the same molecular formula and sequence of bonded atoms (i.e. constitution), but differ in the three-dimensional orientations of their atoms in space. This contrasts with structural isomers, which share the same molecular formula, but the bond connection of their order differs. By definition, molecules that are stereoisomers of each other represent the same structural isomer. Enantiomers are two stereoisomers that are related to each other by reflection, they are non-superimposable mirror images. Every stereogenic center in one has the opposite configuration in the other. Two compounds that are enantiomers of each other have the same physical properties, except for the direction in which they rotate polarized light and how they interact with different optical isomers of other compounds. Diastereomers are stereoisomers not related through a reflection operation, they are not mirror images of each other. These include meso compounds, cis- and trans- (E- and Z-) isomers, and non-enantiomeric optical isomers. Diastereomers seldom have the same physical properties. In terms of the present disclosure, stereoisomers may refer to enantiomers, diastereomers, or both.

Conformers, rotamers, or conformational isomerism refers to a form of isomerism that describes the phenomenon of molecules with the same structural formula but with different shapes due to rotations around one or more bonds. Different conformations can have different energies, can usually interconvert, and are very rarely isolatable. There are some molecules that can be isolated in several conformations. Atropisomers are stereoisomers resulting from hindered rotation about single bonds where the steric strain barrier to rotation is high enough to allow for the isolation of the conformers. In terms of the present disclosure, stereoisomers may refer to conformers, atropisomers, or both.

In terms of the present disclosure, stereoisomers of the ring systems, stereogenic centers, and the like can all be present in the compounds, and all such stable isomers are contemplated in the present disclosure. S- and R- (or L- and D-) stereoisomers of the compounds of the present disclosure are described and may be isolated as a mixture of isomers or as separated isomeric forms. All processes or methods used to prepare compounds of the present disclosure and intermediates made therein are considered to be part of the present disclosure. When stereoisomeric products are prepared, they may be separated by conventional methods, for example, by chromatography, fractional crystallization, or use of a chiral agent.

As used herein, the term "alkyl" unless otherwise specified refers to both branched and straight chain saturated aliphatic primary, secondary, and/or tertiary hydrocarbons of typically $C_1$ to $C_{21}$, for example $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, and specifically includes, but is not limited to, methyl, trifluoromethyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, 2,3-dimethylbutyl, 2-ethylhexyl, heptyl, octyl, nonyl, 3,7-dimethyloctyl, decyl, undecyl, dodecyl, tridecyl, 2-propylheptyl, tetradecyl, pentadecyl, hexadecyl, heptadecyl, octadecyl, nonadecyl, and eicosyl.

The term "cycloalkyl" refers to cyclized alkyl groups. Exemplary cycloalkyl groups include, but are not limited to, cyclopropyl, cyclobutyl, cyclopentyl, cyclohexyl, norbornyl, and adamantyl. Branched cycloalkyl groups such as exemplary 1-methylcyclopropyl and 2-methylcyclopropyl groups are included in the definition of cycloalkyl as used in the present disclosure.

The term "arylalkyl", as used herein, refers to a straight or branched chain alkyl moiety having 1 to 8 carbon atoms that is substituted by an aryl group as defined herein, and includes, but is not limited to, benzyl, phenethyl, 2-methylbenzyl, 3-methylbenzyl, 4-methylbenzyl, 2,4-dimethylbenzyl, 2-(4-ethylphenyl)ethyl, 3-(3-propylphenyl)propyl, and the like.

The term "aryl", as used herein, and unless otherwise specified, refers to phenyl, biphenyl, naphthyl, anthracenyl, and the like.

The term "heteroaryl" refers to an aryl group where at least one carbon atom is replaced with a heteroatom (e.g. nitrogen, oxygen, sulfur) and can be indolyl, furanyl, imidazolyl, triazolyl, triazinyl, oxazolyl, isoxazolyl, thiazolyl, isothiazolyl, pyrazolyl, pyrrolyl, pyrazinyl, tetrazolyl, pyridyl (or its N-oxide), thienyl, pyrimidinyl (or its N-oxide), 1H-indolyl, isoquinolyl (or its N-oxide), or quinolyl (or its N-oxide), for example.

The term "halogen", as used herein, means fluoro, chloro, bromo and iodo.

As used herein, the term "substituted" refers to at least one hydrogen atom that is replaced with a non-hydrogen group, provided that normal valencies are maintained and that the substitution results in a stable compound. When a substituent is noted as "optionally substituted", the substituents are selected from halo, hydroxyl, alkoxy, oxo, alkanoyl, aryloxy, alkanoyloxy, amino, alkylamino, arylamino, arylalkylamino, disubstituted amines (e.g. in which the two amino substituents are selected from the exemplary group including, but not limited to, alkyl, aryl or arylalkyl), alkanoylamino, aroylamino, aralkanoylamino, substituted alkanoylamino, substituted arylamino, substituted aralkanoylamino, thiol, alkylthio, arylthio, arylalkylthio, alkylthiono, arylthiono, aryalkylthiono, alkylsulfonyl, arylsulfonyl, arylalkylsulfonyl, sulfonamide (e.g. —SO$_2$NH$_2$), substituted sulfonamide, nitro, cyano, carboxy, unsubstituted amide (i.e. —CONH$_2$), substituted amide (e.g. —CONHalkyl, —CONHaryl, —CONHarylalkyl or cases where there are two substituents on one nitrogen from alkyl, aryl, or alkylalkyl), alkoxycarbonyl, aryl, substituted aryl, guanidine, heterocyclyl (e.g. indolyl, imidazoyl, furyl, thienyl, thiazolyl, pyrrolidyl, pyridyl, pyrimidiyl, pyrrolidinyl, piperidinyl, morpholinyl, piperazinyl, homopiperazinyl and the like), substituted heterocyclyl and mixtures thereof. The substituents may themselves be optionally substituted, and may be either unprotected, or protected as necessary, as known to those skilled in the art, for example, as taught in Greene, et al., "Protective Groups in Organic Synthesis", John Wiley and Sons, Second Edition, 1991, hereby incorporated by reference in its entirety.

The term "amide", as used herein, and unless otherwise specified, refers to an amide that is unsustituted (—C(O)NH$_2$), optionally monosubstituted (—C(O)NHR$_a$), or disubstituted (—C(O)NR$_a$R$_b$), where R$_a$ and R$_b$ are independently an optionally substituted alkyl, an optionally substituted cycloalkyl, an optionally substituted arylalkyl, or an optionally substituted aryl.

Disubstituted amides which are cyclic disubstituted amides are also contemplated as part of the disubstituted amide family, where R$_a$ and R$_b$ together form a cyclic ring with the nitrogen atom to which they are attached, thereby forming for example a 3-membered, 4-membered, 5-membered, 6-membered, 7-membered, or 8-membered ring. Exemplary cyclic disubstituted amides include, but are not limited to, N-pyrrolidylamide

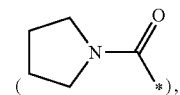

N-piperidinylamide

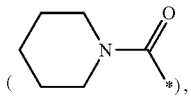

4-methylpiperidinylamide

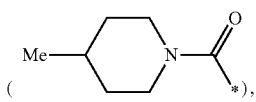 [SMILES: *C(=O)N1CCC(C)CC1]

morpholinylamide

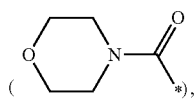

piperazinylamide

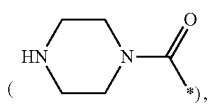

(N-methyl)piperazinylamide

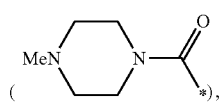

and homopiperazinylamide

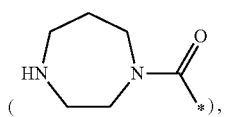

According to a first aspect, the present disclosure relates to a compound of formula (I)

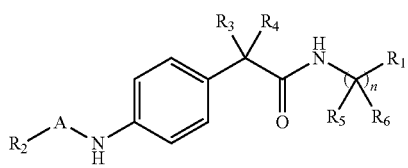

or a salt thereof, a solvate thereof, a tautomer thereof, a stereoisomer thereof, or a mixture thereof.

$R_1$ is an optionally substituted aryl, or an optionally substituted heteroaryl. Examples of $R_1$ include, but are not limited to, phenyl, p-methoxyphenyl, o-methoxyphenyl, p-fluorophenyl, o-fluorophenyl, p-chlorophenyl, o-chlorophenyl, p-bromophenyl, o-bromophenyl, 4-cyanophenyl, 2-furanyl, 2-thienyl, 3-methyl-2-thienyl, 3-methyl-2-pyridinyl, and 4-methyl-2-pyridinyl. In preferred embodiments, $R_1$ is selected from the group consisting of phenyl, p-methoxyphenyl, p-fluorophenyl, and 2-furanyl. In a most preferred embodiment, $R_1$ is phenyl.

$R_2$ is selected from the group consisting of an optionally substituted alkyl, an optionally substituted cycloalkyl, an optionally substituted arylalkyl, an optionally substituted aryl, and an optionally substituted heteroaryl.

In one embodiment, $R_2$ is an optionally substituted alkyl. In a preferred embodiment, $R_2$ is an unsubstituted alkyl, preferably a linear alkyl, preferably a linear $C_{1-8}$ alkyl, preferably a linear $C_{2-6}$ alkyl, preferably a linear $C_{3-4}$ alkyl. The carbon counts described herein refers to a number of carbon atoms of the alkyl group of $R_2$ which excludes the carbon atoms of optionally present substituents. Exemplary linear alkyls include, but are not limited to methyl, ethyl, n-propyl, n-butyl, n-pentyl, n-hexyl, n-heptyl, and n-octyl. Alternatively, $R_2$ is a branched alkyl, such as isopropyl, sec-butyl, isobutyl, isobutyl, tert-butyl, isopentyl, neopentyl, and isohexyl. In a most preferred embodiment, $R_2$ is methyl, or ethyl.

In another embodiment, $R_2$ is an optionally substituted phenyl. The phenyl of $R_2$ may be substituted with at least one substituent selected from the group consisting of a halogen, an alkyl, an amide, and an optionally substituted phenyl. In a preferred embodiment, the phenyl of $R_2$ is meta-substituted with at least one halogen such as a chloro, a fluoro, and a bromo. In another preferred embodiment, the phenyl of $R_2$ is ortho-substituted with at least one disubstituted amide, such as N,N-dimethylamide, N,N-diethylamide, pyrrolidylamide

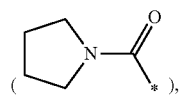

piperidinylamide

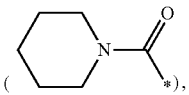

4-methylpiperidinylamide

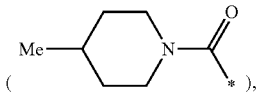

morpholinylamide

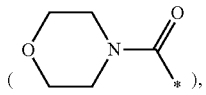

piperazinylamide

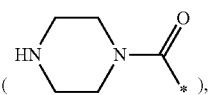

(N-methyl)piperazinylamide

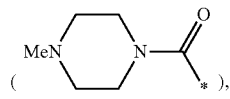

and homopiperazinylamide

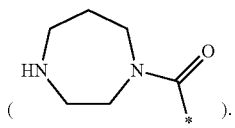 [SMILES: *C(=O)N1CCCNCC1]

In another preferred embodiment, the phenyl of $R_2$ is ortho-substituted with at least one substituted phenyl, preferably a phenyl that is ortho-substituted with at least one of the aforementioned disubstituted amides, such as N,N-dimethylamide, N,N-diethylamide, pyrrolidylamide

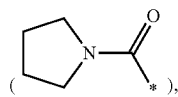

piperidinylamide

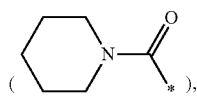

4-Methylpipeliumyiamme

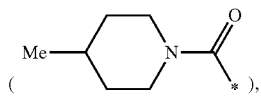

morpholinylamide

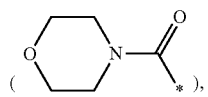

piperazinylamide

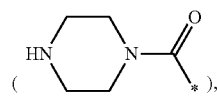

(N-methyl)piperazinylamide

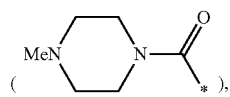

and homopiperazinylamide

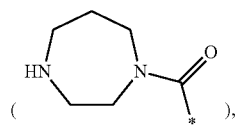

Alternatively, the phenyl of $R_2$ is unsubstituted.

In a preferred embodiment, $R_2$ is selected from the group consisting of methyl, ethyl, phenyl, p-aminophenyl, p-chlorophenyl, m-chlorophenyl, m-fluorophenyl, p-methylphenyl,

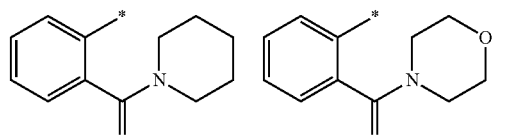

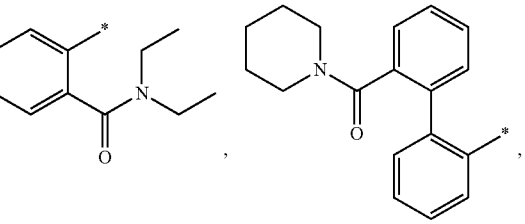

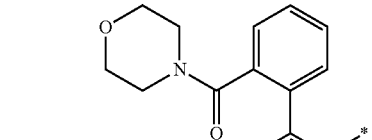

, and

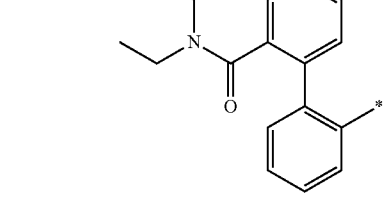

In a most preferred embodiment, $R_2$ is selected from the group consisting of ethyl, phenyl, m-chlorophenyl, m-fluorophenyl, and

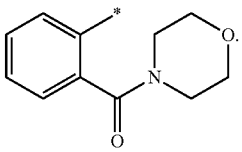 [SMILES: *c1ccccc1C(=O)N1CCOCC1]

$R_3$, $R_4$, $R_5$, and $R_6$ are independently selected from the group consisting of a hydrogen, an optionally substituted alkyl, and an optionally substituted cycloalkyl. In one or more embodiments, $R_3$ and $R_4$ are independently a hydrogen or an optionally substituted $C_{1-6}$ alkyl, $C_{2-5}$ alkyl, or a $C_{3-4}$ alkyl. In one embodiment, $R_3$ and $R_4$ are the same. In another embodiment, $R_3$ and $R_4$ are different. In one or more embodiments, $R_5$ and $R_6$ are independently a hydrogen or an optionally substituted $C_{1-6}$ alkyl, $C_{2-5}$ alkyl, or a $C_{3-4}$ alkyl. In one embodiment, $R_5$ and $R_6$ are the same. In another embodiment, $R_5$ and $R_6$ are different. In a most preferred embodiment, $R_3$, $R_4$, $R_5$, $R_6$ are a hydrogen.

A may be .—C(O)—. or .—S(O)$_2$—. In a preferred embodiment, A is .—C(O)—.

As used herein, the value of n denotes an alkyl chain of —CR$_5$R$_6$— groups connected between $R_1$ and amide groups of the compound of formula (I). In one or more embodiments, n is an integer in a range of 1-6, preferably 2-5, preferably 3-4. Preferably, n is 1 or 2. Most preferably, n is 1.

In some embodiments, the compound of formula (I) is one or more of the following structures:

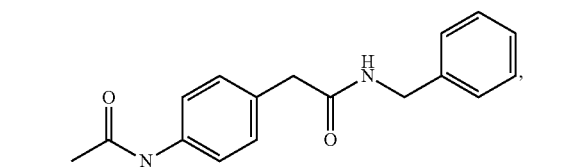

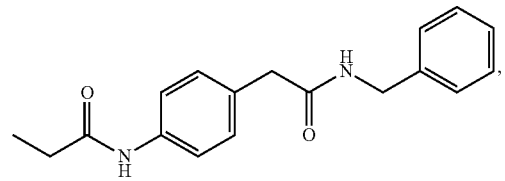

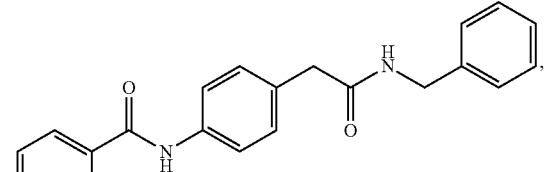

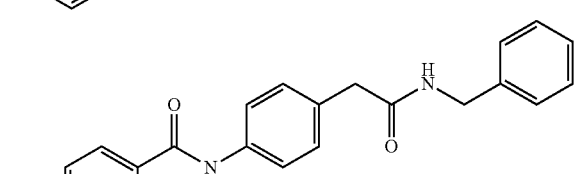

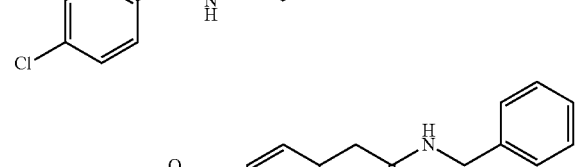

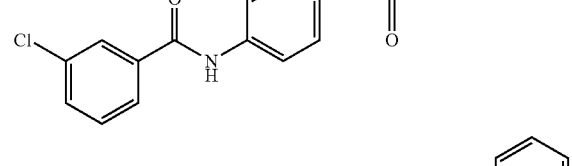

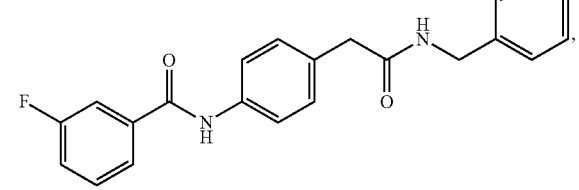

-continued

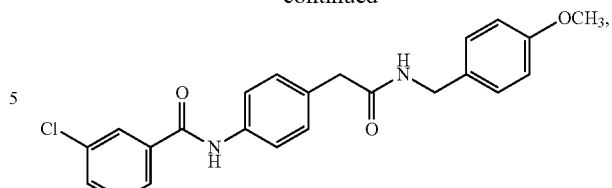

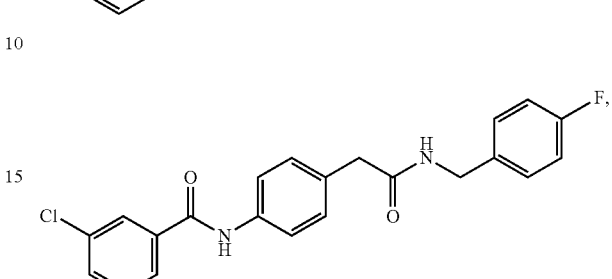

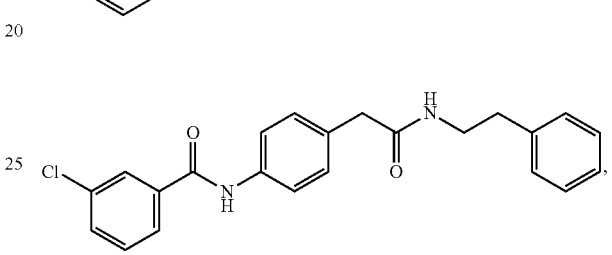

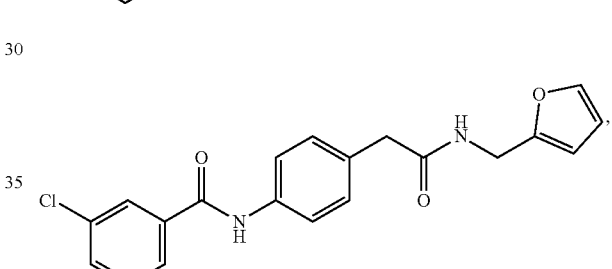

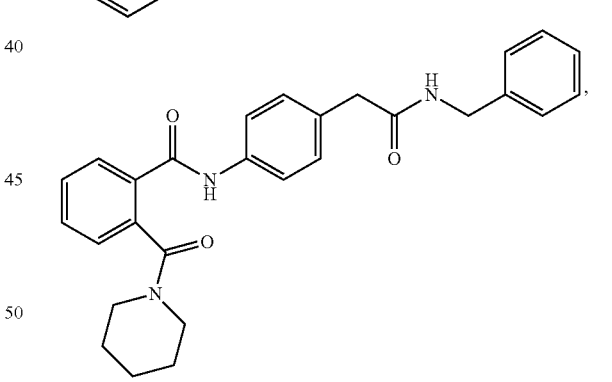

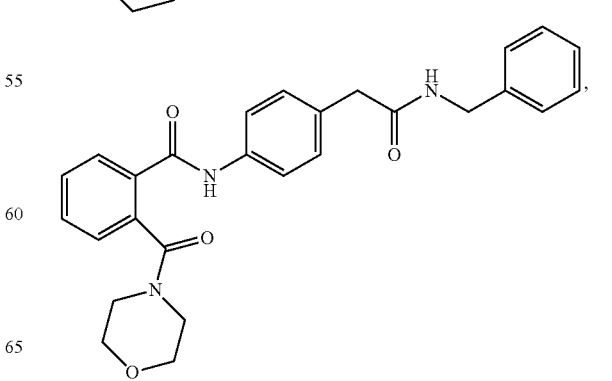

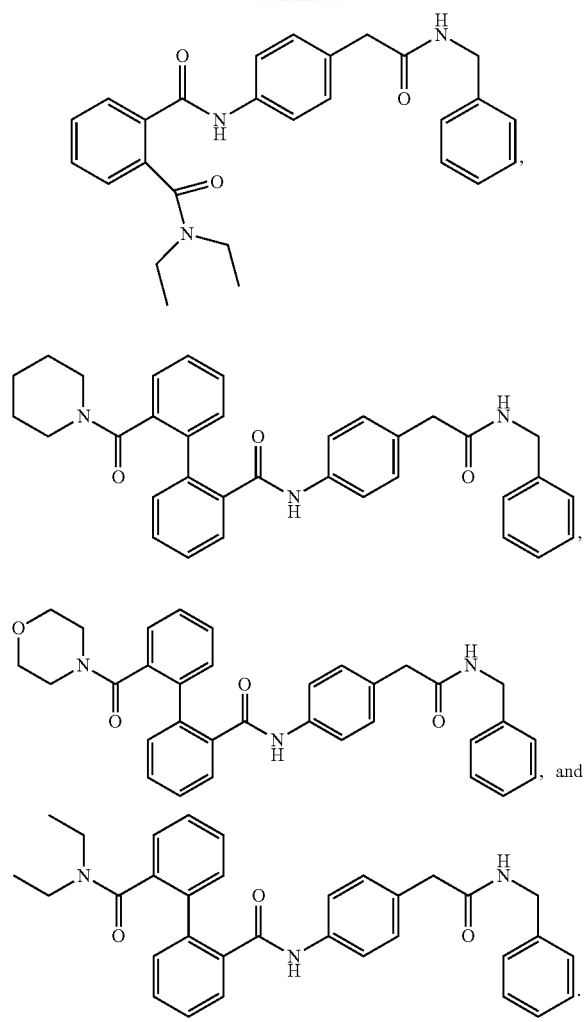

In at least one embodiment, $R_1$ is phenyl, and $R_2$ is selected from the group consisting of ethyl, phenyl, m-chlorophenyl, m-fluorophenyl, and

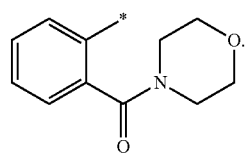

In a most preferred embodiment, the compound of formula (I) is selected from the group consisting of

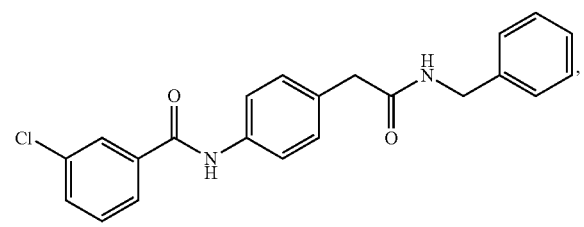

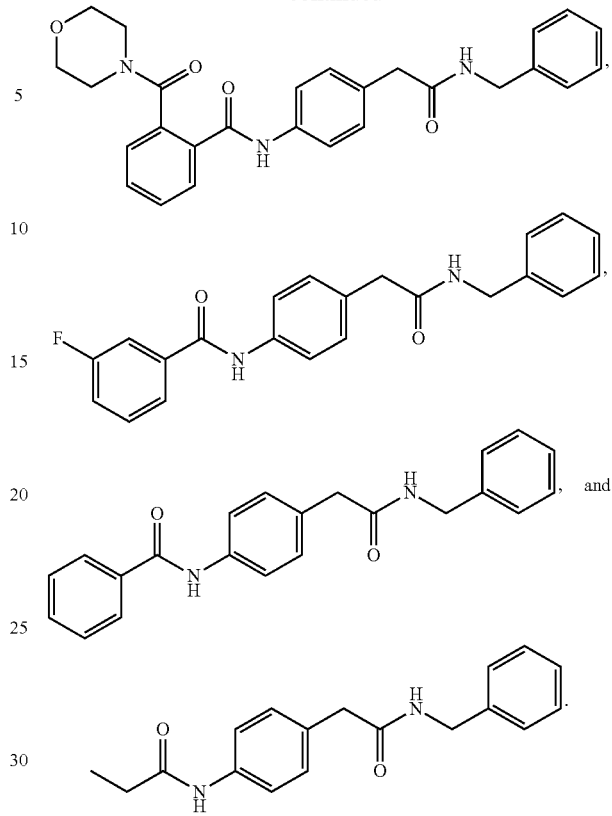

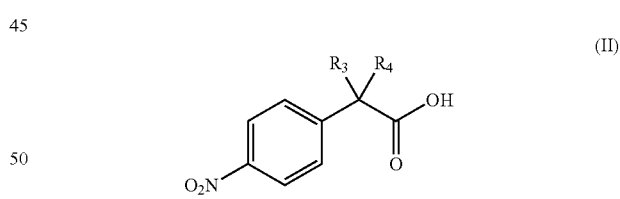

The compounds of the present disclosure may be prepared by methods known to those of ordinary skills in the art. The following methods set forth below are provided for illustrative purposes and are not intended to limit the scope of the disclosure.

Figure 3:
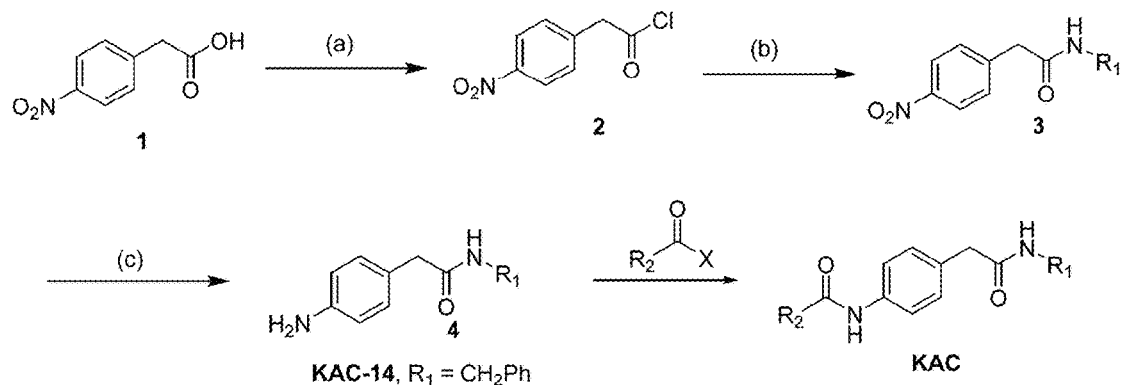
FIG. 3 is a scheme illustrating the synthesis of KAC series.

The compounds of formula (I) may, for example, be synthesized according to a process illustrated in FIG. 3.

Briefly, the compounds may be formed via (i) a reaction between a nitrophenyl compound of formula (II)

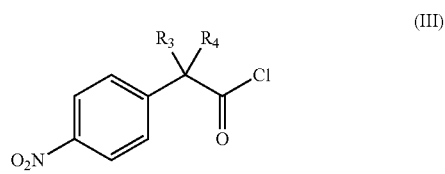

(II)

or a salt, solvate, tautomer or stereoisomer thereof, with a reagent such as oxalyl chloride, thionyl chloride, phosphorus trichloride ($POCl_3$), and phosphorous pentachloride ($POCl_5$) to form an acyl chloride compound of formula (III)

(III)

or a salt, solvate, tautomer or stereoisomer thereof, wherein $R_3$ and $R_4$ are as previously specified, or via any other activated acyl chemistry known to those of ordinary skill (e.g., anhydride, acyl bromide, etc.); (ii) a first amidation reaction between the acyl group of compound of formula (III) and an amine of formula (IV)

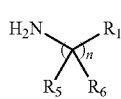
(IV)

or a salt, solvate, or stereoisomer thereof, in the presence of a base, to form a nitrophenyl amide of formula (V)

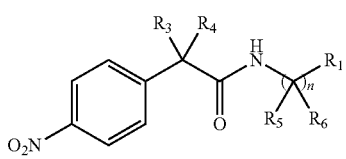
(V)

or a salt, solvate, tautomer or stereoisomer thereof, wherein $R_1$, $R_5$, $R_6$, and n are as previously specified; (iii) a reduction reaction of the nitrophenyl amide of formula (V) using a reducing reagent, thereby forming an aminophenyl amide of formula (VI)

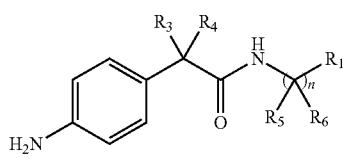
(VI)

or a salt, solvate, tautomer or stereoisomer thereof.

Reduction methods of nitro groups are generally known to those of ordinary skills in the art. Exemplary reducing methods and/or reagents include, but are not limited to, tin(II) chloride, catalytic hydrogenation over palladium-on-carbon, Raney nickel, sodium sulfide, iron metal in acetic acid, sodium borohydride, lithium borohydride, and Baker's yeast.

In one embodiment, the $R_2$ side chain of compound of formula (I) may be incorporated via a second amidation reaction between the amine group of compound of formula (VI) and a compound of formula (VII)

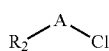
(VII)

or a salt, solvate, or tautomer thereof, in the presence of a base, thereby forming the compound of formula (I), wherein $R_2$ and A are as previously specified.

The aforementioned amidation reactions may be performed at a temperature in a range of −10-35° C., 0-25° C., or 4-15° C. in a solvent such as methylene chloride, chloroform, tetrahydrofuran, benzene, xylene, dimethylformamide, ethyl acetate, diethyl ether, acetonitrile, dimethyl sulfoxide, nitrobenzene, isopropanol, and mixtures thereof.

Preferably, methylene chloride is used as the solvent for the amidation reactions. In a preferred embodiment, a molar ratio of the amine of formula (IV) to the acyl chloride compound of formula (III) is in a range of 0.7:1 to 2:1, preferably 0.9:1 to 1.5:1, or about 1:1. In another preferred embodiment, a molar ratio of the aminophenyl amide of formula (VI) to the compound of formula (VII) is in a range of 0.7:1 to 2:1, preferably 0.9:1 to 1.5:1, or about 1:1.

Exemplary bases that may be used herein for the amidation reactions include, without limitation, inorganic bases such as lithium hydroxide, sodium hydroxide, potassium hydroxide, rubidium hydroxide, and cesium hydroxide, and organic bases such as trimethylamine, trimethylamine, diisopropylethylamine (DIPEA), triisopropylamine, dimethylaminopropylamine, N-methylmorpholine, N-methylpyrrolidine, 4-dimethylaminopyridine (DMAP), 1,8-diazabicyclo[5.4.0]undec-7-ene (DBU), and mixtures thereof. Preferably, an inorganic base is used herein for the amidation. More preferably, DIPEA is used as the base. In one embodiment, a molar ratio of the base to the respective amine is in a range of 1:1 to 10:1, preferably 2:1 to 8:1, more preferably 4:1 to 6:1.

The progress of the reactions may be monitored by methods known to those of ordinary skill in the art, such as thin layer chromatography, gas chromatography, nuclear magnetic resonance, infrared spectroscopy, and high pressure liquid chromatography combined with ultraviolet detection or mass spectroscopy. The compounds of formula (I) may be isolated and purified by methods known to those of ordinary skill in the art, such as crystallization, filtration through a celite containing cartridge, evaporating the reaction mixture to dryness, aqueous work-up, extraction with organic solvents, distillation, column chromatography, and high pressure liquid chromatography (HPLC) on normal phase or reversed phase. Preferred methods include column chromatography and recrystallization.

According to a second aspect, the present disclosure relates to a pharmaceutical composition involving the compound of formula (I) of the first aspect, and a pharmaceutically acceptable carrier and/or excipient.

As used herein, a "composition" or a "pharmaceutical composition" refers to a mixture of the active ingredient with other chemical components, such as pharmaceutically acceptable carriers and excipients. One purpose of a composition is to facilitate administration of the compound disclosed herein in any of its embodiments to a subject. Pharmaceutical compositions of the present disclosure may be manufactured by processes well known in the art, e.g., by means of conventional mixing, dissolving, granulating, dragee-making, levigating, emulsifying, encapsulating, entrapping or lyophilizing processes. Depending on the intended mode of administration (oral, parenteral, or topical), the composition can be in the form of solid, semi-solid or liquid dosage forms, such as tablets, suppositories, pills, capsules, powders, liquids, or suspensions, preferably in unit dosage form suitable for single administration of a precise dosage.

The term "active ingredient", as used herein, refers to an ingredient in the composition that is biologically active, for example, the compound represented by formula (I), a salt thereof, a solvate thereof, a tautomer thereof, a stereoisomer thereof, or any mixtures thereof. In some embodiments, other active ingredients in addition to the compound of the current disclosure may be incorporated into a pharmaceutical composition.

In one or more embodiments, the compound of formula (I) is selected from the group consisting of

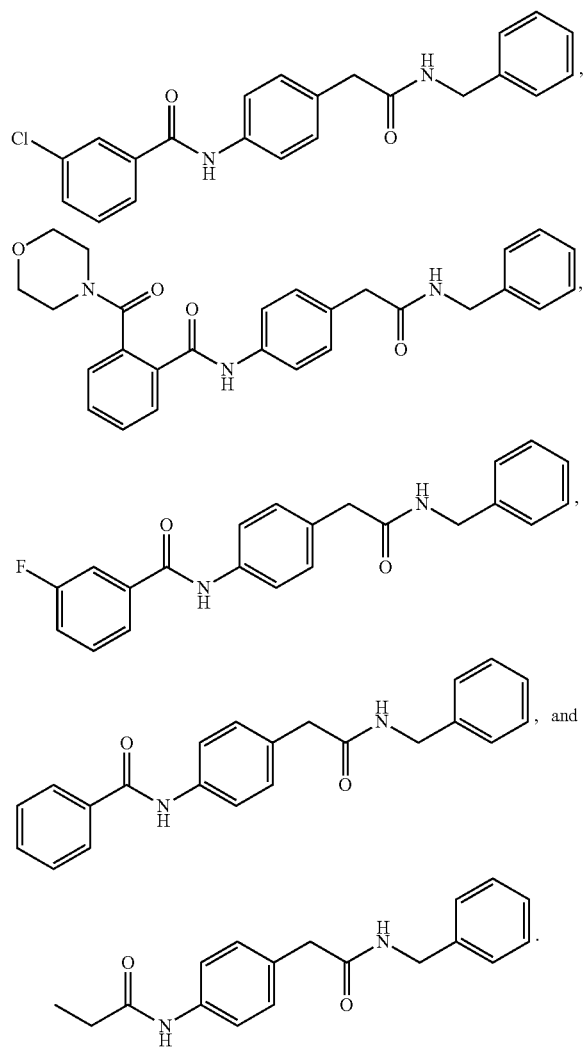

In one embodiment, the pharmaceutical composition comprises 0.1-90 wt % of the compound of formula (I) relative to a total weight of the pharmaceutical composition. In preferred embodiments, the pharmaceutical composition comprises at least 0.01 wt %, at least 0.05 wt %, at least 0.1 wt %, at least 0.5 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, at least 99 wt %, or at least 99.9 wt % of the compound of formula (I) relative to a total weight of the pharmaceutical composition. The pharmaceutical composition may contain 0.5-500 μM of the compound of formula (I) relative to a total volume of the composition, preferably 1-400 μM, preferably 10-300 μM, preferably 20-200 μM of the compound of formula (I) relative to the total volume of the composition. In some embodiments, the composition comprises up to 0.1 wt %, up to 1 wt %, up to 5 wt %, up to 10 wt %, up to 25 wt %, or up to 50 wt % of a pharmaceutically acceptable salt of the compound of formula (I). In some embodiments, the composition comprises up to 0.1 wt %, 1 wt %, 5 wt %, or 10 wt % of a pharmaceutically acceptable solvate of the gold(III) complex of formula (I). In one or more embodiments, the pharmaceutical composition comprises up to 0.01%, up to 0.1%, up to 1%, up to 5%, or up to 10% by weight of the pharmaceutically acceptable carrier and/or excipient relative to a total weight of the pharmaceutical composition. Preferably, the composition may further comprise pharmaceutically acceptable binders, such as sucrose, lactose, xylitol, and pharmaceutically acceptable excipients such as calcium carbonate, calcium phosphate, and dimethyl sulfoxide (DMSO).

Figure 2:
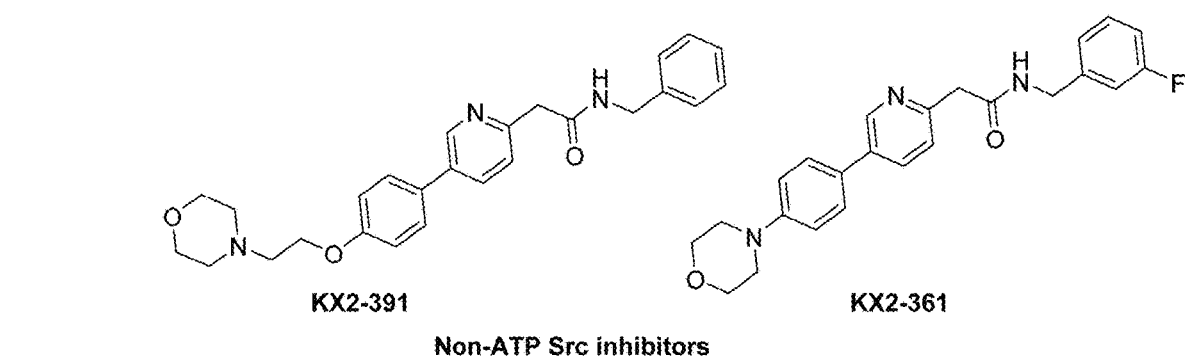
FIG. 2 is a scheme illustrating the design of KAC series via re-scaffolding of KX series.
Figure 2:
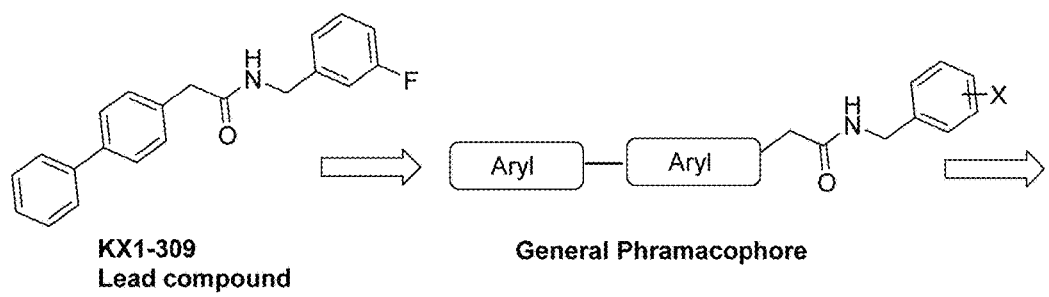
Figure 2:
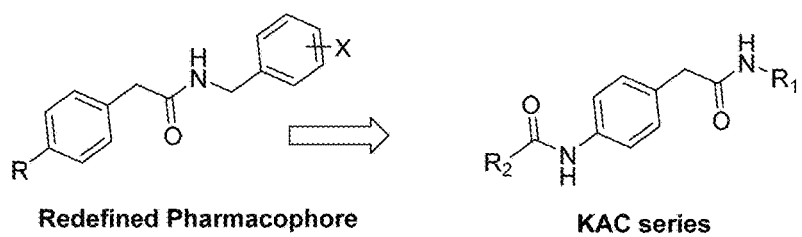

KX1-309 shown in FIG. 2 is the prototype of KX-01 (KX2-391) and KX-02 (KX2-361). The KX chemotype (biarylacetic acid derivatives) was found to exert cytotoxic activities via inhibiting both Src kinases and pre-tubulin. Changes in the scaffold (i.e. redefinition of the pharmacophore) may lead to attenuation or enhancement of the underlying dual mechanism of action of KX series. Such changes may also modify the affinity of SFK for other enzymes. KX-01 hinders cell proliferation of certain cancers via dual inhibition of Src-kinase and pre-tubulin.

In the present disclosure, the outer aryl group of KX series was truncated, and an amide group was attached at the para position of the phenyl acetic acid portion of the scaffold. Such structure modification may inhibit other kinases and/or the pre-tubulin, thus producing anticancer effect for different tumor classes.

In some embodiments, the active ingredient of the current disclosure, e.g. the compound of formula (I), a salt thereof, a solvate thereof, a tautomer thereof, a stereoisomer thereof, or any mixtures thereof, provides utility as an anticancer agent in reducing the viability of cancer cells derived from human cancer cell lines including, but not limited to, breast cancer cell lines (e.g. MCF-7, SK-BR-3), stomach cancer cell lines (e.g. N87, SNU-16), colon cancer cell lines (e.g. HCT-116, HT-29), leukemia cell lines (e.g. HL-60), liver cancer cell lines (e.g. HepG2), lung cancer cell lines (e.g. A549, NCI-H460), brain tumor cell lines (e.g. U251), ovarian cancer cell lines (e.g. NCI-ADR/RES, OVCAR-03), prostate cancer cell lines (e.g. PC-3), renal cancer cell lines (e.g. 786-0), and melanoma cell lines (e.g. UACC-62).

As used herein, other non-cancerous proliferative disorders that may also be treated by the currently disclosed pharmaceutical composition include, without limitation, atherosclerosis, rheumatoid arthritis, psoriasis, idiopathic pulmonary fibrosis, scleroderma, cirrhosis of the liver, lymphoproliferative disorder, other disorders characterized by epidermal cell proliferation such as verruca (warts), and dermatitis. The active ingredient of the current disclosure may also exhibit other therapeutic activities such as antimicrobial (e.g. antibacterial, antifungal, antiviral, antimycobacterial), antimalarial, pesticidal, antioxidant, as well as anti-inflammatory efficacies.

In some embodiments, the ability of the active ingredient to reduce the viability of cancer cells may be determined by contacting the pharmaceutical composition with the cancer cells and then performing cell viability assays. Methods of such assays include, but are not limited to, ATP test, Calcein AM assay, clonogenic assay, ethidium homodimer assay, Evans blue assay, fluorescein diacetate hydrolysis/Propidium iodide staining assay, flow cytometry, Formazan-based assays (MTT, XTT), green fluorescent protein assay, lactate dehydrogenase (LDH) assay, methyl violet assay, propidium iodide assay, Resazurin assay, trypan blue assay, and TUNEL assay. In a preferred embodiment, a MTT assay is used. In another preferred embodiment, a Resazurin assay is used.

In some embodiments, the cancer cells are derived from human cancer cell lines, including, but not limited to, breast cancer cell lines, e.g., MDA-MB-231, MCF7, T47D, and VP303, stomach cancer cell lines, e.g., N87, SNU-16, SNU-5, SNU-1, KATO III, AGS, colon cancer cell lines, e.g., HCT15, MDST8, GP5d, HCT116, DLD1, HT29, SW620, SW403 and T84, leukemia cell lines, e.g., HL-60, CESS, CCRF-CEM, CEM/C1, KASUMI-1, ARH-77, liver cancer cell lines, e.g. HepG2, PLC/PRF/5, THLE-3, C3A, SNU-182, SNU-398, SNU-387, SNU-423, SNU-475, SNU-449, and Hep 3B2.1-7, lung cancer cell lines, e.g., A549, SHP-77, COR-L23/R, and NCI-H69/LX20, cervical cancer cell Lines, e.g., HeLa DH, HtTA-1, HRS, and C-41, ovarian cancer cell lines, e.g., A2780, A2780cis, OV7, and PEO23, and skin cancer cell lines, e.g., C32TG, A375, and MCC26. In other embodiments, the cancer cells are collected from a human patient who is at risk of having, is suspected of having, has been diagnosed with, or is being monitored for recurrence of at least one type of cancer, preferably breast cancer, stomach cancer, colon cancer, and/or leukemia.

As used herein, the term "cytotoxic effective amount" refers to a concentration of the active ingredient that reduces the viability of the cancer cells by at least 5%, at least 10%, at least 15%, at least 20%, at least 30%, at least 40%, at least 50%, at least 60%, at least 70%, at least 80% or at least 90%, relative to cancer cells not treated with the active ingredient. The reduction in viability may occur no more than 10 days, no more than 7 days, no more than 5 days, no more than 3 days, or no more than 2 days after the active ingredient is contacted with the cancer cells. In one embodiment, the cytotoxic effective amount may be the $IC_{50}$ which is a concentration of the active ingredient which causes the death of 50% of cancer cells in 12-48 hours, 20-27 hours, or about 24 hours (1 day).

In one embodiment, the $IC_{50}$ of the compound of formula (I), the salt thereof, the solvate thereof, the tautomer thereof, the stereoisomer thereof, or the mixture thereof against stomach cancer cells is in a range of 1-100 µM, preferably 5-50 µM, more preferably 10-20 µM. In a preferred embodiment, the compound of formula (I) is

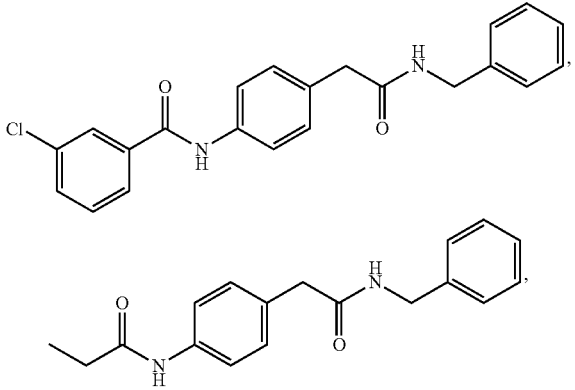

or both, and the $IC_{50}$ against stomach cancer cells is in a range of 1-10 µM, preferably 2-7 µM, or about 5 µM.

In another embodiment, the $IC_{50}$ of the compound of formula (I), the salt thereof, the solvate thereof, the tautomer thereof, the stereoisomer thereof, or the mixture thereof against leukemia cells is in a range of 0.5-100 µM, preferably 1-50 µM, more preferably 10-20 µM. In a preferred embodiment, the compound of formula (I) is

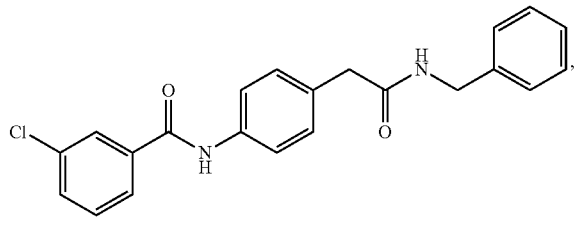 [SMILES: O=C(Cc1ccc(NC(=O)c2cccc(Cl)c2)cc1)NCc1ccccc1]

and the $IC_{50}$ against leukemia cells is in a range of 0.5-8 µM, preferably 1-5 µM, or about 4 µM.

In another embodiment, the $IC_{50}$ of the compound of formula (I), the salt thereof, the solvate thereof, the tautomer thereof, the stereoisomer thereof, or the mixture thereof against colon cancer cells is in a range of 1-100 µM, preferably 5-50 µM, more preferably 10-20 µM. In a preferred embodiment, the compound of formula (I) is

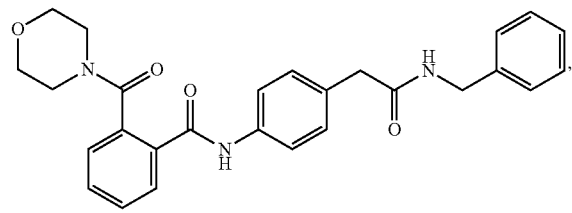 [SMILES: O=C(Cc1ccc(NC(=O)c2ccccc2C(=O)N2CCOCC2)cc1)NCc1ccccc1]

and the $IC_{50}$ against colon cancer cells is in a range of 1-10 µM, preferably 2-7 µM, or about 5 µM.

In another embodiment, the $IC_{50}$ of the gold(III) complex of formula (I), the salt thereof, the solvate thereof, the tautomer thereof, the stereoisomer thereof, or the mixture thereof against breast cancer cells is in a range of 0.1-50 µM, preferably 0.5-25 µM, more preferably 1-10 µM. In a preferred embodiment, the compound of formula (I) is

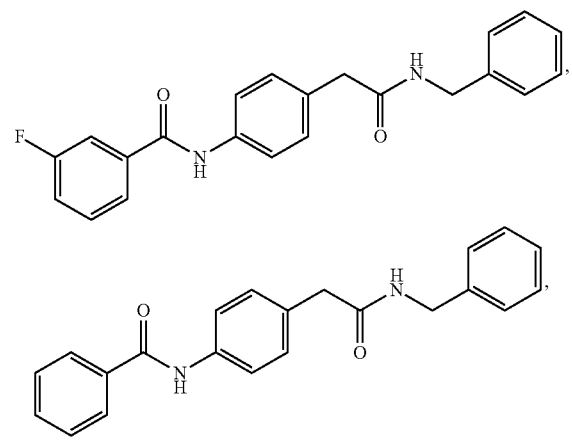

or both, and the $IC_{50}$ against breast cancer cells is in a range of 0.5-8 µM, preferably 1-5 µM, more preferably 2-4 µM.

In some embodiments, other active ingredients in addition to the compound of the current disclosure may be incorporated into the pharmaceutical composition. In one embodiment, the pharmaceutical composition includes a second active ingredient that is chemically distinct from the compound of formula (I), such as a chemotherapeutic agent or an anticancer agent, for the treatment or prevention of neoplasm, of tumor or cancer cell division, growth, proliferation and/or metastasis in the subject; induction of death or apoptosis of tumor and/or cancer cells; and/or any other forms of proliferative disorder.

The anticancer agent is at least one of a mitotic inhibitor; an alkylating agent; an antimetabolite; a cell cycle inhibitor; an enzyme; a topoisomerase inhibitor; a biological response modifier; an anti-hormone; a tubulin inhibitor; a tyrosine-kinase inhibitor; an antiangiogenic agent such as MMP-2, MMP-9 and COX-2 inhibitor; an anti-androgen; a platinum coordination complex (oxaliplatin, carboplatin); a substituted urea such as hydroxyurea; a methylhydrazine derivative; an adrenocortical suppressant, e.g., mitotane, aminoglutethimide; a hormone and/or hormone antagonist such as the adrenocorticosteriods (e.g., prednisone), progestins (e.g., hydroxyprogesterone caproate), an estrogen (e.g., diethylstilbestrol); an antiestrogen such as tamoxifen; androgen, e.g., testosterone propionate; and an aromatase inhibitor, such as anastrozole, and AROMASIN (exemestane).

Exemplary anticancer agents include, but are not limited to, tubulin binding agents including paclitaxel, epothilone, docetaxel, discodermolide, etoposide, vinblastine, vincristine, teniposide, vinorelbine, and vindesine; tyrosine-kinase inhibitors including imatinib, nilotinib, dasatinib, bosutinib, ponatinib, and bafetinib; alkylating antineoplastic agents including busulfan, carmustine, chlorambucil, cyclophosphamide, cyclophosphamide, dacarbazine, ifosfamide, lomustine, mechlorethamine, melphalan, mercaptopurine, procarbazine; antimetabolites including cladribine, cytarabine, fludarabine, gemcitabine, pentostatin, 5-fluorouracil, clofarabine, capecitabine, methotrexate, thioguanine; cytotoxic antibiotics including daunorubicin, doxorubicin, idarubicin, mitomycin, actinomycin, epirubicin; topoisomerase inhibitors including irinotecan, mitoxantrone, topotecan, and mixtures thereof.

As used herein, a "pharmaceutically acceptable carrier" refers to a carrier or diluent that does not cause significant irritation to an organism, does not abrogate the biological activity and properties of the administered active ingredient, and/or does not interact in a deleterious manner with the other components of the composition in which it is contained. The term "carrier" encompasses any excipient, binder, diluent, filler, salt, buffer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g. Remington's Pharmaceutical Sciences, 21st Edition, ed. University of the Sciences in Philadelphia, Lippincott, Williams & Wilkins, Philadelphia Pa., 2005, which is incorporated herein by reference in its entirety). Examples of physiologically acceptable carriers include antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN® (ICI, Inc.; Bridgewater, N.J.), polyethylene glycol (PEG), and PLURONICS™ (BASF; Florham Park, N.J.). An "excipient" refers to an inert substance added to a composition to further facilitate administration of a compound.

Examples, without limitation, of excipients include calcium carbonate, calcium phosphate, various sugars and types of starch, cellulose derivatives, gelatin, vegetable oils, and polyethylene glycols.

In one or more embodiments, the pharmaceutically acceptable carrier and/or excipient is at least one selected from the group consisting of a buffer, an inorganic salt, a fatty acid, a vegetable oil, a synthetic fatty ester, a surfactant, and a polymer.

Exemplary buffers include, but are not limited to, phosphate buffers, citrate buffer, acetate buffers, borate buffers, carbonate buffers, bicarbonate buffers, and buffers with other organic acids and salts.

Exemplary inorganic salts include, but are not limited to, calcium carbonate, calcium phosphate, disodium hydrogen phosphate, potassium hydrogen phosphate, sodium chloride, zinc oxide, zinc sulfate, and magnesium trisilicate.

Exemplary fatty acids include, but are not limited to, an omega-3 fatty acid (e.g., linolenic acid, docosahexaenoic acid, eicosapentaenoic acid) and an omega-6 fatty acid (e.g., linoleic acid, eicosadienoic acid, arachidonic acid). Other fatty acids, such as oleic acid, palmitoleic acid, palmitic acid, stearic acid, and myristic acid, may be included.

Exemplary vegetable oils include, but are not limited to, avocado oil, olive oil, palm oil, coconut oil, rapeseed oil, soybean oil, corn oil, sunflower oil, cottonseed oil, and peanut oil, grape seed oil, hazelnut oil, linseed oil, rice bran oil, safflower oil, sesame oil, brazil nut oil, carapa oil, passion fruit oil, and cocoa butter.

Exemplary synthetic fatty esters include, without limitation, methyl, ethyl, isopropyl and butyl esters of fatty acids (e.g., isopropyl palmitate, glyceryl stearate, ethyl oleate, isopropyl myristate, isopropyl isostearate, diisopropyl sebacate, ethyl stearate, di-n-butyl adipate, dipropylene glycol pelargonate), $C_{12}$-$C_{16}$ fatty alcohol lactates (e.g., cetyl lactate and lauryl lactate), propylene dipelargonate, 2-ethylhexyl isononoate, 2-ethylhexyl stearate, isopropyl lanolate, 2-ethylhexyl salicylate, cetyl myristate, oleyl myristate, oleyl stearate, oleyl oleate, hexyl laurate, isohexyl laurate, propylene glycol fatty ester, and polyoxyethylene sorbitan fatty ester. As used herein, the term "propylene glycol fatty ester" refers to a monoether or diester, or mixtures thereof, formed between propylene glycol or polypropylene glycol and a fatty acid. The term "polyoxyethylene sorbitan fatty ester" denotes oleate esters of sorbitol and its anhydrides, typically copolymerized with ethylene oxide.

Surfactants may act as detergents, wetting agents, emulsifiers, foaming agents, and dispersants. Surfactants that may be present in the compositions of the present disclosure include zwitterionic (amphoteric) surfactants, e.g., phosphatidylcholine, and 3-[(3-cholamidopropyl)dimethylammonio]-1-propanesulfonate (CHAPS), anionic surfactants, e.g., sodium lauryl sulfate, sodium octane sulfonate, sodium decane sulfonate, and sodium dodecane sulfonate, non-ionic surfactants, e.g., sorbitan monolaurate, sorbitan monopalmitate, sorbitan trioleate, polysorbates such as polysorbate 20 (Tween 20), polysorbate 60 (Tween 60), and polysorbate 80 (Tween 80), cationic surfactants, e.g., decyltrimethylammonium bromide, dodecyltrimethylammonium bromide, tetradecyltrimethylammonium bromide, tetradecyltrimethyl-ammonium chloride, and dodecylammonium chloride, and combinations thereof.

Exemplary polymers include, without limitation, polylactides, polyglycolides, polycaprolactones, polyanhydrides, polyurethanes, polyesteramides, polyorthoesters, polydioxanones, polyacetals, polyketals, polycarbonates, polyorthocarbonates, polyphosphazenes, polyhydroxybutyrates, polyhydroxyvalerates, polyalkylene oxalates, polyalkylene succinates, poly(malic acid), poly(maleic anhydride), a polyvinyl alcohols, and copolymers, terpolymers, or combinations or mixtures therein. The copolymer/terpolymer may be a random copolymer/terpolymer, or a block copolymer/terpolymer.

Depending on the route of administration e.g. oral, parental, or topical, the composition may be in the form of solid dosage form such as tablets, caplets, capsules, powders, and granules, semi-solid dosage form such as ointments, creams, lotions, gels, pastes, and suppositories, liquid dosage forms such as solutions, and dispersions, inhalation dosage form such as aerosols, and spray, or transdermal dosage form such as patches.

Solid dosage forms for oral administration can include capsules, tablets, pills, powders, and granules. In such solid dosage forms, the active ingredient is ordinarily combined with one or more adjuvants appropriate to the indicated route of administration. If administered per os, the active ingredient can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering ingredients such as sodium citrate, magnesium or calcium carbonate or bicarbonate. Tablets and pills can additionally be prepared with enteric coatings.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting ingredients, emulsifying and suspending ingredients, and sweetening, flavouring, and perfuming ingredients.

For therapeutic purposes, formulations for parenteral administration can be in the form of aqueous or non-aqueous isotonic sterile injection solutions or suspensions. The term "parenteral", as used herein, includes intravenous, intravesical, intraperitoneal, subcutaneous, intramuscular, intralesional, intracranial, intrapulmonal, intracardial, intrasternal, and sublingual injections, or infusion techniques. These solutions and suspensions can be prepared from sterile powders or granules having one or more of the carriers or diluents mentioned for use in the formulations for oral administration. The active ingredient can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Injectable preparations, for example, sterile injectable aqueous or oleaginous suspensions can be formulated according to the known art using suitable dispersing or wetting ingredients and suspending ingredients. The sterile injectable preparation can also be a sterile injectable solution or suspension in a non-toxic parenterally acceptable diluent or solvent, for example, as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids, such as oleic acid, find use in the preparation of injectables. Dimethyl acetamide, surfactants including ionic and non-ionic detergents, polyethylene glycols can be used. Mixtures of solvents and wetting ingredients such as those discussed above are also useful.

Suppositories for rectal administration can be prepared by mixing the active ingredient with a suitable non-irritating excipient, such as cocoa butter, synthetic mono-, di-, or triglycerides, fatty acids, and polyethylene glycols that are solid at ordinary temperatures but liquid at the rectal temperature and will therefore melt in the rectum and release the drug.

Topical administration may involve the use of transdermal administration such as transdermal patches or iontophoresis devices. Formulation of drugs is discussed in, for example, Hoover, J. E. Remington's pharmaceutical sciences, Mack Publishing Co., Easton, Pa., 1975; and Liberman, H. A.; Lachman, L., Eds. Pharmaceutical dosage forms, Marcel Decker, New York, N.Y., 1980, which are incorporated herein by reference in their entirety.

In other embodiments, the pharmaceutical composition having the compound of formula (I), the salt thereof, the solvate thereof, the tautomer thereof, the stereoisomer thereof, or the mixture thereof has different release rates categorized as immediate release and controlled- or sustained-release.

As used herein, immediate release refers to the release of an active ingredient substantially immediately upon administration. In another embodiment, immediate release occurs when there is dissolution of an active ingredient within 1-20 minutes after administration. Dissolution can be of all or less than all (e.g. about 70%, about 75%, about 80%, about 85%, about 90%, about 91%, about 92%, about 93%, about 94%, about 95%, about 96%, about 97%, about 98%, about 99%, about 99.5%, 99.9%, or 99.99%) of the active ingredient. In another embodiment, immediate release results in complete or less than complete dissolution within about 1 hour following administration. Dissolution can be in a subject's stomach and/or intestine. In one embodiment, immediate release results in dissolution of an active ingredient within 1-20 minutes after entering the stomach. For example, dissolution of 100% of an active ingredient can occur in the prescribed time. In another embodiment, immediate release results in complete or less than complete dissolution within about 1 hour following rectal administration. In some embodiments, immediate release is through inhalation, such that dissolution occurs in a subject's lungs.

Controlled-release, or sustained-release, refers to a release of an active ingredient from a composition or dosage form in which the active ingredient is released over an extended period of time. In one embodiment, controlled-release results in dissolution of an active ingredient within 20-180 minutes after entering the stomach. In another embodiment, controlled-release occurs when there is dissolution of an active ingredient within 20-180 minutes after being swallowed. In another embodiment, controlled-release occurs when there is dissolution of an active ingredient within 20-180 minutes after entering the intestine. In another embodiment, controlled-release results in substantially complete dissolution after at least 1 hour following administration. In another embodiment, controlled-release results in substantially complete dissolution after at least 1 hour following oral administration. In another embodiment, controlled-release results in substantially complete dissolution after at least 1 hour following rectal administration. In one embodiment, the pharmaceutical composition described herein is not a controlled-release composition.

According to a third aspect, the present disclosure relates to a method for treating a proliferative disorder. The method involves administering the pharmaceutical composition of the second aspect to a subject in need of therapy.

In one or more embodiments, the proliferative disorder is cancer. In some embodiments, the disclosed method of the current aspect is for treating cancer of the blood, stomach, breast, colon, brain, bladder, lung, cervix, ovary, rectum, pancreas, skin, prostate gland, spleen, liver, kidney, head, neck, testicle, bone, bone marrow, thyroid gland, or central nervous system. In a preferred embodiment, the cancer is at least one selected from the group consisting of breast cancer, stomach cancer, colon cancer, and leukemia.

As used herein, the terms "treat", "treatment", and "treating" in the context of the administration of a therapy to a subject in need thereof refer to the reduction or inhibition of the progression and/or duration of a disease (e.g. cancer), the reduction or amelioration of the severity of the disease, and/or the amelioration of one or more symptoms thereof resulting from the administration of one or more therapies. "Treating" or "treatment" of the disease includes preventing the disease from occurring in a subject that may be predisposed to the disease but does not yet experience or exhibit symptoms of the disease (prophylactic treatment), inhibiting the disease (slowing or arresting its development), ameliorating the disease, providing relief from the symptoms or side-effects of the disease (including palliative treatment), and relieving the disease (causing regression of the disease). With regard to the disease, these terms simply mean that one or more of the symptoms of the disease will be reduced. Such terms may refer to one, two, three, or more results following the administration of one, two, three, or more therapies: (1) a stabilization, reduction (e.g. by more than 10%, 20%, 30%, 40%, 50%, preferably by more than 60% of the population of cancer cells and/or tumor size before administration), or elimination of the cancer cells, (2) inhibiting cancerous cell division and/or cancerous cell proliferation, (3) relieving to some extent (or, preferably, eliminating) one or more symptoms associated with a pathology related to or caused in part by unregulated or aberrant cellular division, (4) an increase in disease-free, relapse-free, progression-free, and/or overall survival, duration, or rate, (5) a decrease in hospitalization rate, (6) a decrease in hospitalization length, (7) eradication, removal, or control of primary, regional and/or metastatic cancer, (8) a stabilization or reduction (e.g. by at least 10%, 20%, 30%, 40%, 50%, 60%, 70%, preferably at least 80% relative to the initial growth rate) in the growth of a tumor or neoplasm, (9) an impairment in the formation of a tumor, (10) a reduction in mortality, (11) an increase in the response rate, the durability of response, or number of patients who respond or are in remission, (12) the size of the tumor is maintained and does not increase or increases by less than 10%, preferably less than 5%, preferably less than 4%, preferably less than 2%, (13) a decrease in the need for surgery (e.g. colectomy, mastectomy), and (14) preventing or reducing (e.g. by more than 10%, more than 30%, preferably by more than 60% of the population of metastasized cancer cells before administration) the metastasis of cancer cells.

The term "subject" and "patient" are used interchangeably. As used herein, they refer to any subject for whom or which therapy, including with the compositions according to the present disclosure is desired. In most embodiments, the subject is a mammal, including but not limited to a human, a non-human primate such as a chimpanzee, a domestic livestock such as a cattle, a horse, a swine, a pet animal such as a dog, a cat, and a rabbit, and a laboratory subject such as a rodent, e.g. a rat, a mouse, and a guinea pig. In preferred embodiments, the subject is a human.

As used herein, a subject in need of therapy includes a subject already with the disease, a subject which does not yet experience or exhibit symptoms of the disease, and a subject predisposed to the disease. In preferred embodiments, the subject is a person who is predisposed to cancer, e.g. a person with a family history of cancer. Women who have (i) certain inherited genes (e.g. mutated BRCA1 and/or mutated BRCA2), (ii) been taking estrogen alone (without progesterone) after menopause for many years (at least 5, at least 7, or at least 10), and/or (iii) been taking fertility drug clomiphene citrate, are at a higher risk of contracting breast cancer. People who (i) consumes a diet high in salty and smoked foods and/or low in fruits and vegetables, (ii) had infection with *Helicobacter pylori*, and/or (iii) long-term stomach inflammation are at a higher risk of contracting stomach cancer. People who (i) had chemotherapy and radiation therapy for other cancers, (ii) has genetic disorders, such as Down syndrome, and/or (iii) exposure to certain chemicals, such as benzene are at a higher risk of contracting leukemia. People who (i) had inflammatory bowel disease, or a genetic syndrome such as familial adenomatous polyposis (FAP) and hereditary non-polyposis colorectal cancer (Lynch syndrome), and/or (ii) consumes a low-fiber and high-fat diet are at a higher risk of contracting colon cancer.

In another embodiment, the subject refers to a cancer patient who has been previously administered and/or treated with a tubulin binding drug such as paclitaxel, epothilone, docetaxel, discodermolide, etoposide, vinblastine, vincristine, teniposide, vinorelbine, and vindesine, and developed resistance to the tubulin binding drug. In another embodiment, the subject refers to a cancer patient who has been previously treated and/or administered with a tyrosine-kinase inhibitor such as imatinib, nilotinib, dasatinib, bosutinib, ponatinib, and bafetinib, and developed drug resistance via (i) Bcr-Abl dependent mechanisms involving Bcr-Abl duplication, Bcr-Abl mutation, T315I mutation, and/or P-loop mutations, or (ii) Bcr-Abl Independent mechanisms involving drug efflux caused by P-glycoproteins, drug import by organic cation transporter 1, and/or alternative signaling pathway activation. In at least one embodiment, the subject has leukemia, stomach, colon, and/or breast cancer and is currently undergoing, or has completed a tubulin inhibitor based and/or tyrosine-kinase inhibitor based chemotherapy regimen.

The terms "administer", "administering", "administration", and the like, as used herein, refer to the methods that may be used to enable delivery of the active ingredient and/or the composition to the desired site of biological action. Routes or modes of administration are as set forth herein. These methods include, but are not limited to, oral routes, intraduodenal routes, parenteral injection (including intravenous, subcutaneous, intraperitoneal, intramuscular, intravascular, or infusion), topical and rectal administration. Those of ordinary skill in the art are familiar with administration techniques that can be employed with the complexes and methods described herein. In a preferred embodiment, the active ingredient and/or the pharmaceutical composition described herein are administered orally.

In one or more embodiments, the pharmaceutical composition administered comprises the compound of formula (I), or a salt thereof, a solvate thereof, a tautomer thereof, a stereoisomer thereof, or a mixture thereof, in which $R_1$ is selected from the group consisting of phenyl, p-methoxyphenyl, p-fluorophenyl, and 2-furanyl, $R_2$ is selected from the group consisting of methyl, ethyl, phenyl, p-aminophenyl, p-chlorophenyl, m-chlorophenyl, m-fluorophenyl, p-methylphenyl,

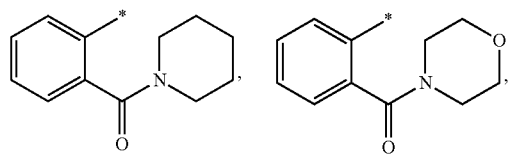

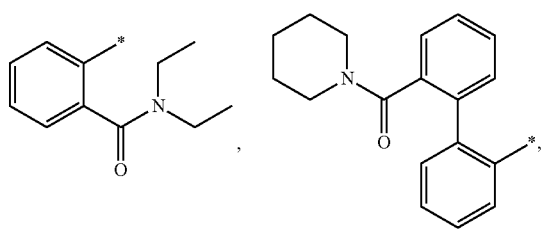

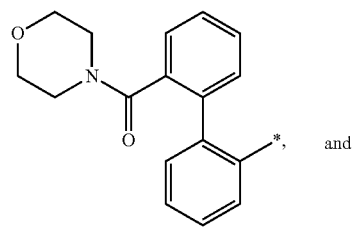

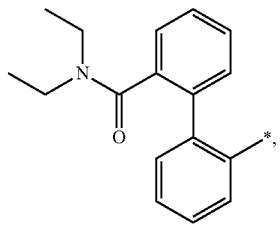

A is .—C(O)—., and n is 1. In most preferred embodiments, the pharmaceutical composition administered comprises a compound which is selected from the group consisting of

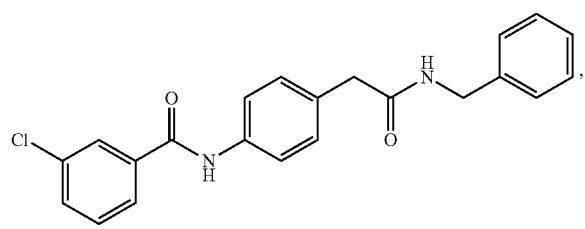

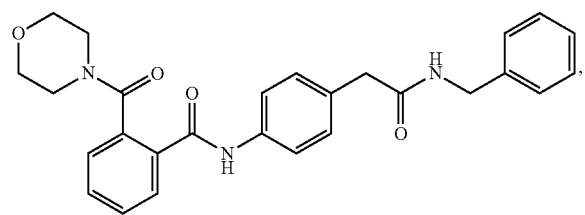

-continued

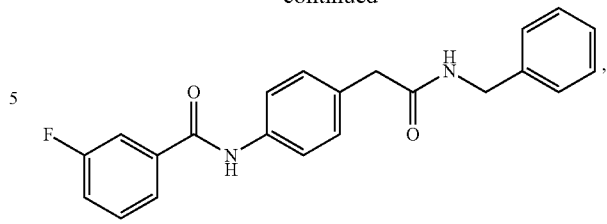

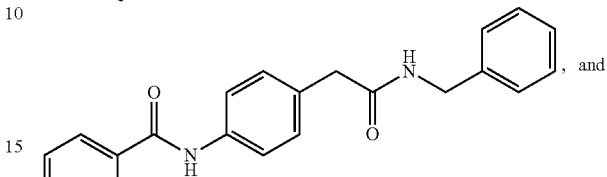

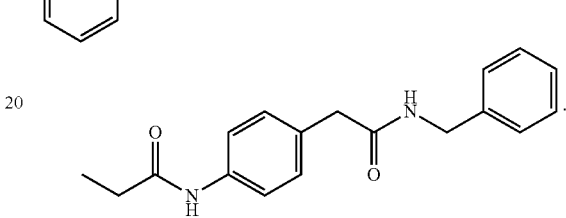

The dosage amount and treatment duration are dependent on factors, such as bioavailability of a drug, administration mode, toxicity of a drug, gender, age, lifestyle, body weight, the use of other drugs and dietary supplements, the disease stage, tolerance and resistance of the body to the administered drug, etc., and then determined and adjusted accordingly. The terms "effective amount", "therapeutically effective amount", or "pharmaceutically effective amount" refer to that amount of the active ingredient being administered which will relieve to some extent one or more of the symptoms of the disease being treated. The result can be a reduction and/or alleviation of the signs, symptoms, or causes of a disease, or any other desired alteration of a biological system. An appropriate "effective amount" may differ from one individual to another. An appropriate "effective amount" in any individual case may be determined using techniques, such as a dose escalation study. In one or more embodiments, an effective amount of the compound of formula (I) in a range of 0.1-200 mg/kg, preferably 1-100 mg/kg, more preferably 10-50 mg/kg is administered per body weight of the subject. However, in certain embodiments, the effective amount of the compound of formula (I) is less than 0.1 mg/kg or greater than 200 mg/kg.

In treating certain cancers, the best approach is often a combination of surgery, radiotherapy, and/or chemotherapy. Therefore, in at least one embodiment, the pharmaceutical composition is employed in conjunction with radiotherapy. In another embodiment, the pharmaceutical composition is employed with surgery. The radiotherapy and/or surgery may be performed before or after the pharmaceutical composition is administered.

A treatment method may comprise administering a pharmaceutical composition containing the compound of formula (I) of the current disclosure in any of its embodiments as a single dose or multiple individual divided doses. In some embodiments, the composition is administered at various dosages (e.g. a first dose with an effective amount of 200 mg/kg and a second dose with an effective amount of 50 mg/kg). In some embodiments, the interval of time between the administration of the composition and the administration of one or more additional therapies may be about 1-5 minutes, 1-30 minutes, 30 minutes to 60 minutes, 1 hour, 1-2 hours, 2-6 hours, 2-12 hours, 12-24 hours, 1-2 days, 2 days, 3 days, 4 days, 5 days, 6 days, 7 days, 1 week, 2 weeks, 3 weeks, 4 weeks, 5 weeks, 6 weeks, 7 weeks, 8 weeks, 9 weeks, 10 weeks, 15 weeks, 20 weeks, 26 weeks, 52 weeks, 11-15 weeks, 15-20 weeks, 20-30 weeks, 30-40 weeks, 40-50 weeks, 1 month, 2 months, 3 months, 4 months, 5 months, 6 months, 7 months, 8 months, 9 months, 10 months, 11 months, 12 months, 1 year, 2 years, or any period of time in between. Preferably, the composition is administered once daily for at least 2 days, at least 5 days, at least 6 days, or at least 7 days. In certain embodiments, the composition and one or more additional therapies are administered less than 1 day, less than 1 week, less than 2 weeks, less than 3 weeks, less than 4 weeks, less than 1 month, less than 2 months, less than 3 months, less than 6 months, less than 1 year, less than 2 years, or less than 5 years apart.

The methods for treating cancer and other proliferative disorders described herein inhibit, remove, eradicate, reduce, regress, diminish, arrest or stabilize a cancerous tumor, including at least one of the tumor growth, tumor cell viability, tumor cell division and proliferation, tumor metabolism, blood flow to the tumor and metastasis of the tumor. In some embodiments, the size of a tumor, whether by volume, weight or diameter, is reduced after the treatment by at least 5%, at least 10%, at least 15%, at least 20%, at least 25%, at least 30%, at least 40%, at least 50%, at least 60%, at least 70%, at least 75%, at least 80%, at least 85%, at least 90%, at least 95%, at least 99%, or 100%, relative to the tumor size before treatment. In other embodiments, the size of a tumor after treatment does not reduce but is maintained the same as the tumor size before treatment. Methods of assessing tumor size include, but are not limited to, CT scan, MRI, DCE-MRI and PET scan.

In one embodiment, the method disclosed herein may reduce the number of abnormal peripheral blood mononuclear cells in a leukemia patient, who may be afflicted with acute lymphoblastic leukemia (ALL), acute myeloid leukemia (AML), chronic lymphocytic leukemia (CLL), or chronic myeloid leukemia (CIVIL). Preferably, the number of abnormal peripheral blood mononuclear cells is reduced after the treatment by at least 5%, at least 10%, at least 20%, at least 30%, or at least 40%, and up to 100%, up to 99%, up to 95%, up to 90%, up to 80%, or up to 60%, relative to an initial number of abnormal peripheral blood mononuclear cells before treatment.

In most embodiments, the method further comprises measuring a concentration of a biomarker and/or detecting a mutation in a biomarker before and/or after the pharmaceutical composition comprising the compound of formula (I) of the present disclosure is administered. As used herein, the term "biomarker" refers to a characteristic that is objectively measured and evaluated as an indicator of normal biological processes, pathogenic processes or pharmacological responses to a therapeutic intervention. Generic cancer biomarkers include circulating tumor DNA (ctDNA) and circulating tumor cells (CTC). Exemplary biomarkers for colon cancer include, without limitation, carcinoembryonic antigen (CEA), carbohydrate antigen 242 (CA 242), CA 195, CA 19-9, MSI, and 18qLOH. Exemplary biomarkers for breast cancer include, without limitation, BRCA1, BRCA2, HER-2, estrogen receptor, progesterone receptor, cancer antigen 15-3, cancer antigen 27.29, carcinoembryonic antigen, Ki67, cyclin D1, cyclin E, and ERβ. Exemplary biomarkers for stomach cancer include, without limitation, carcinoembryonic antigen (CEA), CA19-9, carbohydrate antigen (CA) 72-4, alpha-fetoprotein, carbohydrate antigen (CA)12-5, SLE, BCA-225, hCG, and pepsinogenI/II. In one embodiment, leukemia patient's response to the treatment may be monitored by (i) measuring the complete blood count, (ii) observing the disappearance/reduction in occurrences of abnormal cytogenetic markers detected at the time of diagnosis, and/or (iii) observing the disappearance/reduction in occurrences of BCR/ABL mutational copies detected at the time of diagnosis.

Potentially predictive cancer biomarkers include, without limitation, mutations in genes BRCA1 and BRCA2 for breast cancer, overexpressions of TYMS, mutations in genes p53 and KRAS for colon cancer, and high concentration levels of AFP, and overexpressions of HSP90a for liver cancer.

The mutation in the biomarker may be detected by procedures such as restriction fragment length polymorphism (RFLP), polymerase chain reaction (PCR) assay, multiplex ligation-dependent probe amplification (MLPA), denaturing gradient gel electrophoresis (DGGE), single-strand conformation polymorphism (SSCP), hetero-duplex analysis, protein truncation test (PTT), and oligonucleotide ligation assay (OLA). The procedures to detect the mutation are well-known to those of ordinary skill in the art.

The term "sample" used herein refers to any biological sample obtained from the subject in need of therapy including a single cell, multiple cells, fragments of cells, a tissue sample, and/or body fluid. Specifically, the biological sample may include red blood cells, white blood cells, platelets, hepatocytes, epithelial cells, endothelial cells, a skin biopsy, a mucosa biopsy, an aliquot of urine, saliva, whole blood, serum, plasma, lymph. In some embodiments, the biological sample is taken from a tumor.

The concentration level of the cancer biomarker in a sample may be measured by an assay, for example an immunoassay. Typical immunoassay methods include, without limitation, enzyme-linked immunosorbent assay (ELISA), enzyme-linked immunospot assay (ELISPOT), Western blotting, immunohistochemistry (IHC), immunocytochemistry, immunostaining, and multiple reaction monitoring (MRM) based mass spectrometric immunoassay. The protocol for measuring the concentration of the biomarker and/or detecting the mutation in the biomarker is known to those of ordinary skill, for example by performing the steps outlined in the commercially available assay kit sold by Sigma-Aldrich, Thermo Fisher Scientific, R & D Systems, ZeptoMetrix Inc., Cayman Inc., Abcam, Trevigen, Dojindo Molecular Technologies, Biovision, and Enzo Life Sciences.

In some embodiments, a concentration of the biomarker is measured before and after the administration. When the concentration of the biomarker is maintained, the method may further comprise increasing the effective amount of the compound of formula (I) by at least 5%, at least 10%, or at least 30%, up to 50%, up to 60%, or up to 80% of an initial effective amount that is in a range of 0.1-200 mg/kg per body weight of the subject. The increased effective amount may be in a range of 0.105-360 mg/kg, preferably 1-300 mg/kg, more preferably 10-200 mg/kg. The subject may be administered with the increased dosage for a longer period (e.g. 1 week more, 2 weeks more, or 2 months more) than the duration prescribed with the initial effective amount.

In some embodiments, the mutation in the biomarker is detected before administering the composition to identify subjects predisposed to the disease. Alternatively, the biomarkers are measured/detected after each administration. For example, the measurement may be 1-5 minutes, 1-30 minutes, 30-60 minutes, 1-2 hours, 2-12 hours, 12-24 hours, 1-2 days, 1-15 weeks, 15-20 weeks, 20-30 weeks, 30-40 weeks, 40-50 weeks, 1 year, 2 years, or any period of time in between after the administration.

In some embodiments, the administration is stopped once the subject is treated.

The examples below are intended to further illustrate protocols for preparing and characterizing the compounds of formula (I), and uses thereof, and are not intended to limit the scope of the claims.

Example 1

Chemical Synthesis: Experimental

All melting points were uncorrected and measured using the capillary melting point instrument BI 9100 (Barnstead Electrothermal, UK). Infrared spectra were recorded on a Thermo Scientific Niccolet iS10 FT-IR Spectrometer (King Fand Center for Medical Research, King Abdulaziz University, Jeddah, Saudi Arabia). In this disclosure, only characteristic IR stretching bands are listed, such as NH, OH, CH, C=O, C=N and/or C=C. In FT-IR, all samples were measured neat. $^1$H NMR spectra were recorded on an AVANCE-III 600 MHz and AVANCE-III HD 850 MHz spectrometers (Bruker, Germany), and chemical shifts were expressed as ppm against TMS as an internal reference (King Fand Center for Medical Research and Faculty of Science, King Abdulaziz University, Jeddah, Saudi Arabia). LC/MS analyses were performed on an Agilent 6320 Ion Trap HPLC-ESI-MS/DAD (Santa Clara, Calif., USA) with the following settings. The analytes were separated using a Macherey-Nagel Nucleodur-C18 column (150 mm length× 4.6 mm i.d., 5 µm) (Macherey-Nagel GMBH & Co. KG, Duren, Germany). Mobile phase isocratic elution using a mixture of acetonitrile and 0.01 formic acid in water (80:20, v/v). The flow rate was 0.4 mL/min, and total run time=20 min. Purities were reported according to percentage of Peak Areas at wavelength of 280 nm. High-resolution mass spectrometry (HRMS) was performed in the Faculty of Science, King Abdulaziz University on Impact II™ Q-TOF spectrometer (Bruker, Germany). Column chromatography was performed on a silica gel 60 (particle size 0.06 mm-0.20 mm).

Figure 4:
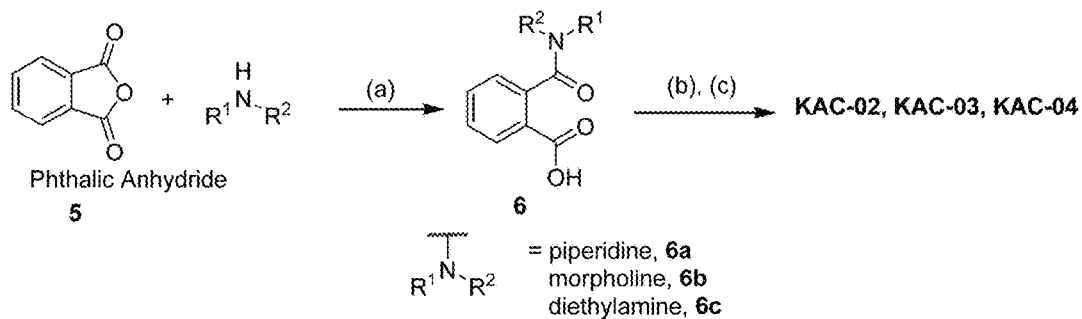
FIG. 4 is a scheme illustrating the synthesis of starting materials 6a, 6b, and 6c as well as KAC compounds KAC-02, KAC-03, and KAC-04.
Figure 5:
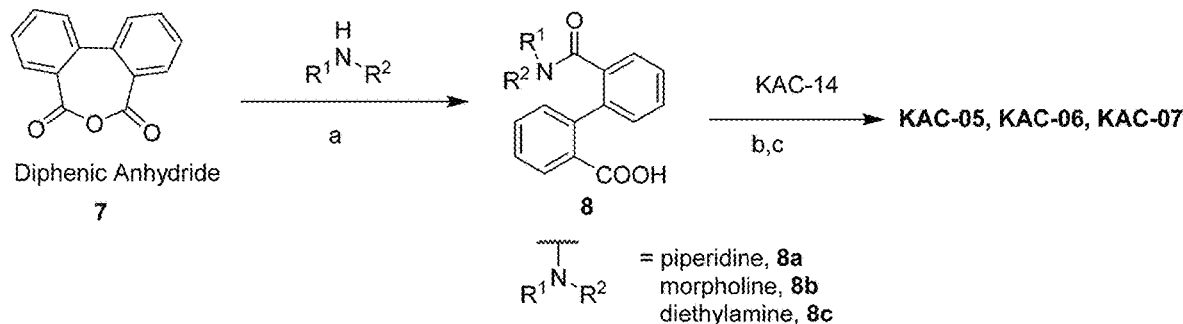
FIG. 5 is a scheme illustrating the synthesis of starting materials 8a, 8b, and 8c as well as KAC compounds KAC-05, KAC-06, and KAC-07.
Figure 6:
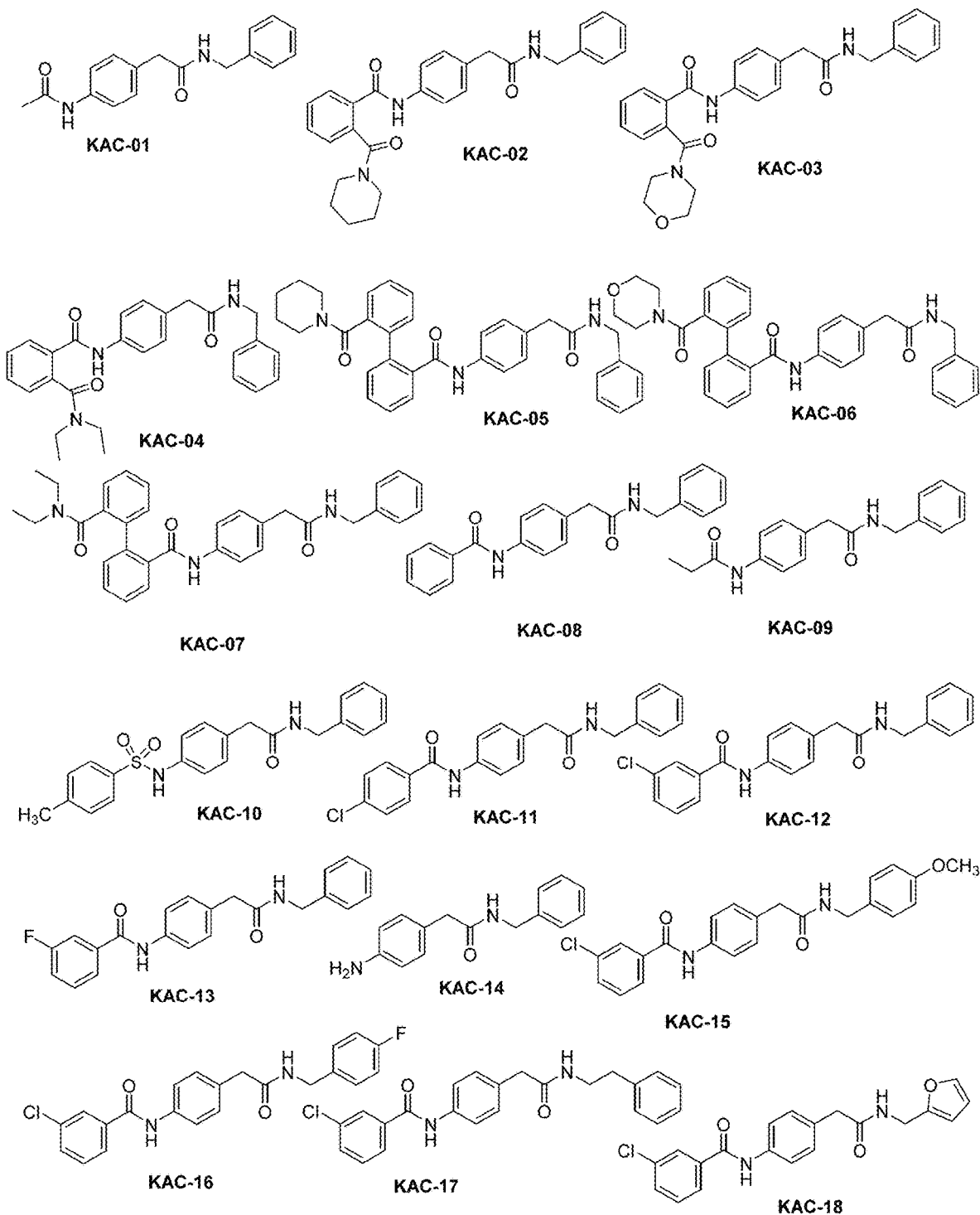
FIG. 6 shows a list of KAC compounds.
Figure 7A:
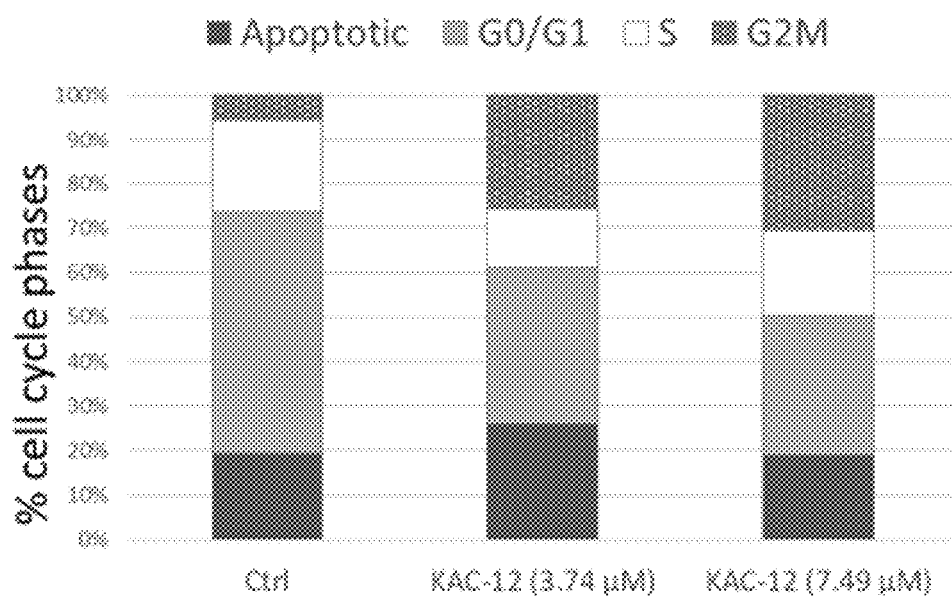
FIG. 7A is a bar graph summarizing the effect of KAC-12 on different cell cycle stages of HL-60 cells.
Figure 7B:
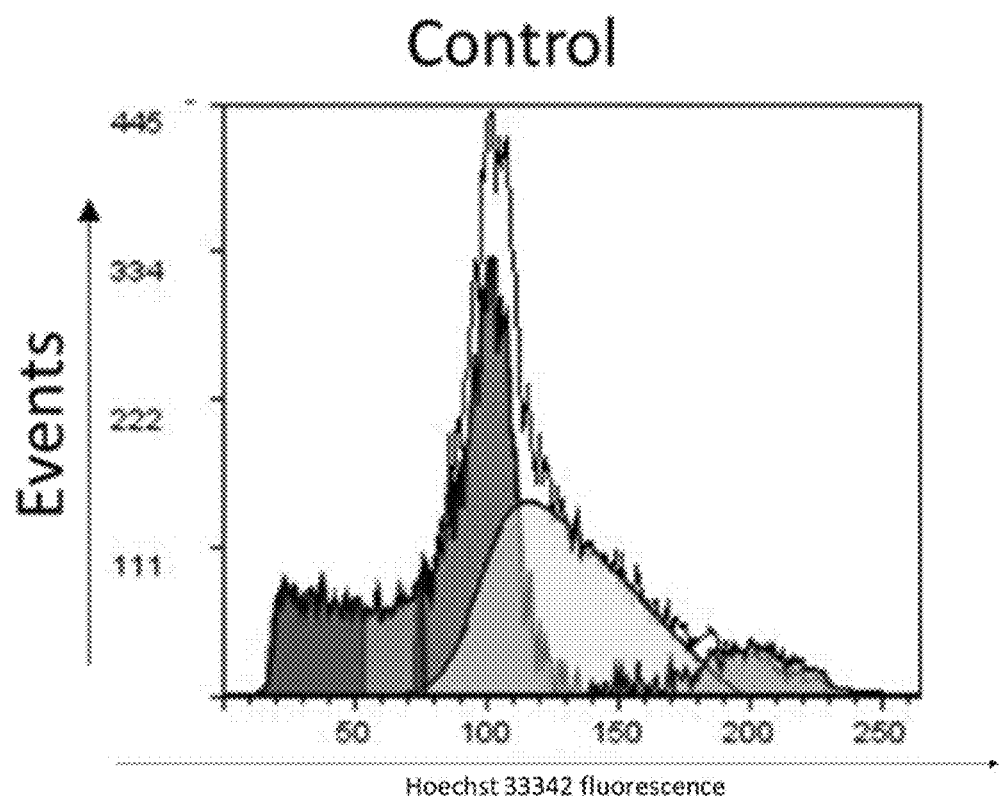
FIG. 7B shows different cell cycle stages of HL-60 cells upon treatment of blank control (in the absence of KAC-12).
Figure 7C:
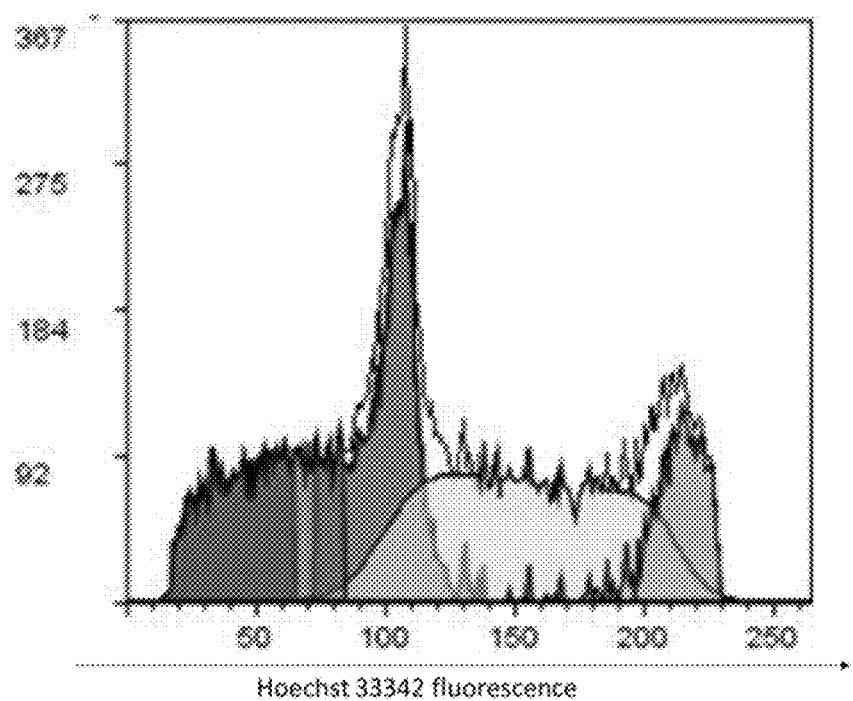
FIG. 7C shows different cell cycle stages of HL-60 cells upon treatment of KAC-12 at a concentration of 3.74 µM.
Figure 7D:
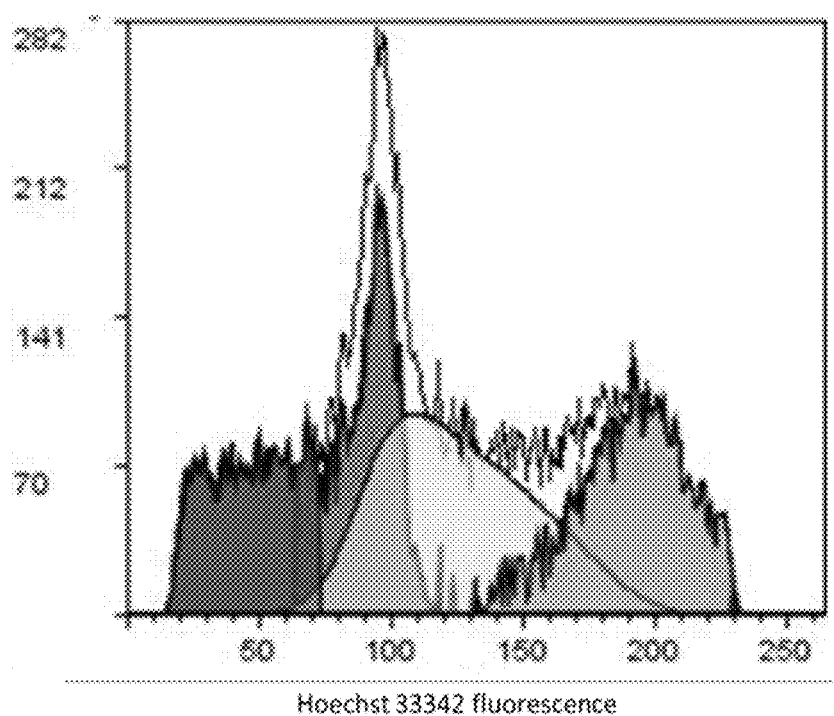
FIG. 7D shows different cell cycle stages of HL-60 cells upon treatment of KAC-12 at a concentration of 7.49 µM.
Figure 8A:
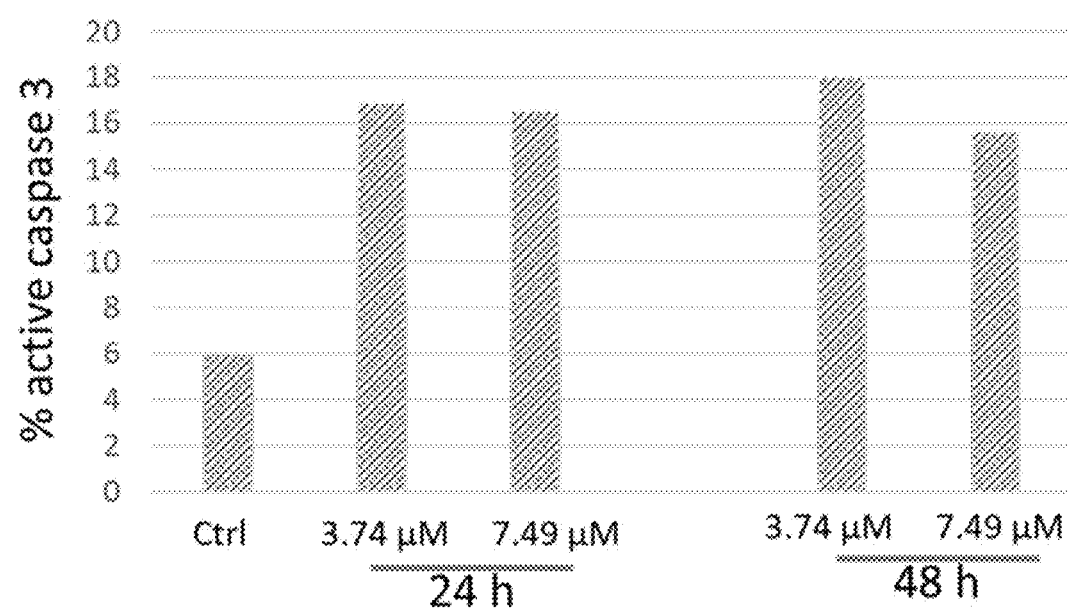
FIG. 8A is a bar graph summarizing the effect of KAC-12 on apoptosis in HL-60 cells.
Figure 8B:
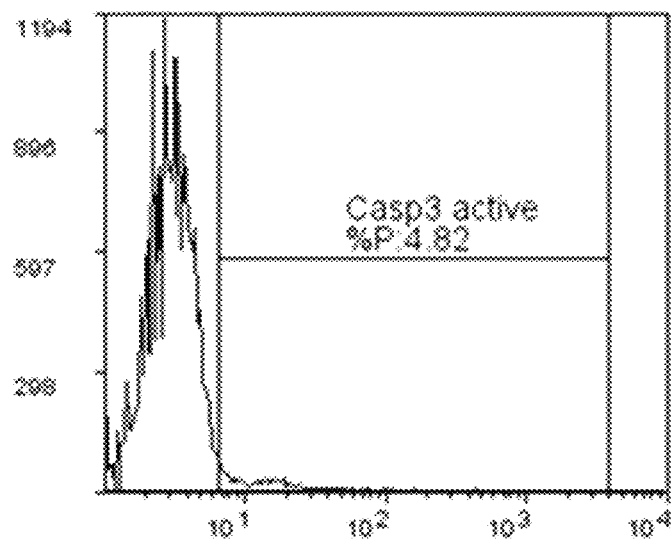
FIG. 8B is a histogram showing caspase-3 activity of HL-60 cells upon treatment of blank control (in the absence of KAC-12) for 24 hours.
Figure 8C:
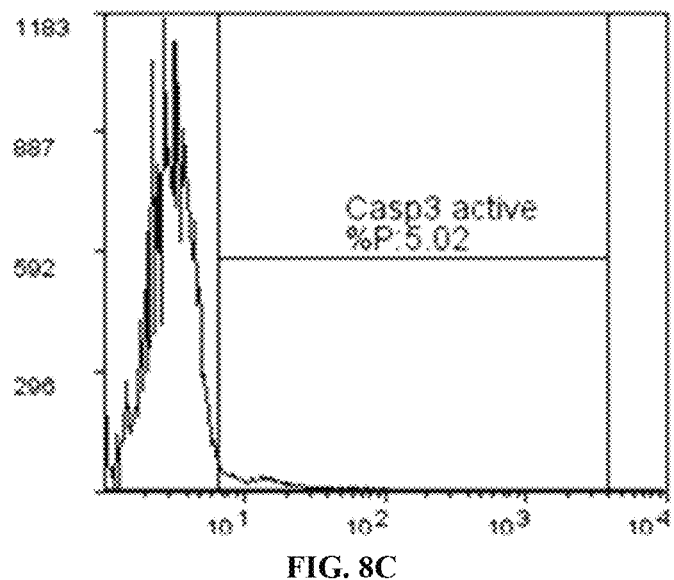
FIG. 8C is a histogram showing caspase-3 activity of HL-60 cells upon treatment of blank control (in the absence of KAC-12) for 48 hours.
Figure 8D:
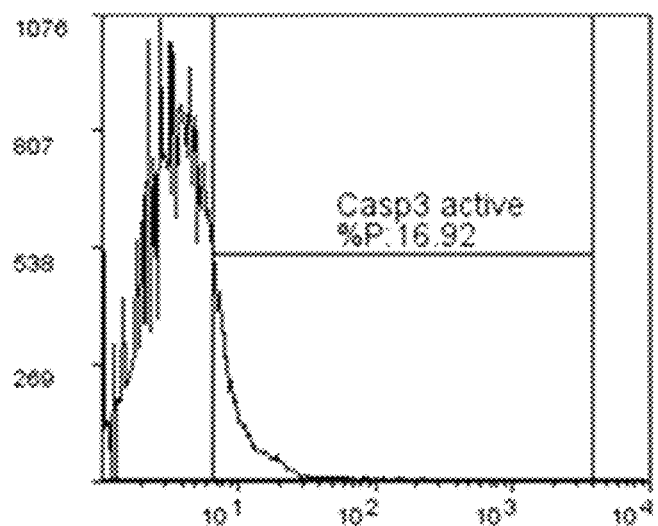
FIG. 8D is a histogram showing caspase-3 activity of HL-60 cells upon treatment of KAC-12 at a concentration of 3.74 µM for 24 hours.
Figure 8E:
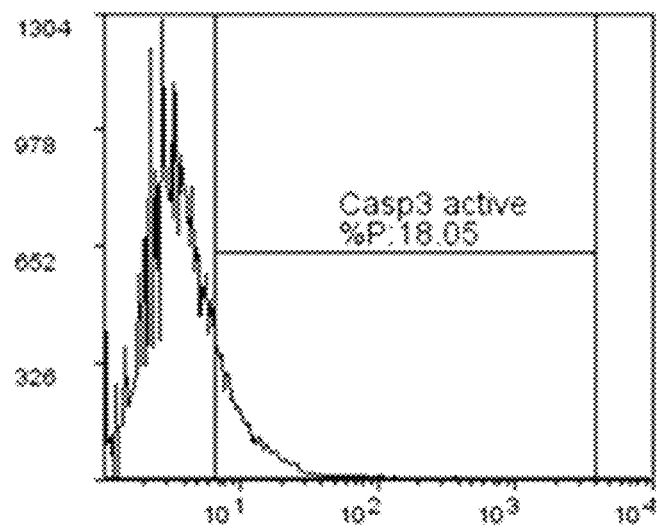
FIG. 8E is a histogram showing caspase-3 activity of HL-60 cells upon treatment of KAC-12 at a concentration of 3.74 µM for 48 hours.
Figure 8F:
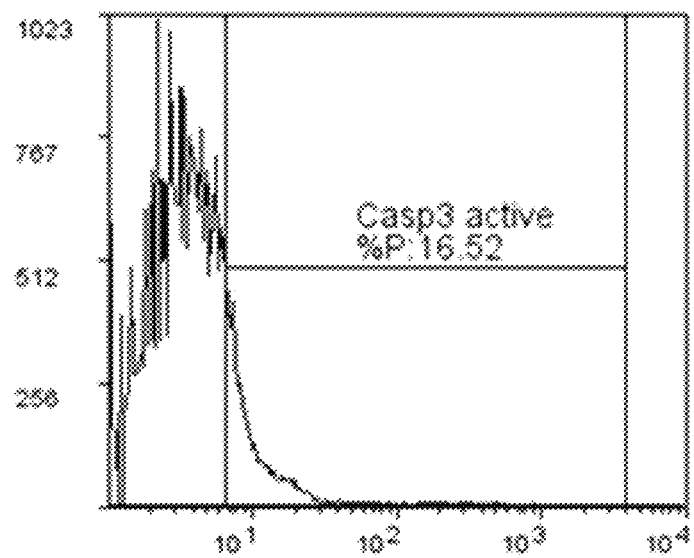
FIG. 8F is a histogram showing caspase-3 activity of HL-60 cells upon treatment of KAC-12 at a concentration of 7.49 µM for 24 hours.
Figure 8G:
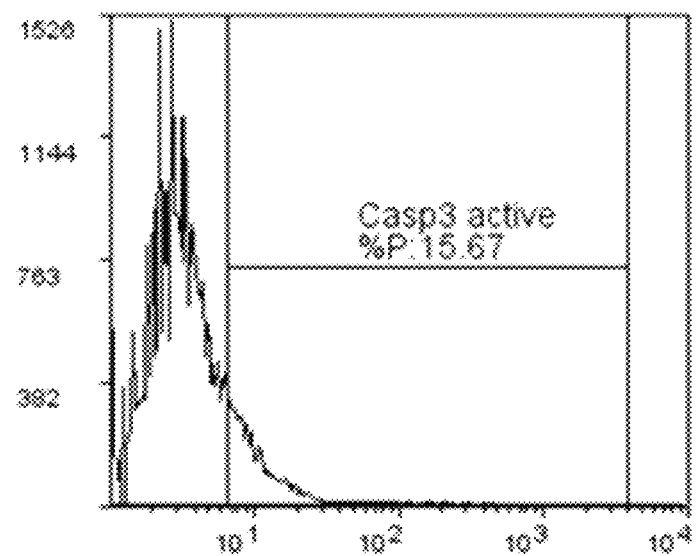
FIG. 8G is a histogram showing caspase-3 activity of HL-60 cells upon treatment of KAC-12 at a concentration of 7.49 µM for 48 hours.

KAC-14 (intermediate) [Kumar, M.; Sharma, S.; Thakur, K.; Nayal, O. S.; Bhatt, V.; Thakur, M. S.; Kumar, N.; Singh, B.; Sharma, U., Montmorillonite-K10-Catalyzed Microwave-Assisted Direct Amidation of Unactivated Carboxylic Acids with Amines: Maintaining Chiral Integrity of Substrates. Asian J. Org. Chem. 2017, 6 (3), 342-346, incorporated herein by reference in its entirety] (see FIG. 3), 6a [Sato, I.; Morihira, K.; Inami, H.; Kubota, H.; Morokata, T.; Suzuki, K.; Iura, Y.; Nitta, A.; Imaoka, T.; Takahashi, T.; Takeuchi, M.; Ohta, M.; Tsukamoto, S.-i., Design and synthesis of 6-fluoro-2-naphthyl derivatives as novel CCR3 antagonists with reduced CYP2D6 inhibition. Bioorg. Med. Chem. 2008, 16 (18), 8607-8618, incorporated herein by reference in its entirety], 6b [Kumar, P. P.; Yervala, D. R.; Chittireddy, V. R. R.; Bhoomireddy, R. D.; Dubey, P. K., Synthesis of novel symmetrical and unsymmetrical o-phthalic acid diamides. Org. Chem. Int. 2014, 576715/1-576715/10, 10 pp, incorporated herein by reference in its entirety] (see FIG. 4), 8a [Jenkins, G. L.; Davis, C. S.; Knevel, A. M.; Yoder, D. S., Synthesis of amides of diphenic acid as potential antispasmodic agents. J. Pharm. Sci. 1963, 52 (9), 902-3, incorporated herein by reference in its entirety], 8b [Aboul-Enein, H. Y.; Ibrahim, S. E.; Khalifa, M., Synthesis and biological activity of dibenz[c,e]azepines. Drug Des. Delivery 1988, 4 (1), 27-33, incorporated herein by reference in its entirety], and 8c [Boyd, G. V.; Monteil, R. L., Synthesis and reactions of cyclic isoimidium salts. J. Chem. Soc., Perkin Trans. 1 1978, (11), 1338-50, incorporated herein by reference in its entirety] (see FIG. 5) were prepared and structurally confirmed, as compared to literature [Kumar, M.; Sharma, S.; Thakur, K.; Nayal, O. S.; Bhatt, V.; Thakur, M. S.; Kumar, N.; Singh, B.; Sharma, U., Montmorillonite-K10-Catalyzed Microwave-Assisted Direct Amidation of Unactivated Carboxylic Acids with Amines: Maintaining Chiral Integrity of Substrates. Asian J. Org. Chem. 2017, 6 (3), 342-346].

Example 2

2-(4-aminophenyl)-N-benzylacetamide (KAC-14)

[Kumar, M.; Sharma, S.; Thakur, K.; Nayal, O. S.; Bhatt, V.; Thakur, M. S.; Kumar, N.; Singh, B.; Sharma, U., Montmorillonite-K10-Catalyzed Microwave-Assisted Direct Amidation of Unactivated Carboxylic Acids with Amines: Maintaining Chiral Integrity of Substrates. Asian J. Org. Chem. 2017, 6 (3), 342-346, incorporated herein by reference in its entirety]

A mixture of 2-(4-nitrophenyl)acetic acid (10 mmol, 1.81 g) and 50 mL dichloromethane (DCM) was placed in a dry 3-neck round bottom flask and flushed with nitrogen which was then stirred in an ice bath. Then, oxalyl chloride (11.6 mmol, 1.48 g, 1 mL) with 5 mL DCM were placed in an additional funnel and were then fast-dropped to the original mixture. After completing the addition of oxalyl chloride, 1 drop from dimethylformamide (DMF) were added, and later, after 15 min, the ice bath was removed and the mixture was stirred at room temperature (r.t.) and the stirring continued for 4 hrs as all the acid completely dissolved. The solvent was removed using rotary evaporator and the residue 2-(4-nitrophenyl)acetyl chloride was dissolved in 40 mL DCM and was stirred for 10 min in an ice bath. Using an additional funnel, benzyl amine (10 mmol, 1.1 g, 1.1 mL) and Diisopropylethylamine (DIPEA) (10 mmol, 1.55 g, 2.1 mL) in 10 mL DCM were added drop wise to the acid chloride. After the ice melted, the stirring continued over night at room temperature. The solid particles were removed by filtration, washed in a small amount of DCM to form a yellowish white crystalline solid (1.14 g). The completion of the reaction was checked by TLC for both the solid and filtrate using ethyl acetate hexane mixture in the ratio 1:1 against the starting materials. The filtrate was neutralized by dil. HCl and the organic layer was collected, dried using sodium sulphate, the solvent was rotavaped and the solid was collected and washed with Ether. In a 150 mL round bottom flask rapped with Aluminum foil, N-benzyl-2-(4-nitrophenyl)acetamide (6.58 mmol, 1.78 g), SnCl$_2$ dihydrate (26.34 mmol, 5.95 g), ethyl acetate (40 mL), and water (0.5 mL) were refluxed for 4 hrs. The mixture was cooled and diluted by ethyl acetate (40 mL) and then treated with a cold 40% NaOH solution (80 mL). Then fresh water was added to break an emulsion formed. The organic layer was separated then the aqueous layer was washed with 10 mL of ethyl acetate then the combined organic layers were washed with 15 mL of brine and dried with magnesium sulphate. The ethyl acetate was distilled off using the rotary evaporator and the solid product was collected. The yield: 1.55 g (98.7%) and melting point is 140-142° C. The compound was used for the next step without further characterization.

Example 3

2-(4-acetamidophenyl)-N-benzylacetamide (KAC-01)

[Miltsov, S.; Karavan, V.; Misharev, A.; Alonso-Chamarro, J.; Puyol, M., Boron trifluoride-methanol complex. Mild and powerful reagent for deprotection of acetylated amines. Scope and selectivity. *Tetrahedron Lett.* 2016, 57 (6), 641-644, incorporated herein by reference in its entirety]

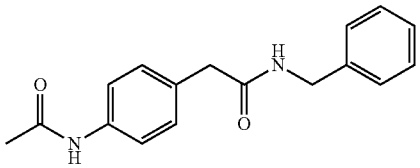 [SMILES: CC(=O)Nc1ccc(CC(=O)NCc2ccccc2)cc1]

In an ice bath, acetyl chloride was dissolved in 75 mL DCM and stirred for 10 min. 2-(4-aminophenyl)-N-benzylacetamide (KAC-14) (2 mmol, 0.48 g) and diisopropylethylamine (DIPEA) (10 mmol, 2.1 mL) in 25 mL DCM were added drop wise to the acetyl chloride using an addition funnel. After the ice melted, the stirring continued over night at room temperature. The completion of the reaction was checked by TLC for both the solid and filtrate using the ethyl acetate hexane mixture in the ratio 1:1 against starting materials. The mixture was neutralized by dil. HCl and the product was extracted with ethyl acetate. The organic layer was washed, collected, and dried using sodium sulfate. The solvent was rotavaped and the solid was collected and washed with ether. The product was purified by crystallization from hot methanol. Melting point of the final product is 175° C. $^1$H NMR (600 MHz, DMSO-$d_6$) δ ppm 9.92 (br. s., 1H), 8.51 (br. s., 1H), 7.50 (d, J=7.91 Hz, 2H), 7.28-7.36 (m, 2H), 7.16-7.27 (m, 4H), 4.23-4.31 (m, 2H), 3.42 (br. s., 2H), 2.04 (br. s., 3H).

Example 4

N-(4-(2-(benzylamino)-2-oxoethyl)phenyl)-2-(morpholine-4-carbonyl)benzamide (KAC-03)

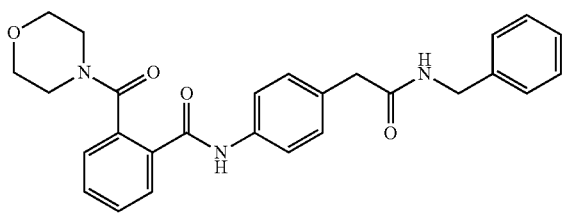 [SMILES: O=C(Cc1ccc(NC(=O)c2ccccc2C(=O)N2CCOCC2)cc1)NCc1ccccc1]

The starting material 6b (1 mmol) was placed in dichlomethane (6 mL) followed by equimolar amount of oxalyl chloride. The mixture was cooled to 0° C. in ice bath and stirred under inert atmosphere. A drop of N,N-dimethylformamide (DMF) was added and the mixture was stirred at room temp for 2 h. The mixture was concentrated by evaporation in vacuo at room temperature. The acid chloride was kept under nitrogen and added (drop-wise) to an icebath cooled mixture of amine KAC-14 and ethyl diisopropyl amine added (DIPEA, 2 equivalent) while stirring. The solvent was removed by vacuum evaporation and the residue was partitioned between ethyl acetate and 5% HCl, water and saturated NaHCO$_3$. The organic layer was dried, evaporated in vacuum and purified by crystallization from ethanol.

The product KAC-03 was white solid, mp 210° C. $^1$H NMR (600 MHz, DMSO-$d_6$) δ 8.63 (t, J=5.84 Hz, 1H), 8.47-8.57 (m, 1H), 7.96-8.02 (m, 1H), 7.89-7.96 (m, 1H), 7.64-7.70 (m, 3H), 7.57-7.64 (m, 3H), 7.43 (d, J=8.28 Hz, 1H), 7.39 (d, J=8.28 Hz, 1H), 7.30-7.37 (m, 2H), 7.19-7.30 (m, 5H), 4.24-4.35 (m, 3H), 3.57 (s, 1H), 3.43-3.50 (m, 2H); $^{13}$C NMR (151 MHz, DMSO-$d_6$) δ 169.1, 135.2, 133.3, 131.2, 129.9, 128.8, 128.8, 128.7, 127.7, 127.7, 123.9, 119.9, 42.4, 40.5.

Example 5

N-(4-(2-(benzylamino)-2-oxoethyl)phenyl)-2-(piperidine-1-carbonyl)benzamide (KAC-02)

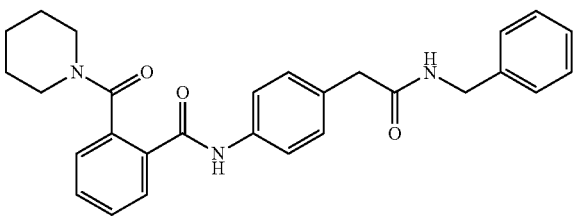 [SMILES: O=C(Cc1ccc(NC(=O)c2ccccc2C(=O)N2CCCCC2)cc1)NCc1ccccc1]

This compound was prepared according to the procedure described for the synthesis of KAC-03 using the starting material 6a (1 mmol) in dichloromethane. The product KAC-02 was collected as a white solid, mp 175° C. $^1$H NMR (600 MHz, DMSO-$d_6$) δ 8.51 (t, J=5.65 Hz, 1H), 7.87-7.99 (m, 7H), 7.55-7.59 (m, 1H), 7.48 (d, J=8.28 Hz, 1H), 7.36-7.44 (m, 1H), 7.20-7.36 (m, 7H), 7.12 (d, J=8.66 Hz, 1H), 4.89 (s, 1H), 4.44 (s, 1H), 4.33 (s, 1H), 2.10 (s, 1H), 1.37 (s, 1H), 1.20-1.32 (m, 3H), 1.12-1.20 (m, 1H).

Example 6

N$^1$-(4-(2-(benzylamino)-2-oxoethyl)phenyl)-N$^2$,N$^2$-diethylphthalamide (KAC-04)

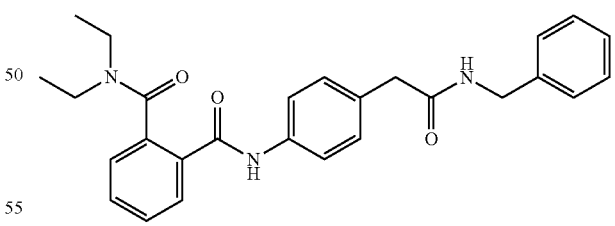

This compound was prepared according to the procedure described for the synthesis of KAC-03 using the starting material 6c. The product KAC-04 was white solid, mp 131° C. $^1$H NMR (600 MHz, DMSO-$d_6$) δ 10.29 (s, 1H), 8.50 (t, J=5.83 Hz, 1H), 7.73 (d, J=7.15 Hz, 1H), 7.62 (d, J=8.28 Hz, 2H), 7.57 (t, J=7.91 Hz, 1H), 7.53 (t, J=7.34 Hz, 1H), 7.29-7.35 (m, 3H), 7.24 (d, J=8.28 Hz, 5H), 4.28 (d, J=5.65 Hz, 2H), 3.45 (s, 2H), 3.40 (d, J=7.15 Hz, 2H), 3.14 (q, J=7.15 Hz, 2H), 1.10 (t, J=6.96 Hz, 3H), 1.04 (t, J=7.15 Hz, 3H).

Example 7

N-(4-(2-(benzylamino)-2-oxoethyl)phenyl)-2'-(piperidine-1-carbonyl)-[1,1'-biphenyl]-2-carboxamide (KAC-05)

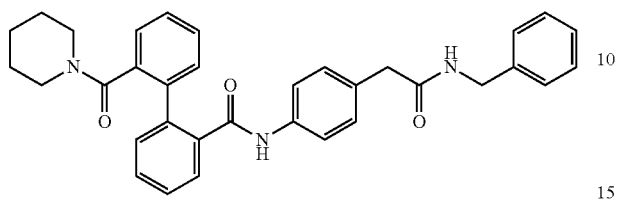

This compound was prepared according to the procedure described for the synthesis of KAC-03 using the starting material 8a. The product KAC-05 was white solid, mp 175° C. $^1$H NMR (600 MHz, DMSO-d$_6$) δ 8.67 (br. s., 2H), 8.20 (d, J=8.28 Hz, 4H), 7.50-7.65 (m, 4H), 7.38-7.43 (m, 1H), 7.29-7.36 (m, 4H), 7.22-7.28 (m, 6H), 4.29 (d, J=5.65 Hz, 4H), 3.68 (s, 4H), 1.37 (br. s., 1H).

Example 8

N-(4-(2-(benzylamino)-2-oxoethyl)phenyl)-2'-(morpholine-4-carbonyl)-[1,1'-biphenyl]-2-carboxamide (KAC-06)

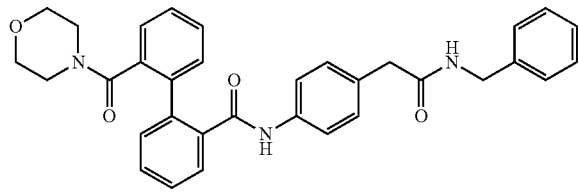 [SMILES: O=C(Cc1ccc(NC(=O)c2ccccc2-c2ccccc2C(=O)N2CCOCC2)cc1)NCc1ccccc1]

This compound was prepared according to the procedure described for the synthesis of KAC-03 using the starting material 8b. The product KAC-06 was white solid, mp 185° C. $^1$H NMR (600 MHz, DMSO-d$_6$) δ 10.49 (br. s., 1H), 8.49 (br. s., 1H), 7.66 (br. s., 1H), 7.51-7.60 (m, 3H), 7.38 (br. s., 5H), 7.30 (s, 4H), 7.22 (s, 5H), 7.14 (br. s., 2H), 4.26 (s, 3H), 3.39 (d, J=6.78 Hz, 3H); $^{13}$C NMR (151 MHz, DMSO-d$_6$) δ 170.6, 137.9, 129.7, 128.9, 128.7, 128.6, 127.7, 127.2, 66.7, 42.6, 42.2, 40.5.

Example 9

N$^2$-(4-(2-(benzylamino)-2-oxoethyl)phenyl)-N$^{2'}$,N$^{2'}$-diethyl-[1,1'-biphenyl]-2,2'-dicarboxamide (KAC-07)

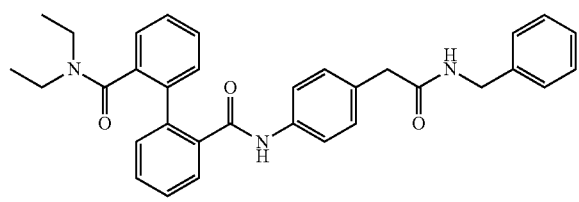 [SMILES: CCN(CC)C(=O)c1ccccc1-c1ccccc1C(=O)Nc1ccc(CC(=O)NCc2ccccc2)cc1]

This compound was prepared according to the procedure described for the synthesis of KAC-03 using the starting material 8c. The product KAC-07 was white solid, mp 163° C. $^1$H NMR (600 MHz, DMSO-d$_6$) δ 10.48 (s, 1H), 8.48 (t, J=5.65 Hz, 1H), 7.60-7.66 (m, 1H), 7.47-7.52 (m, 3H), 7.35-7.43 (m, 3H), 7.28-7.34 (m, 4H), 7.19-7.27 (m, 7H), 7.11 (d, J=7.91 Hz, 2H), 4.24 (s, 3H), 0.82 (s, 4H).

Example 10

N-(4-(2-(benzylamino)-2-oxoethyl)phenyl)benzamide (KAC-08)

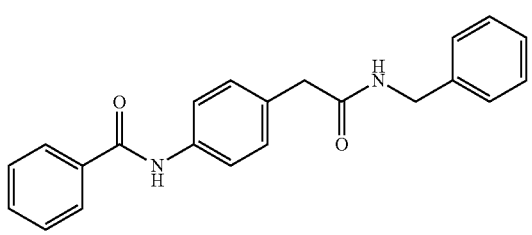 [SMILES: O=C(Cc1ccc(NC(=O)c2ccccc2)cc1)NCc1ccccc1]

This compound KAC-08 was prepared according to the procedure described for the synthesis of KAC-01. The compound was white solid, mp 212° C. (dec.). $^1$H NMR (850 MHz, DMSO-d$_6$) δ 10.23 (s, 1H), 8.55 (t, J=5.71 Hz, 1H), 7.95 (d, J=6.75 Hz, 2H), 7.67-7.71 (m, J=8.30 Hz, 2H), 7.59 (t, J=7.53 Hz, 1H), 7.53 (t, J=7.53 Hz, 2H), 7.29-7.34 (m, 2H), 7.25-7.27 (m, J=8.30 Hz, 2H), 7.22-7.25 (m, 3H), 4.27 (d, J=5.71 Hz, 2H). $^{13}$C NMR (214 MHz, DMSO-d$_6$) δ 170.8, 166.0, 139.9, 138.0, 135.4, 132.2, 132.0, 129.6, 128.9, 128.8, 128.1, 127.7, 127.3, 120.8, 42.7, 42.3.

Example 11

N-(4-(2-(benzylamino)-2-oxoethyl)phenyl)propionamide (KAC-09)

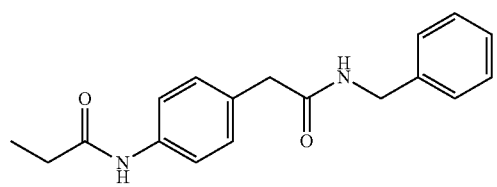 [SMILES: CCC(=O)Nc1ccc(CC(=O)NCc2ccccc2)cc1]

This compound was prepared according to the procedure described for the synthesis of KAC-01. The compound was white solid, mp 210° C. $^1$H NMR (850 MHz, DMSO-d$_6$) δ 9.83 (s, 1H), 8.51 (br. s., 1H), 7.50 (d, J=7.78 Hz, 1H), 7.27-7.33 (m, 2H), 7.20-7.26 (m, 3H), 7.18 (d, J=7.78 Hz, 2H), 4.26 (d, J=5.71 Hz, 2H), 3.41 (s., 2H), 2.30 (q, J=7.27 Hz, 2H), 1.07 (t, J=7.53 Hz, 2H). $^{13}$C NMR (214 MHz, DMSO-d$_6$) δ 172.4, 170.9, 139.9, 138.2, 131.3, 129.7, 128.7, 127.6, 127.2, 119.4, 42.6, 42.2, 29.9, 10.2.

Example 12

N-benzyl-2-(4-((4-methylphenyl)sulfonamido)phenyl)acetamide (KAC-10)

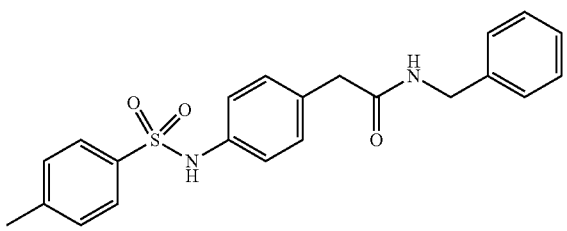 [SMILES: Cc1ccc(S(=O)(=O)Nc2ccc(CC(=O)NCc3ccccc3)cc2)cc1]

This compound was prepared according to the procedure described for the synthesis of KAC-01. The compound was white solid, mp 140° C. $^1$H NMR (850 MHz, DMSO-d$_6$) δ 8.49 (t, J=5.97 Hz, 1H), 7.63-7.65 (m, J=8.30 Hz, 2H), 7.32-7.34 (m, J=8.30 Hz, 2H), 7.27 (t, J=7.27 Hz, 2H), 7.22 (t, J=7.27 Hz, 1H), 7.17 (d, J=7.27 Hz, 2H), 7.09-7.12 (m, J=8.30 Hz, 2H), 6.98-7.01 (m, 2H), 4.22 (d, J=6.23 Hz, 2H), 3.35 (s, 2H), 2.33 (s, 3H). $^{13}$C NMR (214 MHz, DMSO-d$_6$) δ 170.6, 143.6, 139.8, 137.3, 136.8, 132.3, 130.1, 130.1, 128.7, 127.6, 127.2, 127.2, 120.4, 42.6, 42.0, 40.3, 40.2, 40.2, 40.1, 40.1, 40.0, 40.0, 39.9, 39.9, 39.8, 39.8, 39.7, 39.7, 39.6, 39.6, 21.4.

Example 13

N-(4-(2-(benzylamino)-2-oxoethyl)phenyl)-4-chlorobenzamide (KAC-11)

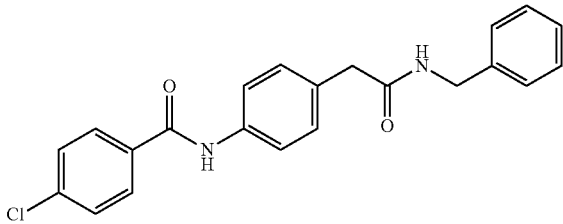 [SMILES: O=C(Cc1ccc(NC(=O)c2ccc(Cl)cc2)cc1)NCc1ccccc1]

This compound was prepared according to the procedure described for the synthesis of KAC-01. The compound KAC-11 was off-white solid mp >230° C.

Example 14

N-(4-(2-(benzylamino)-2-oxoethyl)phenyl)-4-chlorobenzamide (KAC-12)

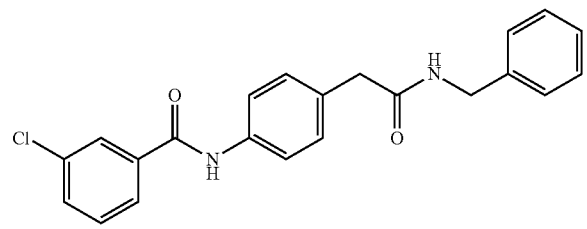 [SMILES: O=C(Cc1ccc(NC(=O)c2cccc(Cl)c2)cc1)NCc1ccccc1]

This compound was prepared according to the procedure described for the synthesis of KAC-01. The compound KAC-12 was white solid, mp 207° C. $^1$H NMR (850 MHz, DMSO-d$_6$) δ 10.34 (s, 1H), 8.56 (d, J=5.71 Hz, 1H), 8.02 (t, J=1.82 Hz, 1H), 7.93 (d, J=8.30 Hz, 1H), 7.68-7.71 (m, J=8.30 Hz, 2H), 7.66-7.68 (m, 1H), 7.57 (t, J=8.04 Hz, 1H), 7.30-7.33 (m, 2H), 7.26-7.28 (m, J=8.30 Hz, 2H), 7.24 (d, J=7.27 Hz, 2H), 4.28 (d, J=6.23 Hz, 2H), 3.47 (s, 2H); $^{13}$C NMR (214 MHz, DMSO-d$_6$) δ 170.7, 164.4, 139.9, 137.7, 137.4, 133.7, 132.5, 131.8, 130.9, 129.7, 128.8, 127.9, 127.7, 127.6, 127.2, 126.9, 120.9, 42.7, 42.3.

Example 15

N-(4-(2-(benzylamino)-2-oxoethyl)phenyl)-4-chlorobenzamide (KAC-13)

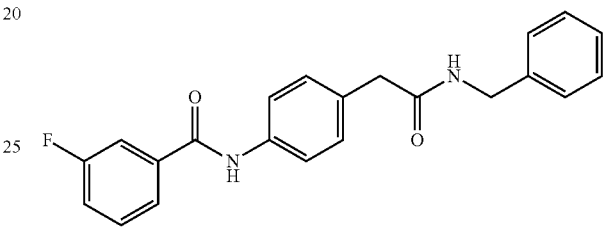

This compound was prepared according to the procedure described for the synthesis of KAC-01. mp 214° C. $^1$H NMR (850 MHz, DMSO-d$_6$) δ 10.30 (s, 1H), 8.55 (t, J=5.97 Hz, 1H), 7.81 (d, J=7.79 Hz, 1H), 7.76 (td, J=2.21, 9.60 Hz, 1H), 7.66-7.70 (m, J=8.30 Hz, 2H), 7.59 (dt, J=5.97, 7.91 Hz, 1H), 7.45 (dt, J=2.34, 8.69 Hz, 1H), 7.29-7.33 (m, 2H), 7.25-7.29 (m, J=8.30 Hz, 2H), 7.21-7.25 (m, 3H), 4.27 (d, J=5.71 Hz, 2H), 3.51 (br. s., 1H). $^{13}$C NMR (214 MHz, DMSO-d$_6$) δ 170.8, 164.5, 164.5, 163.0, 161.8, 139.9, 137.7, 137.6, 132.4, 131.1, 131.1, 129.7, 128.8, 127.7, 127.3, 124.3, 124.3, 120.9, 119.0, 118.9, 114.9, 114.8, 42.7, 42.3.

Example 16

3-Chloro-N-(4-(2-((4-methoxybenzyl)amino)-2-oxoethyl)phenyl)benzamide (KAC-15)

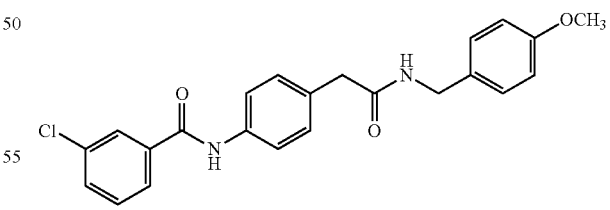

This compound was prepared by reacting KAC-14 with 3-chlorobenzoyl chloride according to the procedure described for the synthesis of KAC-1. mp 212° C. $^1$H NMR (850 MHz, DMSO-d$_6$) δ 10.32 (s, 1H), 8.46 (t, J=5.71 Hz, 1H), 8.01 (s, 1H), 7.89-7.93 (m, 3H), 7.66-7.72 (m, 4H), 7.54-7.59 (m, 2H), 7.26 (d, J=8.30 Hz, 2H), 7.17 (d, J=8.30 Hz, 2H), 6.88 (d, J=8.30 Hz, 2H), 4.20 (d, J=5.71 Hz, 2H), 3.73 (s, 3H), 3.44 (s, 3H); $^{13}$C NMR (214 MHz, DMSO-d$_6$) δ 170.5, 166.5, 164.4, 158.7, 137.7, 137.4, 133.8, 133.7, 133.4, 133.2, 131.8, 131.2, 130.9, 129.7, 129.3, 129.1, 128.4, 127.8, 126.9, 120.9, 114.2, 55.5, 42.3, 42.2.

Example 17

3-Chloro-N-(4-(2-((4-fluorobenzyl)amino)-2-oxo-ethyl)phenyl)benzamide (KAC-16)

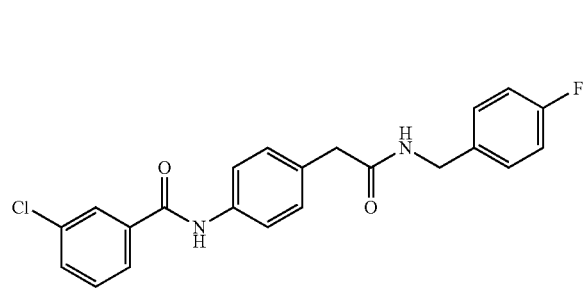 [SMILES: O=C(Cc1ccc(NC(=O)c2cccc(Cl)c2)cc1)NCc1ccc(F)cc1]

This compound was prepared by reacting KAC-14 with 3-chlorobenzoyl chloride according to the procedure described for the synthesis of KAC-1. mp 218° C. $^1$H NMR (850 MHz, DMSO-$d_6$) δ 10.33 (s, 1H), 8.54 (s, 1H), 8.01 (t, J=1.82 Hz, 1H), 7.92 (d, J=7.78 Hz, 1H), 7.69 (d, J=8.30 Hz, 2H), 7.66-7.68 (m, 1H), 7.56-7.59 (m, 1H), 7.28 (dd, J=5.71, 8.82 Hz, 2H), 7.26 (d, J=8.82 Hz, 2H), 7.14 (t, J=8.82 Hz, 2H), 4.26 (d, J=6.23 Hz, 2H); $^{13}$C NMR (214 MHz, DMSO-$d_6$) δ 170.7, 164.4, 162.2, 137.7, 137.4, 136.2, 136.2, 133.7, 132.4, 131.8, 130.9, 129.7, 129.7, 129.6, 127.8, 126.9, 120.9, 115.5, 115.5, 115.4, 42.3, 42.0

Example 18

3-Chloro-N-(4-(2-oxo-2-(phenethylamino)ethyl)phenyl)benzamide (KAC-17)

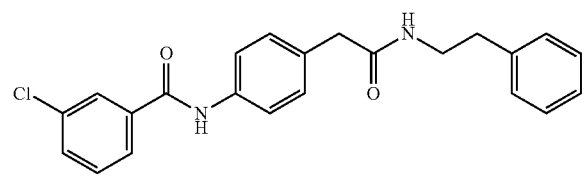 [SMILES: O=C(Cc1ccc(NC(=O)c2cccc(Cl)c2)cc1)NCCc1ccccc1]

This compound was prepared by reacting KAC-14 with 3-chlorobenzoyl chloride according to the procedure described for the synthesis of KAC-1, mp 160° C. $^1$H NMR (850 MHz, DMSO-$d_6$) δ 10.32 (s, 1H), 8.09 (s, 1H), 8.01 (t, J=1.82 Hz, 1H), 7.92 (dd, J=1.56, 7.78 Hz, 1H), 7.89-7.91 (m, 1H), 7.66-7.69 (m, 2H), 7.57 (t, J=7.79 Hz, 1H), 7.27-7.30 (m, 2H), 7.19-7.22 (m, 2H), 7.17-7.19 (m, 2H), 3.37 (s, 2H), 3.27-3.30 (m, 2H), 2.71 (t, J=7.27 Hz, 2H); $^{13}$C NMR (214 MHz, DMSO-$d_6$) δ 170.6, 166.5, 164.4, 139.9, 137.6, 137.4, 133.7, 133.2, 132.5, 131.8, 131.2, 130.9, 129.6, 129.3, 129.2, 128.8, 128.4, 127.9, 126.9, 126.5, 120.8, 42.4, 40.8, 35.5.

Example 19

3-Chloro-N-(4-(2-((furan-2-ylmethyl)amino)-2-oxo-ethyl)phenyl)benzamide (KAC-18)

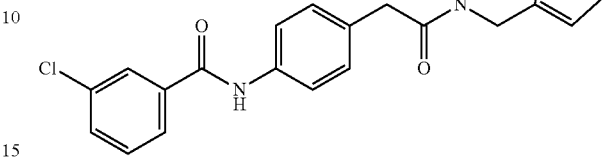

This compound was prepared by reacting KAC-14 with 3-chlorobenzoyl chloride according to the procedure described for the synthesis of KAC-1. mp 206° C. $^1$H NMR (850 MHz, DMSO-$d_6$) δ 10.32 (s, 1H), 8.51 (s, 1H), 8.01 (t, J=1.82 Hz, 1H), 7.89-7.94 (m, 1H), 7.66-7.70 (m, 2H), 7.54-7.59 (m, 2H), 7.25 (d, J=8.30 Hz, 2H), 6.38-6.40 (m, 1H), 6.21 (d, J=3.11 Hz, 1H), 4.27 (d, J=5.71 Hz, 2H), 3.43 (s, 2H); $^{13}$C NMR (214 MHz, DMSO-$d_6$) δ 170.5, 166.5, 164.4, 152.7, 142.6, 137.7, 137.4, 133.7, 133.2, 132.3, 131.8, 131.2, 130.9, 129.7, 129.3, 128.4, 127.8, 126.9, 120.9, 110.9, 107.3, 42.1, 36.1.

Example 20

Chemical Synthesis: Results and Discussions

As shown in FIG. 3, the synthesis was started by stirring 2-(4-nitrophenyl)acetic acid 1 at room temperature for 4 hrs with oxalyl chloride in dichloromethane (DCM) and a catalytic amount of N,N-dimethylformamide (DMF) to afford 2-(4-nitrophenyl) acetyl chloride 2. In an ice bath, compound 3 was prepared by the reaction of 2-(4-nitrophenyl) acetyl chloride 2 and the corresponding amine in the presence of diisopropyl ethylamine (DIPEA) in DCM.

The pivotal amine 4 (i.e. KAC-14) was obtained by reduction of the nitro following one of two techniques. The first method was heating the nitro intermediate 3 in ethyl acetate containing SnCl$_2$ dihydrate for 4 h. Alternatively, the amine 4 (i.e. KAC-14) was prepared using flow chemistry reduction instrument H-Cube Pro™ (Thales Technology, Hungary) using 10% Pd—C cartridge to catalyze the reduction in high pressure (10 atm.) at a temperature of 40° C.

The final step to prepare KAC compounds was accomplished via reaction of the corresponding acid chloride or acid anhydride under appropriate condition to afford KAC final compounds. The acid chloride intermediates for KAC-03 to KAC-07 were prepared according to steps described in FIGS. 4 and 5. Specifically, the corresponding cyclic acid anhydride of phthalic acid (for KAC-03 and KAC-04) or diphenic anhydride (for KAC-05, KAC-06 and KAC-07) was used as the starting material. The appropriate amine was heated with the acid anhydride in toluene. Subsequently, the freed carboxylic acid from the previous step was activated by conversion to acid chloride followed by reaction with the amine 4 (i.e. KAC-14).

All the compounds were confirmed by spectral analysis using NMR and IR, and the molecular formulae were established using FIRMS. The purities were analyzed using LC/MS.

Example 21

Cytotoxic Assay Against HL-60 Cancer Cell Lines: Cell Culture and Reagents

HL-60 cells were purchased from CLS Cell Line Service GmbH (Eppelheim, Germany) and cultured in Roswell Park Memorial Institute-1640 medium (RPMI-1640; Thermo Fisher Scientific, Inc; Waltham, Mass., USA) supplemented with 10% fetal bovine serum (FBS; Thermo Fisher Scientific) and ciprofloxacin (10 µg/ml; Cipla Limited; Mumbai, India), at 37° C. with 5% $CO_2$ in a humidified incubator.

Example 22

Cytotoxic Assay Against HL-60 Cancer Cell Lines: Cell Viability Assay

The CellTiter®-Blue Cell Viability assay was acquired from Promega Corporation (Madison, Wis., USA). Cell viability assay was performed as follows. The cells ($10^4$/well) were incubated with KAC-12 at a concentration gradient ranging from 0.01 to 100 in 96-well plates for 48 h at 37° C. Subsequently, 20 µL of CellTiter®-Blue Cell Viability reagent was added to each well and incubated for an additional 2 h for the development of fluorescence. The fluorescence emission was measured at 590 nm using the SpectraMax® i3x Multi-Mode microplate reader (Molecular Devices, LLC; San Jose, Calif., USA.) and plotted against drug concentrations to determine the mean inhibitory concentration of KAC-12 producing 50% decrease in cell viability ($IC_{50}$).

Example 23

Cytotoxic Assay Against HCT116 and MCF7 Cancer Cell Lines

The KAC compounds were evaluated for antiproliferative effect against HCT-116 and MCF7 cell lines using the MTT viability assay and to calculate the relative $IC_{50}$ values for each compound. Cells were seeded in triplicate in 96-well plates at a density of $10 \times 10^3$ cells/mL in a total volume of 100 µL per well and allowed to adhere overnight. Cells were treated with various concentrations of tested KAC compounds or 0.1% of DMSO (vehicle) for 27 h. Then the medium was discarded and 100 µL per well of MTT (5 mg/mL in PBS) containing medium was added. After incubation at 37° C. for 3 h, the MTT-containing medium was replaced by DMSO (100 µL per well) to dissolve the formazon crystal and incubated for 10 min. Absorbance of the solution was measured by microplate reader at 570 nM. The $IC_{50}$ values were calculated according to the dose-dependent curves using GraphPad prism, version 5.0. All the experiments were repeated in at least three independent experiments.

Example 24

Cytotoxic Assay Against N87 Cancer Cell Lines

Cytotoxicity of all the compounds against N87 cells was determined using MTT assay. Briefly, 25,000 cells suspended in 0.1 mL of cell culture media were added in each well of a 96-well plate. After allowing the cells to attach for 24 h, media was aspirated from all the wells, and different concentrations of anticancer compounds in cell culture media were added to the wells in triplicate. Six wells were incubated with drug free media, and used as control. 96 hours after the treatment, 25 µL of MTT solution (5 mg/mL in phosphate saline buffer, pH 7.4) was added to each well, and the plate was incubated for 4.5 hours at 37° C. in the incubator. After incubation, 100 µL of 10% SDS in 0.01 M hydrochloric acid was added to each well, and the plate was incubated overnight at 37° C. The next day absorbance was determined in each well at 590 nm using a plate reader. $IC_{50}$ value of each compound was determined using GraphPad Prism.

Example 25

Cell Cycle Analysis of H60 Cells Treated with KAC-12

The cells ($3.5 \times 10^5$) were incubated with two different concentrations of KAC-12 at 37° C. for 48 h. Subsequently, the cells were collected and washed twice with ice-cold PBS (1×). The washed cells were fixed on ice for 20 min using a fixation buffer containing paraformaldehyde. Hoechst 33342 (10 µg/mL; Thermo Fisher Scientific, Inc.) was used for staining. The cells were then incubated in the dark for 30 min on ice. A minimum total of 20,000 events were acquired using a BD FACSAria III flow cytometer. Flowlogic version 7.2.1 software (Inivai Technologies, Victoria, Australia) was used to obtain the percentages of cells in the G1, S, and G2/M phases in the singlet-gated population.

Example 26

Cell Cycle Analysis of HCT116 Cells Treated with KAC-03

Flow cytometric analysis was used to determine DNA level in any given cell that has been stained with propidium iodide (PI). PI is a fluorescent DNA intercalating agent which binds stoichiometrically to nucleic acid. When bounded to DNA, its fluorescence intensity increases 20 fold (excitation 488 nm and emission 600 nm). As cells pass singly through a beam of light their cell cycle state is analyzed. The fluorescent intensity of DNA-bound PI correlates to the DNA content of the cell. This allows the cell population in G1 phase (diploid-2n), $G_2M$ phase (4n), or S phase (2n-4n) to be differentiated by plotting a histogram of the PI fluorescence versus cell counts (linear scale). G1 and G2M can be seen as distinct peaks, with the S phase shown as the population between these two peaks. Apoptotic cells are hypo-diploid (pre-G1) and have a low PI fluorescence due to DNA fragmentation [Riccardi, C.; Nicoletti, I., Analysis of apoptosis by propidium iodide staining and flow cytometry. Nature protocols 2006, 1 (3), 1458-1461].

To study cell cycle stage, adherent and detached cells were collected by trypsinization and centrifuged at 800×g for 15 min. Cells were washed twice with ice-cold PBS and fixed with slow addition of ice-cold 70% ethanol overnight at −20° C. Fixed cells were centrifuged at 800×g for 15 min and the pellet was re-suspended in 400 µL PBS and transferred to LP5 FACS tubes then stained with 50 µg/mL of PI, containing 50 µg/mL of DNase-free RNase A (to degraded any double strand RNA present), at 37° C. for 30 min. The DNA content of cells (10,000 cells/experimental group) was analyzed by flow cytometer at 488 nm using a FACSCalibur flow cytometer (BD Biosciences, San Jose, Calif.).

Example 27

Apoptosis Detection by Caspase 3 Activity

The caspase family of cysteine proteases is important regulators in the apoptosis. Caspase 3 belongs to the effector (caspase 3, 6, and 7) class of proteases and it is a key protease that is activated during early stages of apoptosis. Like other proteases, caspase 3 is present in the cell as inactive zymogens that can be activated through proteolytic processing at conserved aspartic residue. The activated caspase 3 is a marker for cell apoptosis that proteolytically cleaves and activates other caspases and intracellular targets [Patel, T.; Gores, G. J.; Kaufmann, S. H., The role of proteases during apoptosis. *FASEB journal: official publication of the Federation of American Societies for Experimental Biology* 1996, 10 (5), 587-97]. FITC conjugated active caspase-3 antibody (BD biosciences, USA) was used to detect the active form of caspase 3 in the cells undergoing apoptosis. Briefly, cells were plated in a 6-well culture plate at a density of $0.5 \times 10^6$ cells and harvested after 24 hours of incubation with the inhibitor treatment. The collected cells were washed twice in cold 1×PBS and then re-suspended in a 0.5 mL BD Cytofix/Cytoperm solution followed by 20 min incubation on ice. After incubation, cells were washed twice in a BD Perm/Wash buffer (1×) and cells were labelled with 5 µL of FITC rabbit anti-caspase 3 antibodies. The labelled cells were washed again with wash buffer and re-suspended in a 0.5 mL buffer and analyzed by acquiring a minimum of 5000 events on the FACS Aria III cell analyzer and sorter.

Example 28

Cytotoxic Assays Against Cancer Cell Lines: Results

The compounds were screened for their anticancer activities against variety of cell lines. Results are illustrated in Table 1.

TABLE 1

Test of KAC compounds on breast cancer cells (MCF7), stomach cancer cells (N87), colon cancer cells (HCT116), and leukemia cells (HL60)

| Compound | $IC_{50}$ (µM) | | | |
|---|---|---|---|---|
| | N87 | HL60 | HCT116 | MCF7 |
| KAC-01 | >50 | | 18.83 | 29.28 |
| KAC-02 | | | | 9.481 |
| KAC-03 | 18.16 | | 4.764 | 3.500 |
| KAC-04 | >50 | | | >50 |
| KAC-05 | | | >50 | 44.25 |
| KAC-06 | >50 | | 30.59 | 34.85 |
| KAC-07 | >50 | | | >50 |
| KAC-08 | >50 | | 19.68 | 2.629 |
| KAC-09 | 7.241 | | >50 | 37.01 |
| KAC-10 | | | 22.67 | |
| KAC-12 | 5.276 | 3.744 | 16.75 | 47.72 |
| KAC-13 | | | 18.97 | 3.222 |
| KAC-14 | >50 | >50 | >50 | |
| KAC-15 | | | >50 | |
| KAC-16 | | | >50 | |
| KAC-17 | | | 25.86 | |
| KAC-18 | | | 23.89 | |

Example 29

Structure Activity Relationship (SAR) Analysis Based on the $IC_{50}$ Data

Structurally, compounds KAC-01 to KAC-13 share a common scaffold that is diversified only in one position, the para amide group. The diversity among this subset can be generally fallen into three substructure groups: aliphatic amide (KAC-01 and KAC-09); aromatic amides with a bulky substituent (KAC-2 to KAC-7); and aromatic amides with a smaller substituent (KAC-08 to KAC-13). Compounds from KAC-15 to KAC-18 are analogues of KAC-12.

KAC-14 (no amide on the para position) did not affect any of the tested cell lines while simple acetylation (KAC-01) exhibited significant inhibition of HCT116 (18.8 µM) and MCF7 (29.28 This highlighted the necessity of the acyl group for inducing any anticancer activities. Increasing the aliphatic chain of the acyl group in KAC-01 from one carbon (acetyl) to two carbons (propanoyl, KAC-09) increased the cytotoxic activities against N87 (7.2 µM) but decreased activities against breast cancer MCF7 cell lines (37 µM).

The presence of aromatic amide in the studied para position boosted the activities variably depending on the cell lines as well as the substituents. The unsubstituted benzoyl derivative KAC-08 exerted high inhibitory potency against breast cancer (2.6 µM) but was less active (19.7 µM) against colon cancer, and much weaker against stomach cancer. Substitution on the benzoyl group impacted cytotoxic activities. For instance, substantial (bulkier) substitutions (KAC-3) showed higher activity against HCT116 (4.8 µM) and MCF7 (3.5 µM) but not N87 cell lines. While smaller substitutions, e.g. KAC-12, exhibited greater activity against N87 (5.3 µM) but was weaker against breast and colon cancer cell lines.

Among the aforementioned compounds, KAC-12 was screened further against leukemia cell lines that are dependent on Src for proliferation [Li, S., Src kinase signaling in leukaemia. *The international journal of biochemistry & cell biology* 2007, 39 (7-8), 1483-1488]. The survival of leukemia cell lines HL60 as well as the stomach tumor cell lines N87 was effectively inhibited by KAC-12 ($IC_{50}$ values were determined to be 3.7 and 5.2 µM, respectively). However, this compound was less effective against HCT116 cell lines (16.7 µM).

Due to confirmed anticancer activities of KAC-12, we studied analogues of this compound by keeping the meta-chlorobenzoyl moiety and diversified the N-benzyl group (the right side of the molecule) in order to increase potency against colon cancer cell lines (KAC 15 to KAC 18). The results suggested that there is no gained benefit and the N-benzyl group is not an attractive position for SAR studies. This N-benzyl sensitivity is in agreement with previous finding of the N-benzyl position of the biphenyl KX series [Smolinski, M. P.; Bu, Y.; Clements, J.; Gelman, I. H.; Hegab, T.; Cutler, D. L.; Fang, J. W. S.; Fetterly, G.; Kwan, R.; Barnett, A.; Lau, J. Y. N.; Hangauer, D. G., Discovery of Novel Dual Mechanism of Action Src Signaling and Tubulin Polymerization Inhibitors (KX2-391 and KX2-361). *Journal of medicinal chemistry* 2018, 61 (11), 4704-4719; and Hangauer, Jr. D. G., Compositions for treating cell proliferation disorders, U.S. Pat. No. 7,300,931 B2].

Example 30

Mechanism of Cytotoxic Activities of KAC-12 on Leukemia H-60 Cells: Cell Cycle Analysis In order to understand the mechanism of action of KAC-12 we performed cell cycle analysis of Hoechst 33342 stained HL-60 cells by flow cytometry. HL-60 cells were first incubated with the $IC_{50}$ dose and 2×IC50 doses of KAC-12 for 24 h (FIG. 7). Treatment with KAC-12 led to arrest of cells in G2/M phase. KAC-12 at 3.74 µM led to about 5-fold increase in the cells in G2/M stage as compared to control. At 7.48 KAC-12 leads to 6-fold increase in the G2/M cells. This activity of KAC-12 is mediated by its anti-tubulin polymerization properties.

Example 31

Mechanism of Cytotoxic Activities of KAC-12 on Leukemia HL-60 Cells: Apoptosis Test HL-60 cells are known to be dependent on src kinases for differentiation. Inhibition of Src kinase mediated activation of STAT3 leads to apoptosis in HL-60 cells. We therefore performed apoptosis assay to detect caspase-3activity (FIG. 8). Treatment of HL-60 cells with 3.74 µM and 7.49 µM of KAC-12, respectively led to a 3-fold increase in the cells undergoing apoptosis as compared to the basal apoptosis in HL-60 cells.

Example 32

Mechanism of Cytotoxic Activities of KAC-03 on Colon Cancer HT116 Cells

Figure 9:
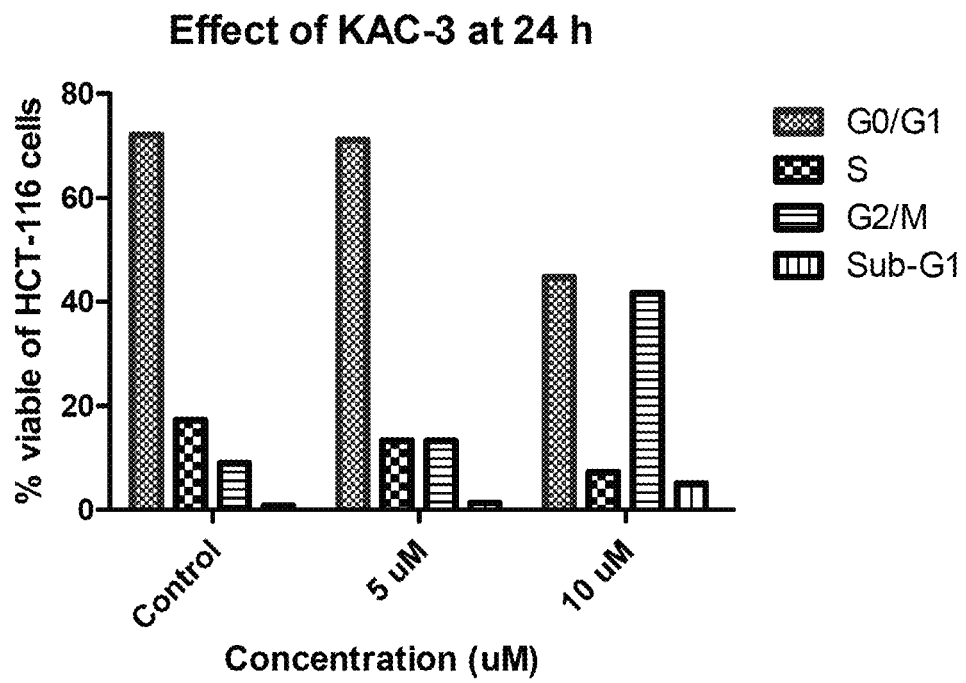
FIG. 9 is a bar graph summarizing cell cycle analysis that shows G2/M arrest in HCT-116 cells upon treatment of control (0.01% DMSO), and KAC-3 at concentrations of 5 and 10 respectively, for 24 hours.
Figure 10:
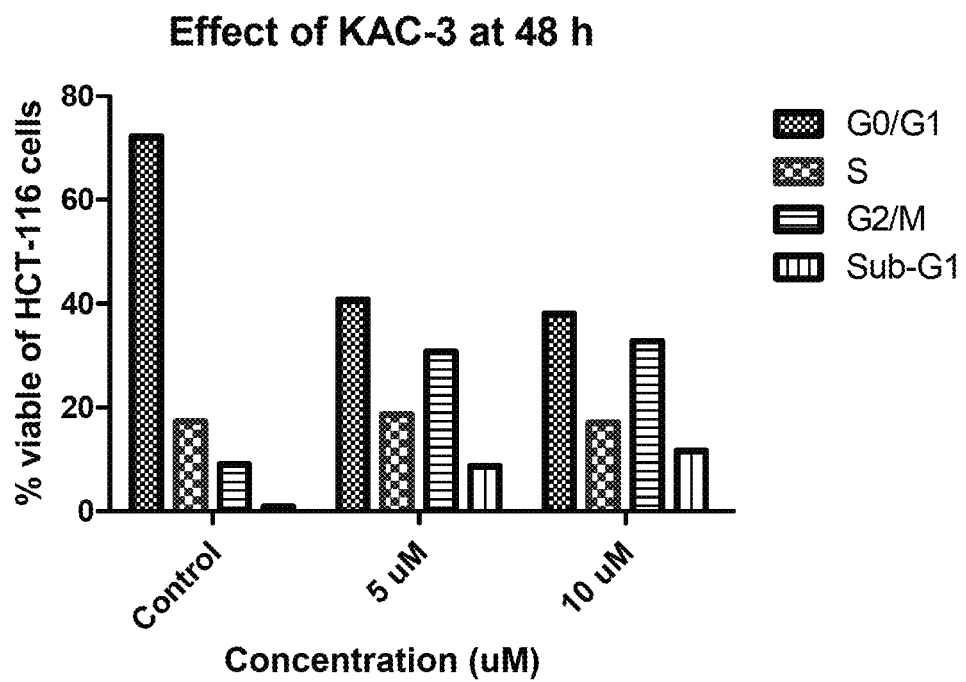
FIG. 10 is a bar graph summarizing cell cycle analysis that shows G2/M arrest followed by apoptosis in HCT-116 cells upon treatment of control (0.01% DMSO), and KAC-3 at concentrations of 5 µM and 10 respectively, for 48 hours.
Figure 11:
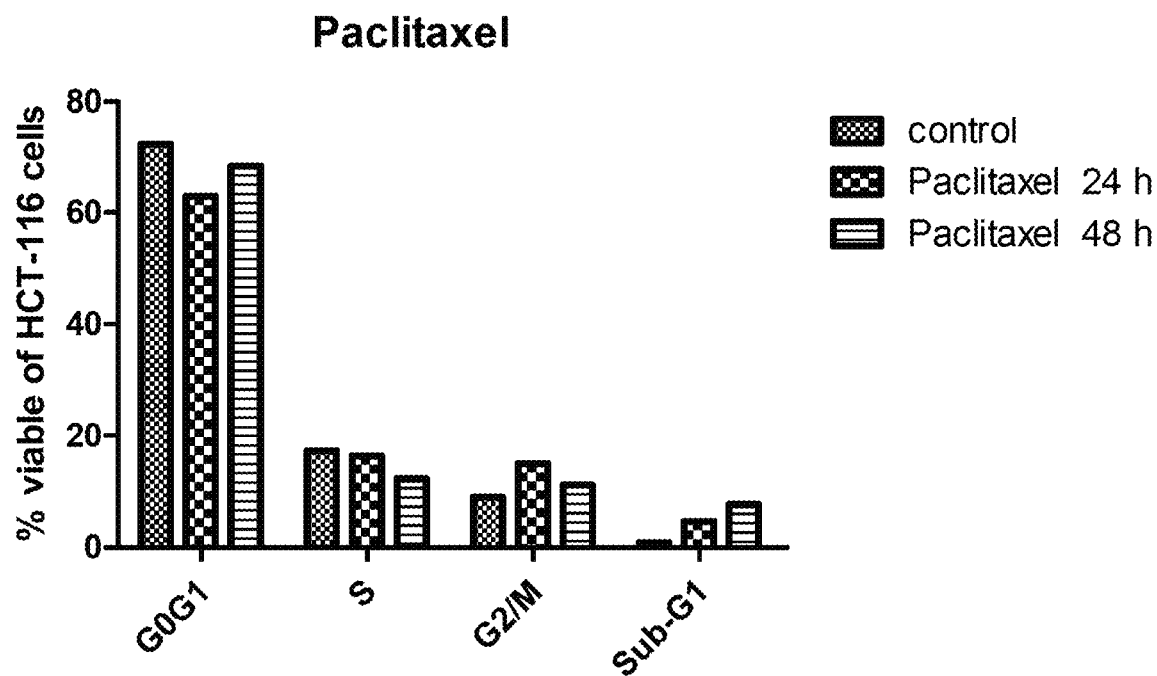
FIG. 11 is a bar graph summarizing cell cycle analysis that shows apoptosis in HCT-16 cells upon treatment of control (0.01% DMSO), and Paclitaxel at a concentration of 1 µM for 24 and 48 hours, respectively.
Figure 12:
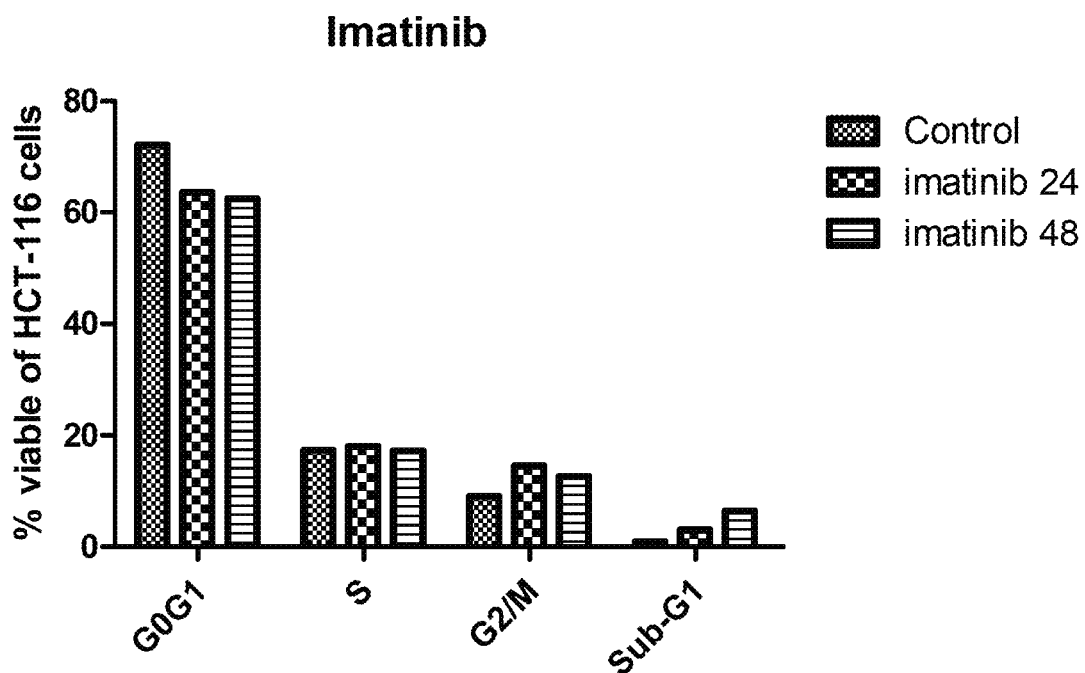
FIG. 12 is a bar graph summarizing cell cycle analysis that shows apoptosis in HCT-16 cells upon treatment of control (0.01% DMSO), and Imatinib at a concentration of 1 for 24 and 48 hours, respectively.
Figure 13:
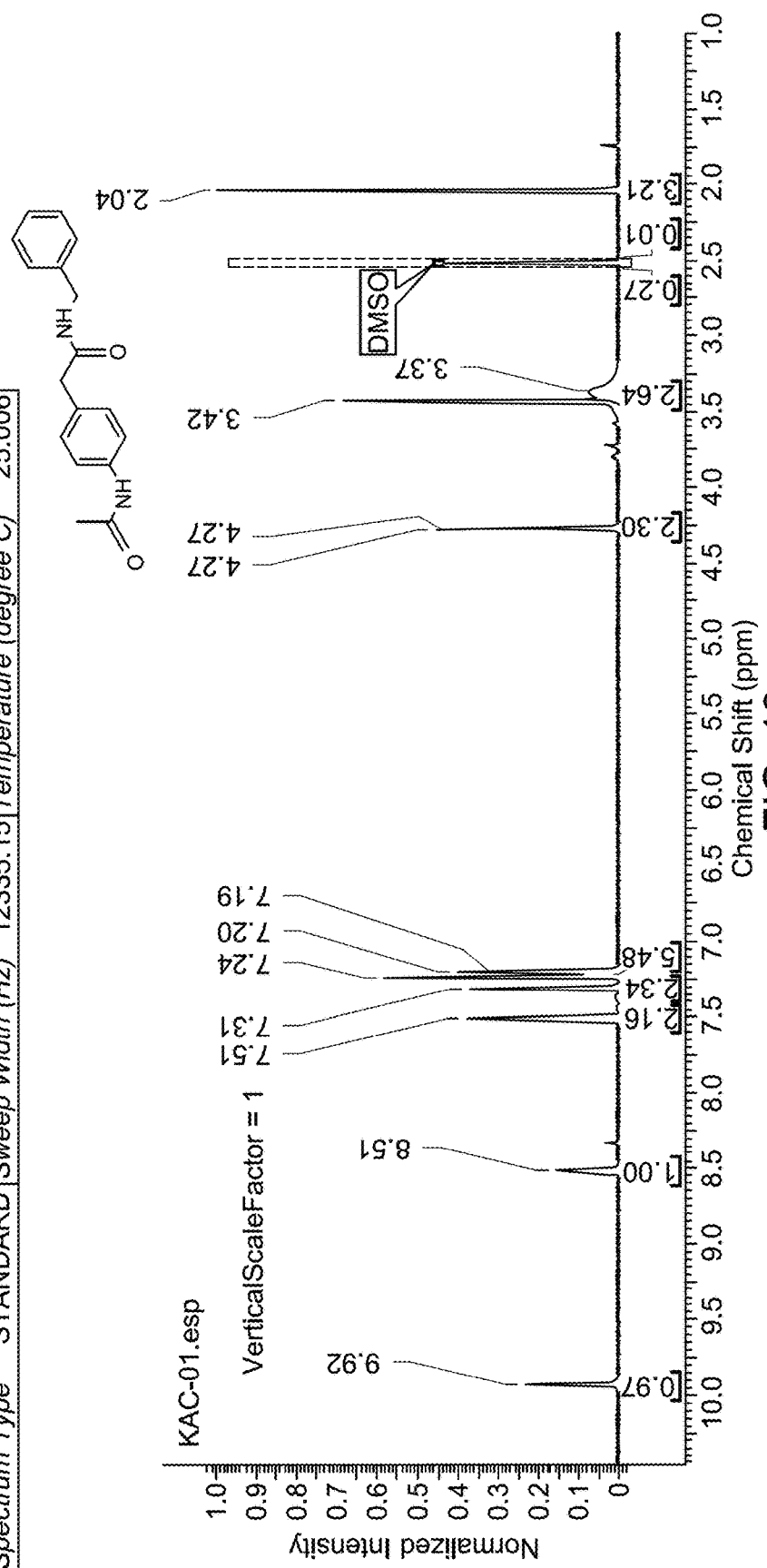
FIG. 13 is a $^1$H nuclear magnetic resonance (NMR) spectrum of compound KAC-01 in DMSO-$d_6$.
Figure 14:
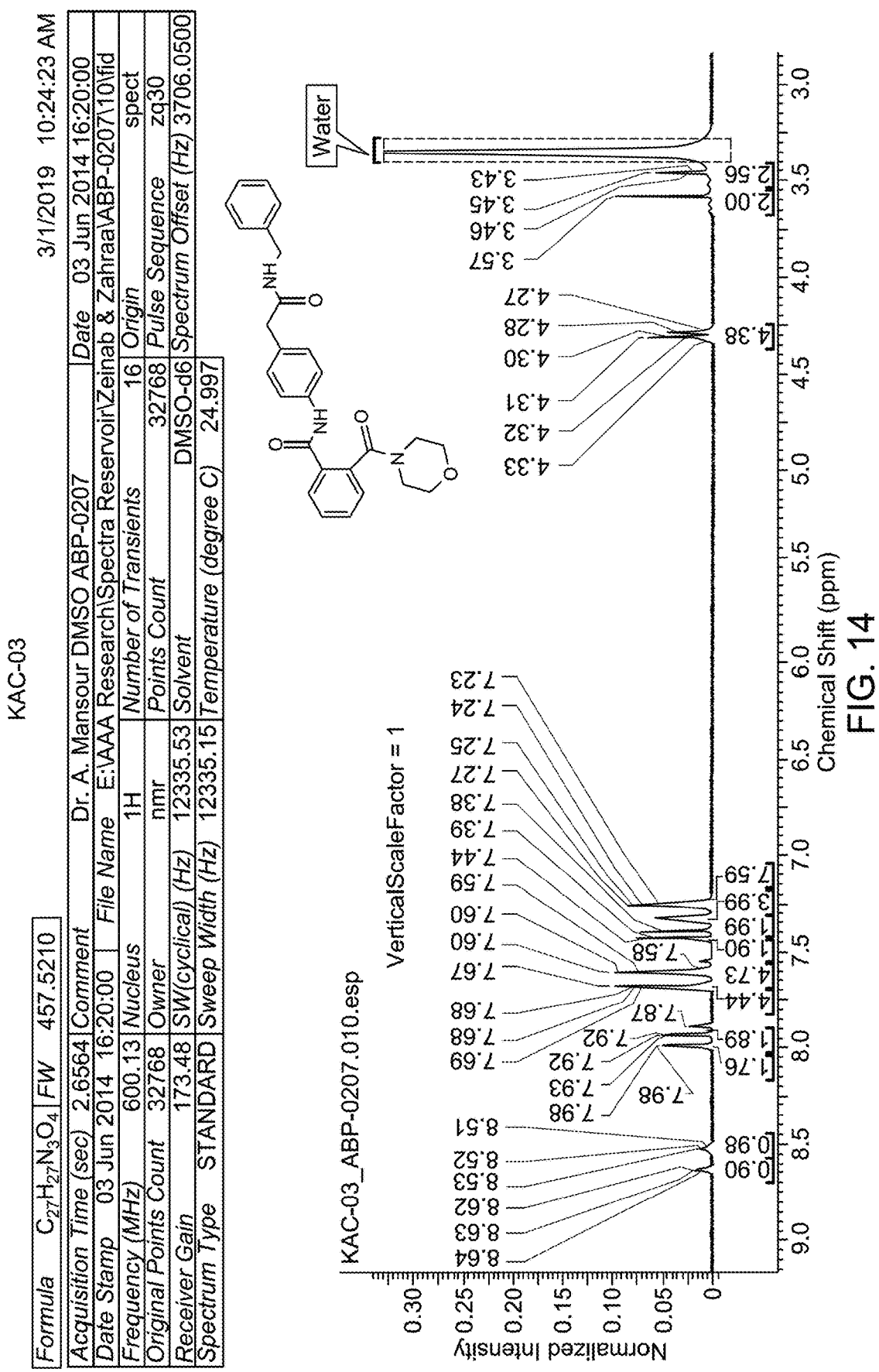
FIG. 14 is a $^1$H NMR spectrum of compound KAC-03 in DMSO-$d_6$.
Figure 15:
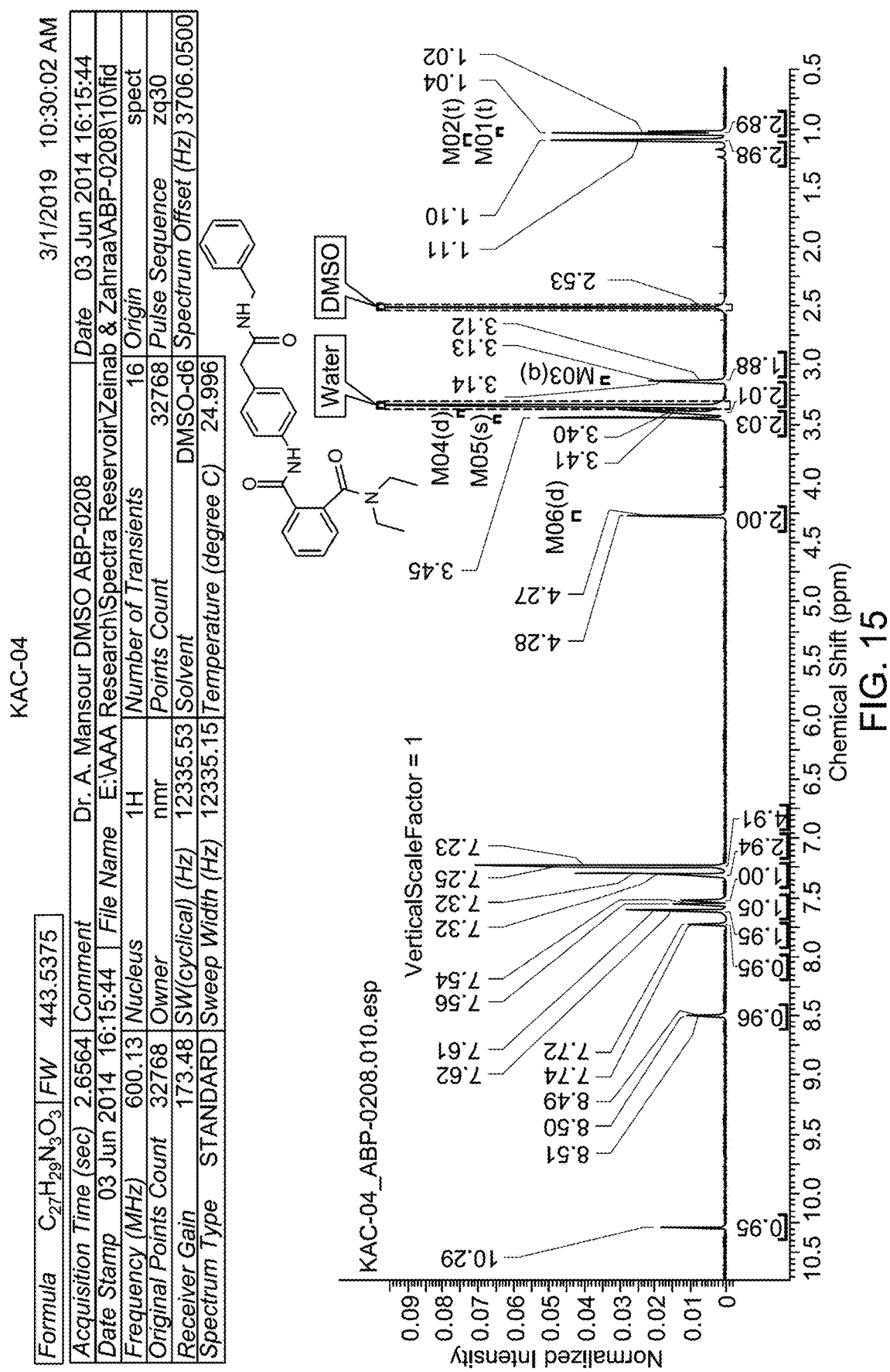
FIG. 15 is a $^1$H NMR spectrum of compound KAC-04 in DMSO-$d_6$.
Figure 16:
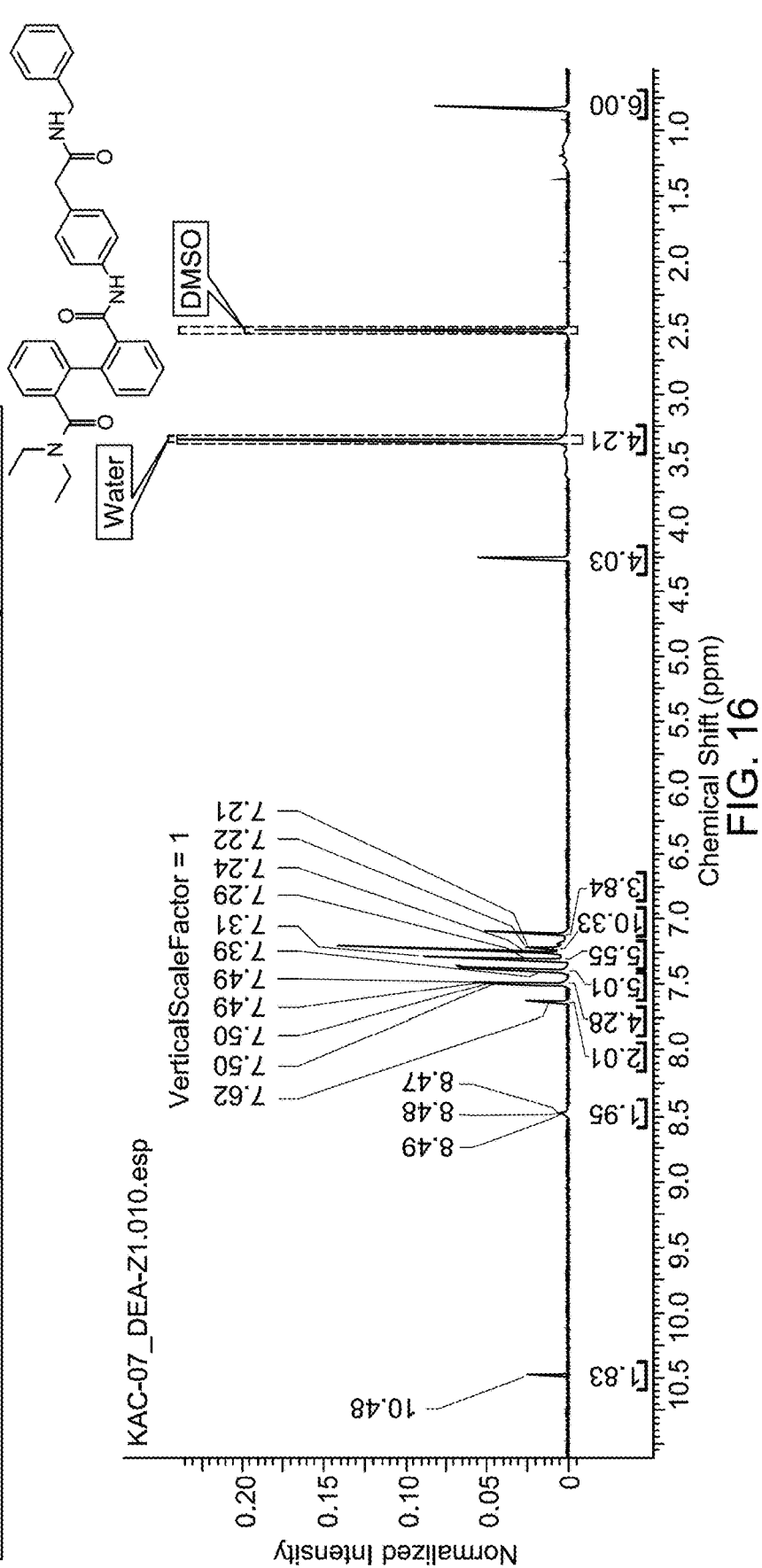
FIG. 16 is a $^1$H NMR spectrum of compound KAC-07 in DMSO-d$_6$.
Figure 17:
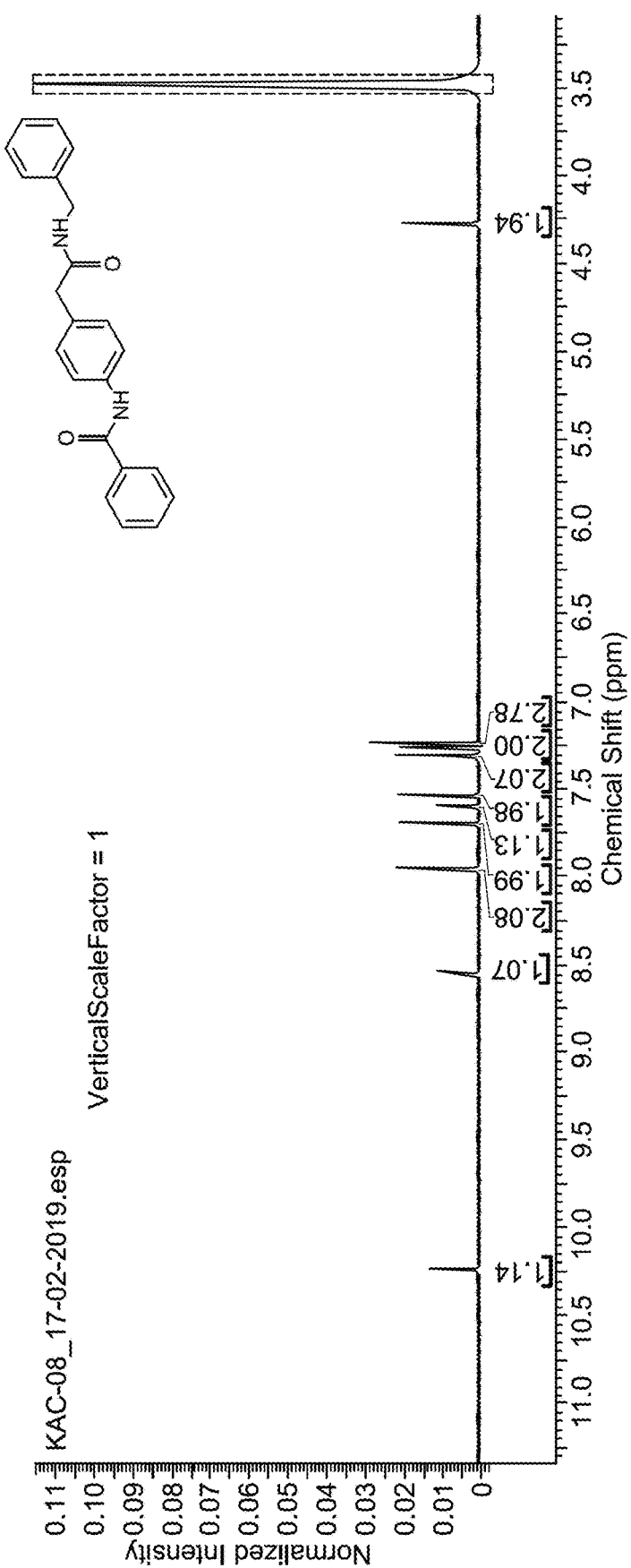
FIG. 17 is a $^1$H NMR spectrum of compound KAC-08 in DMSO-d$_6$.
Figure 18:
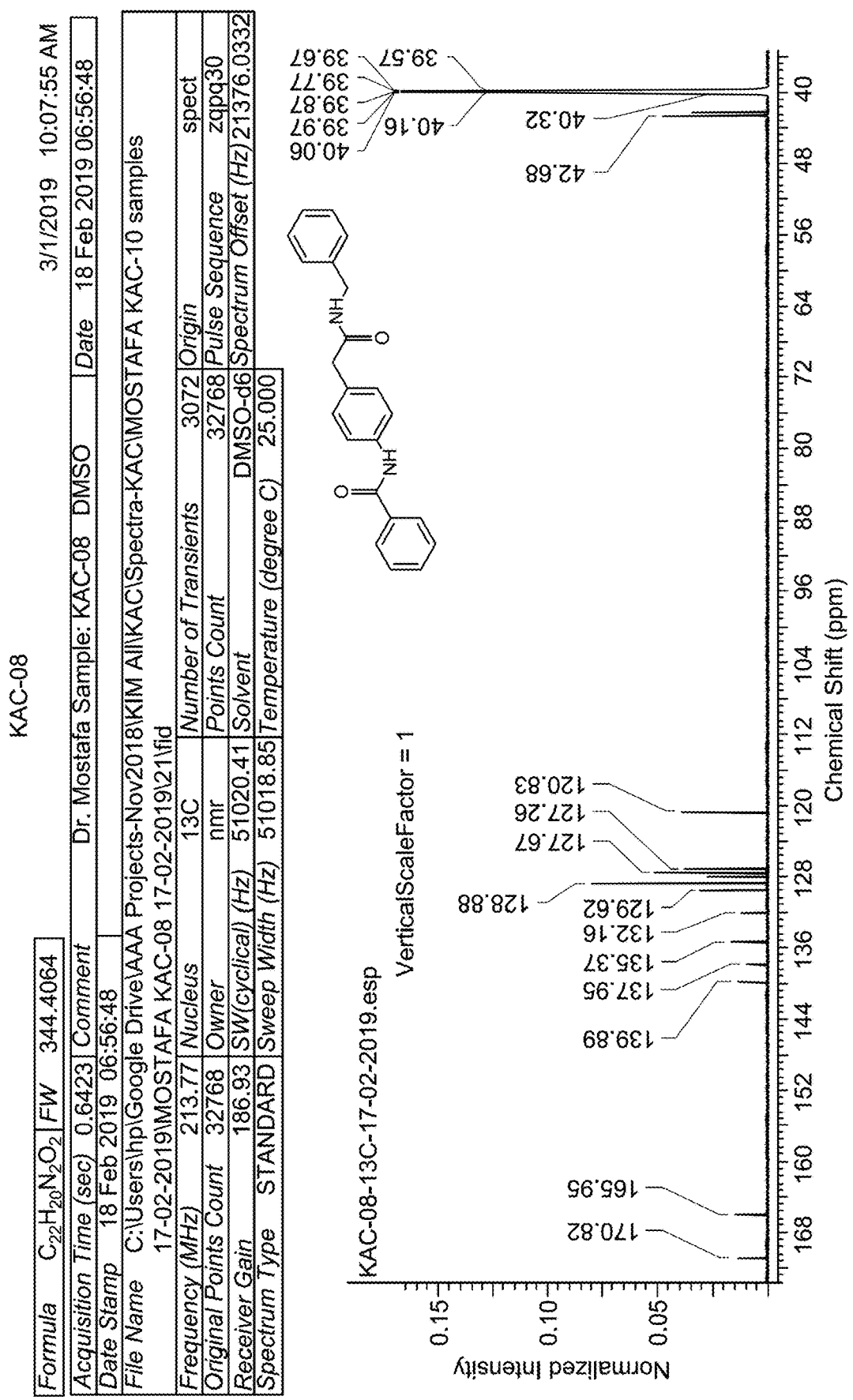
FIG. 18 is a $^{13}$C NMR spectrum of compound KAC-08 in DMSO-d$_6$.
Figure 19:
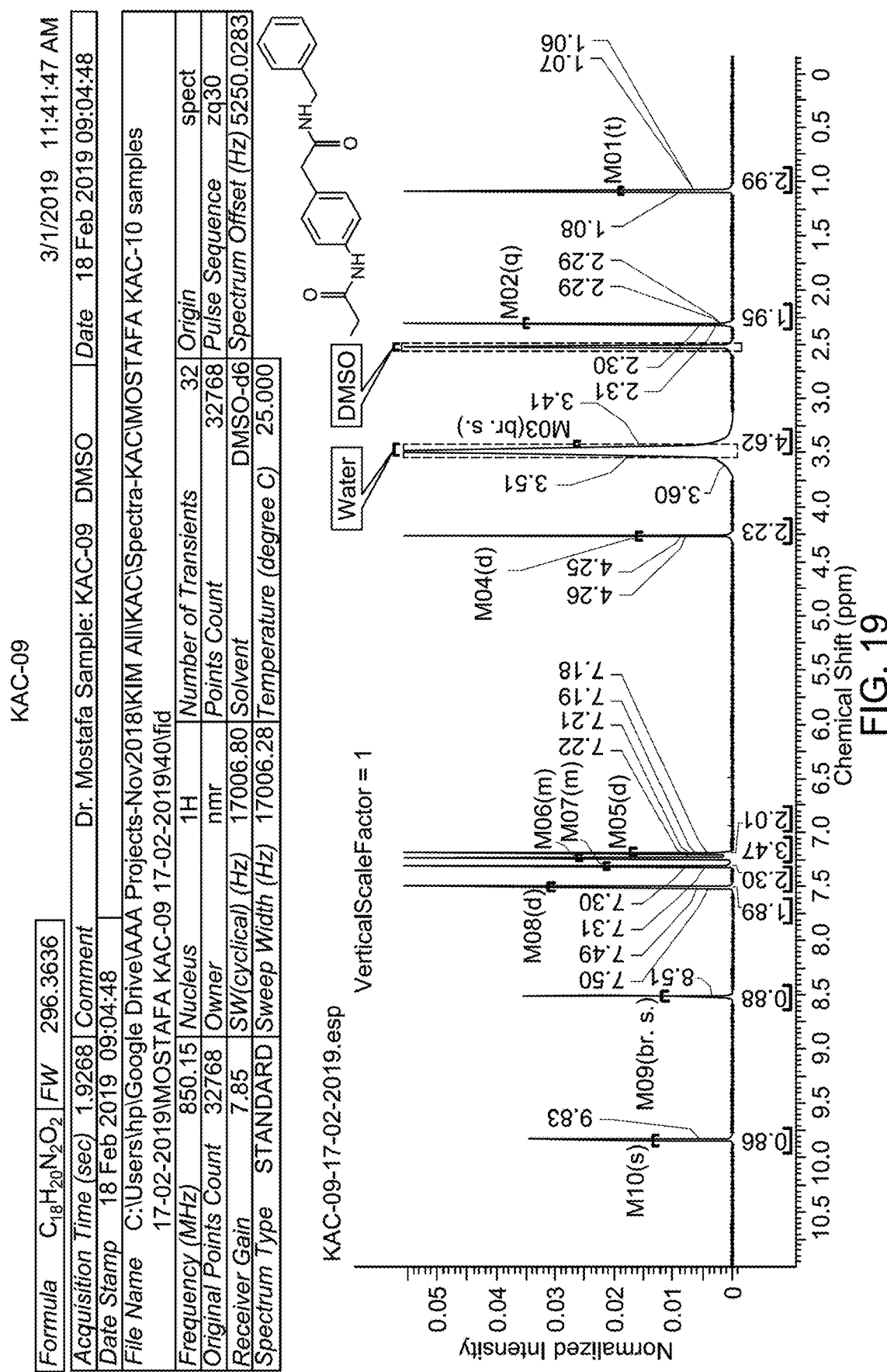
FIG. 19 is a $^1$H NMR spectrum of compound KAC-09 in DMSO-d$_6$.
Figure 20:
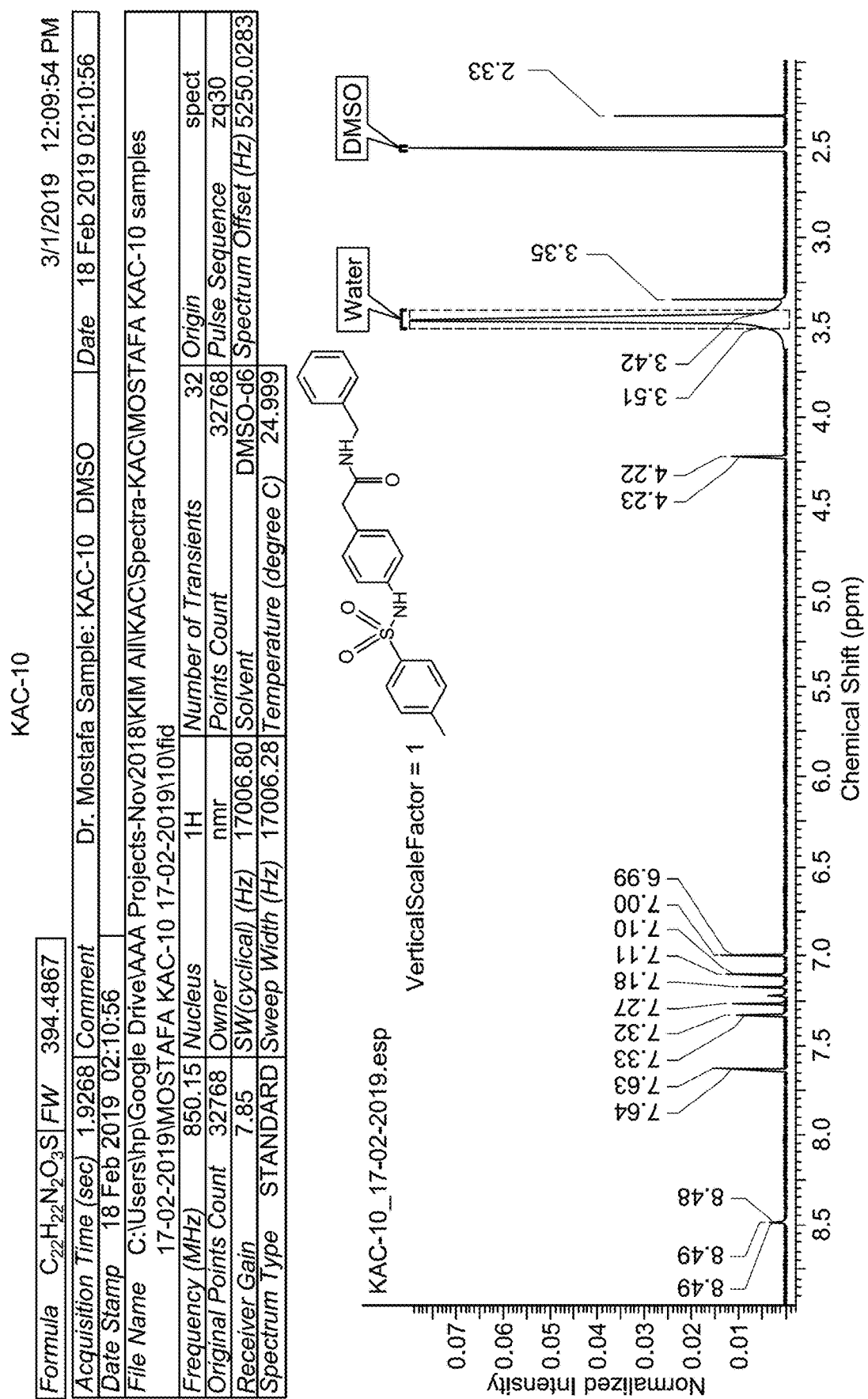
FIG. 20 is a $^1$H NMR spectrum of compound KAC-10 in DMSO-d$_6$.
Figure 21:
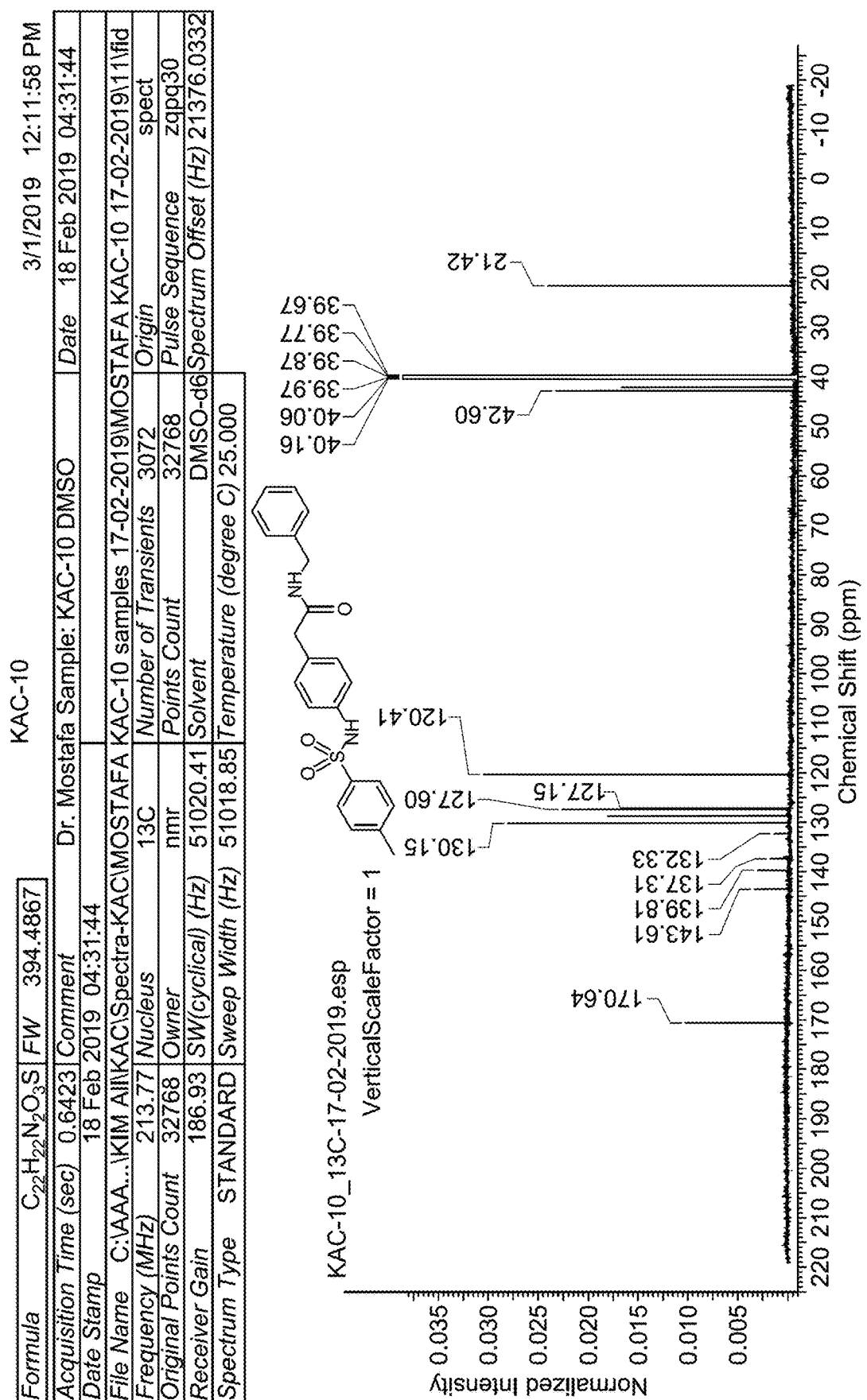
FIG. 21 is a $^{13}$C NMR spectrum of compound KAC-10 in DMSO-d$_6$.
Figure 22:
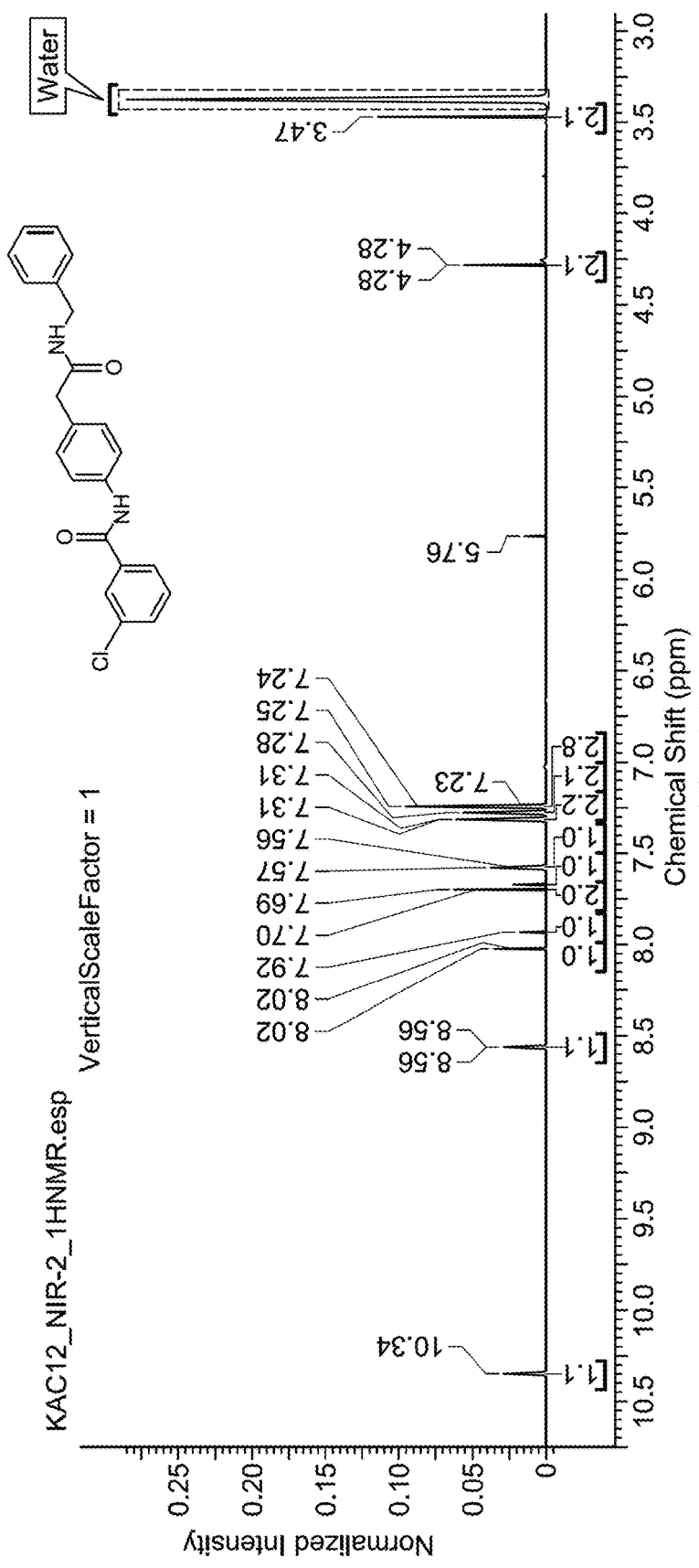
FIG. 22 is a $^1$H NMR spectrum of compound KAC-12 in DMSO-d$_6$.
Figure 23:
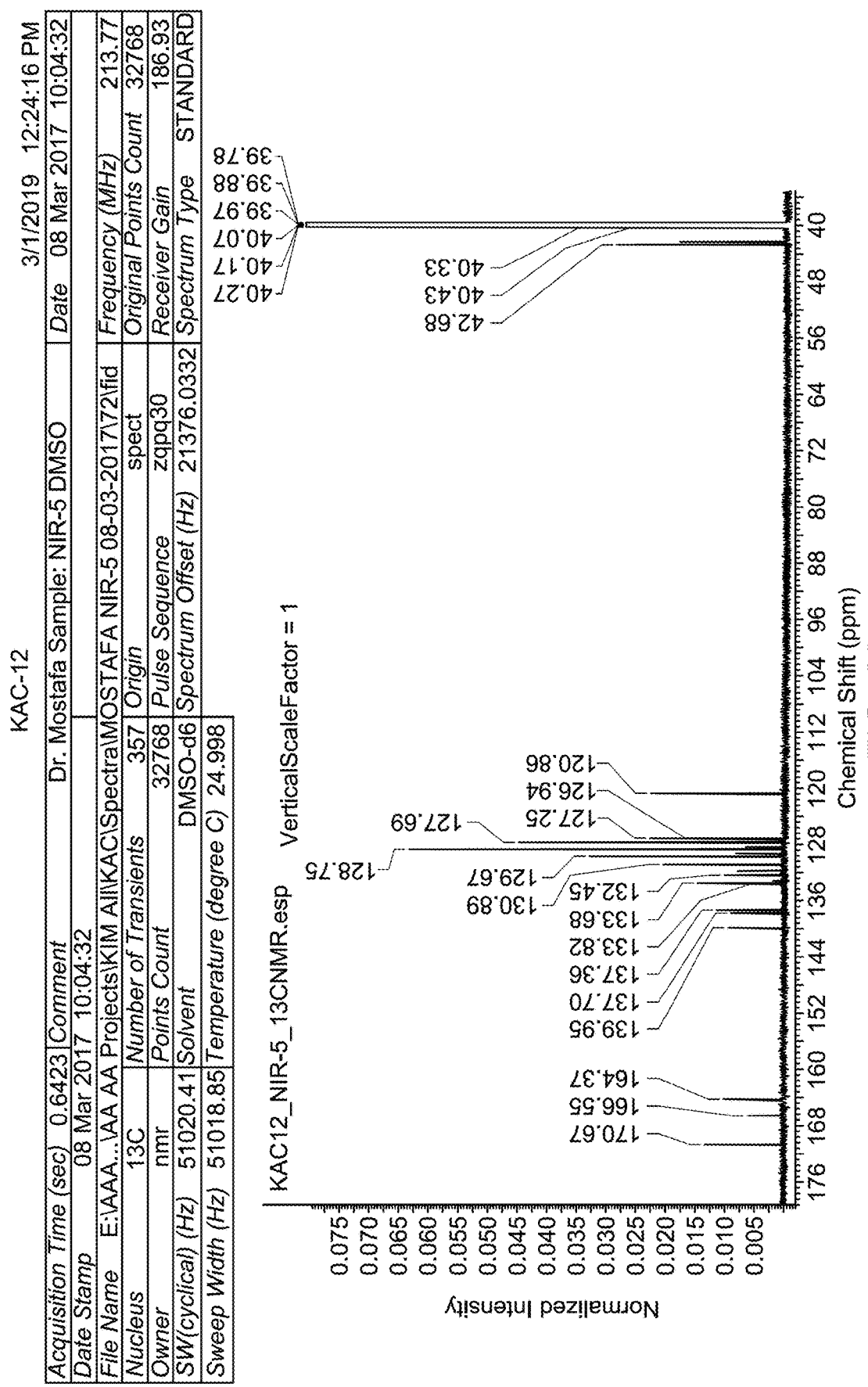
FIG. 23 is a $^{13}$C NMR spectrum of compound KAC-12 in DMSO-d$_6$.
Figure 24:
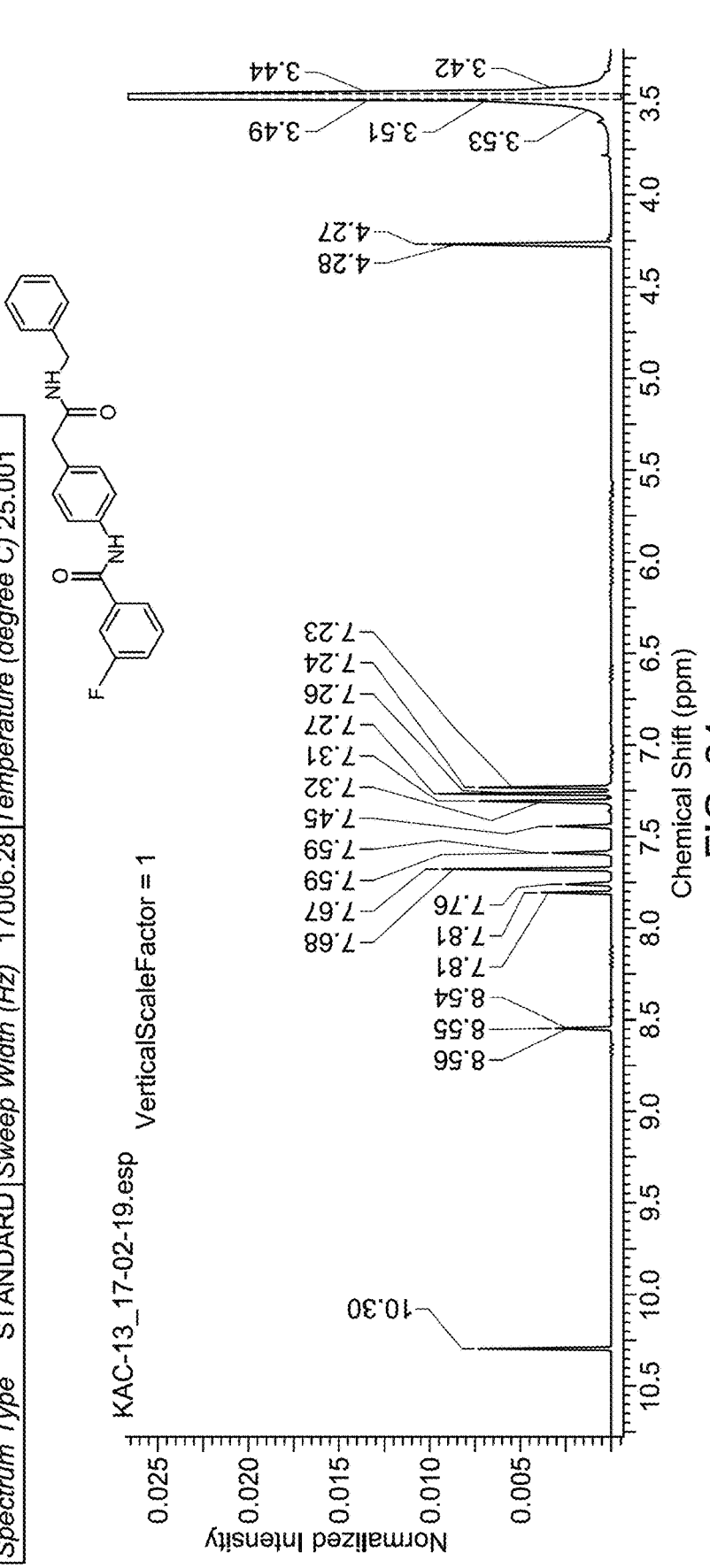
FIG. 24 is a $^1$H NMR spectrum of compound KAC-13 in DMSO-d$_6$.
Figure 25:
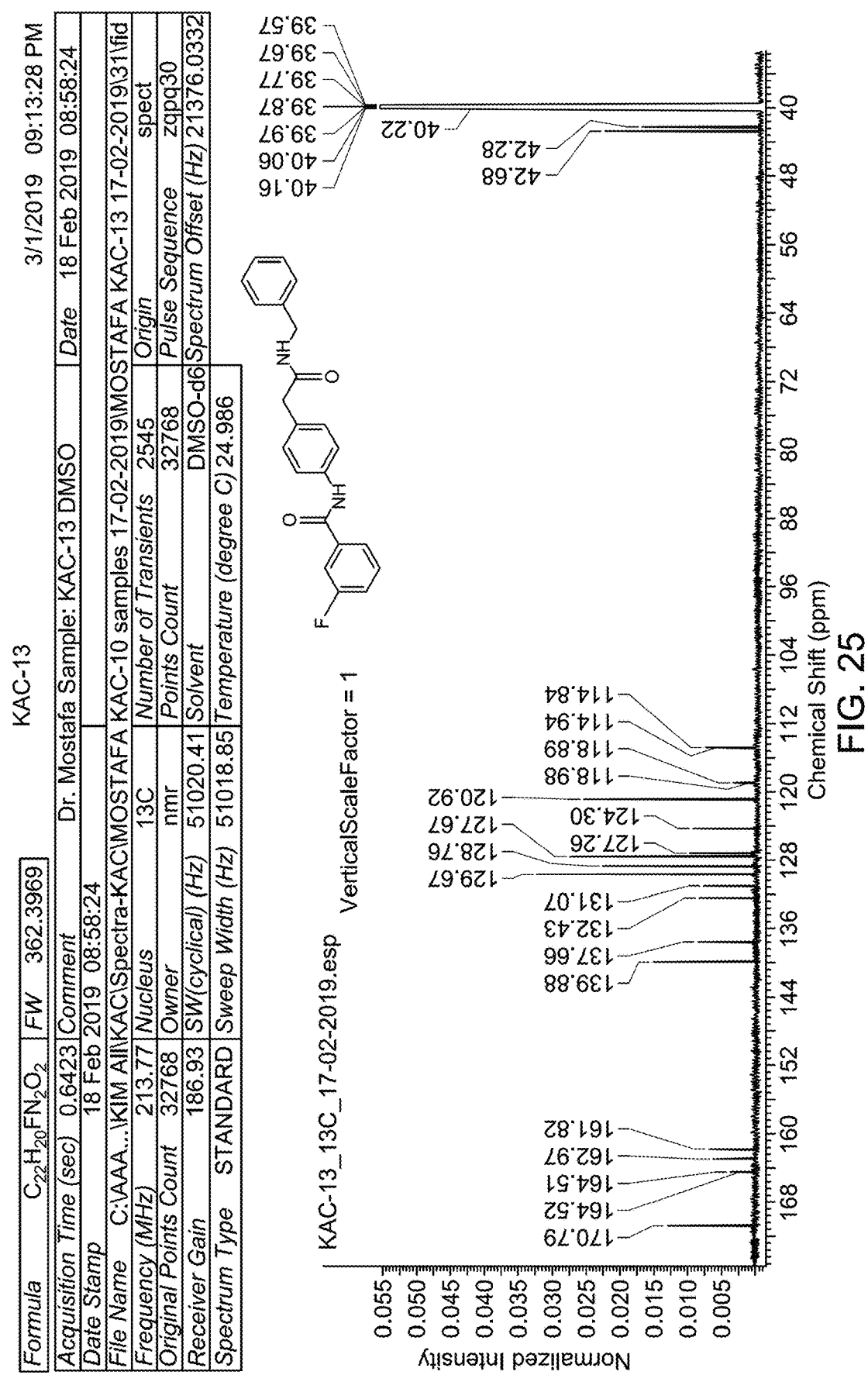
FIG. 25 is a $^{13}$C NMR spectrum of compound KAC-13 in DMSO-d$_6$.
Figure 26:
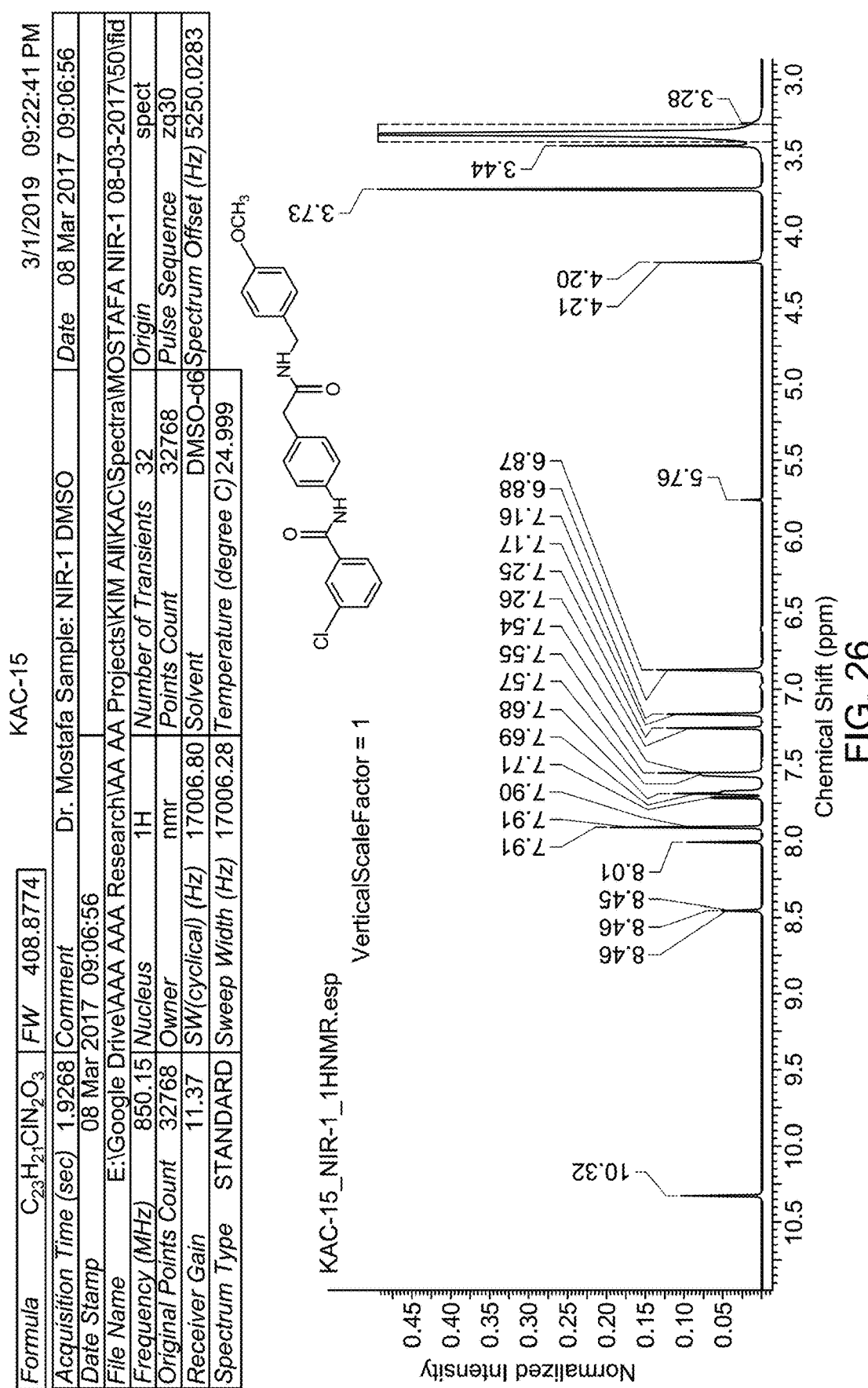
FIG. 26 is a $^1$H NMR spectrum of compound KAC-15 in DMSO-d$_6$.
Figure 27:
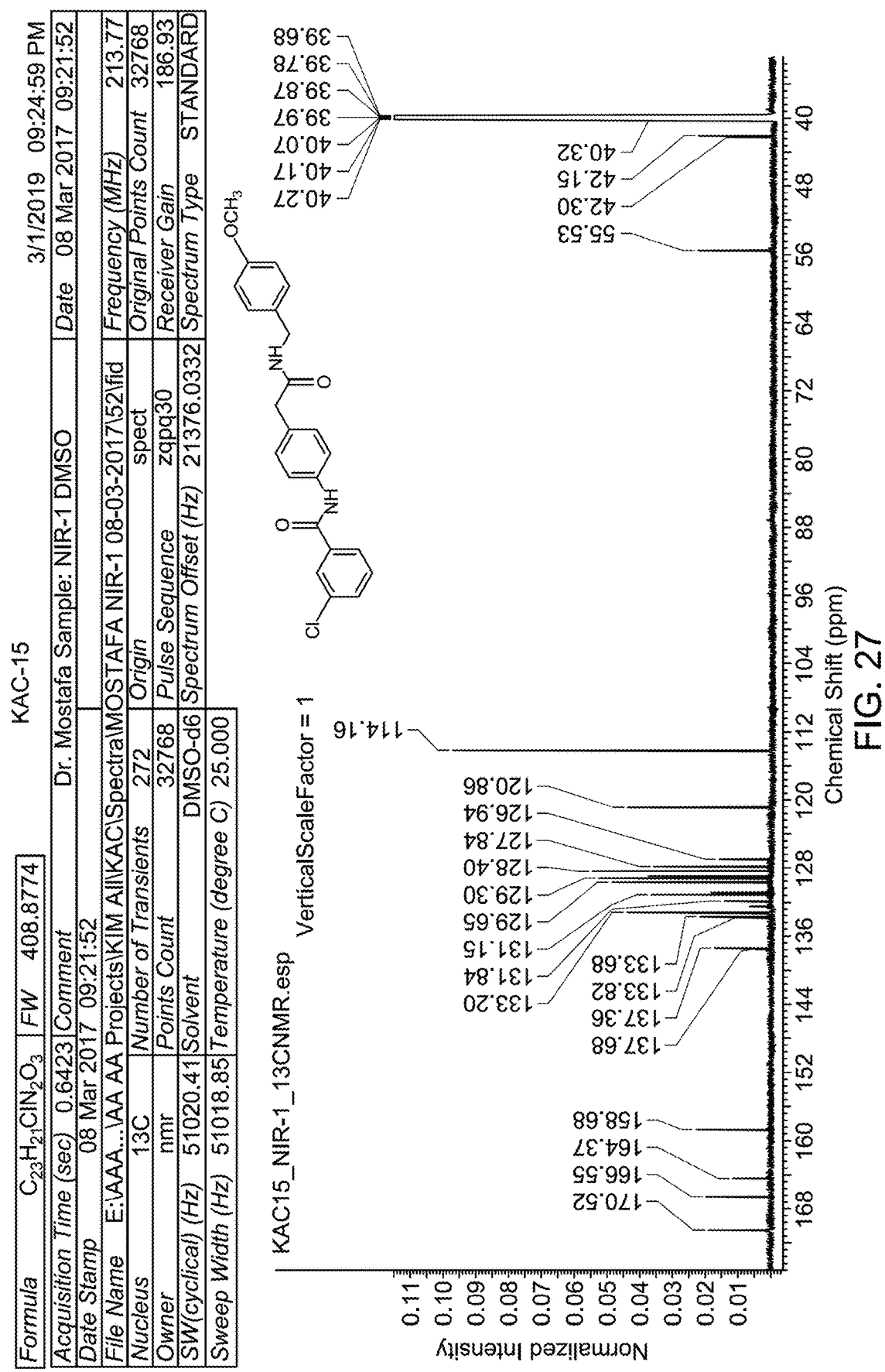
FIG. 27 is a $^{13}$C NMR spectrum of compound KAC-15 in DMSO-d$_6$.
Figure 28:
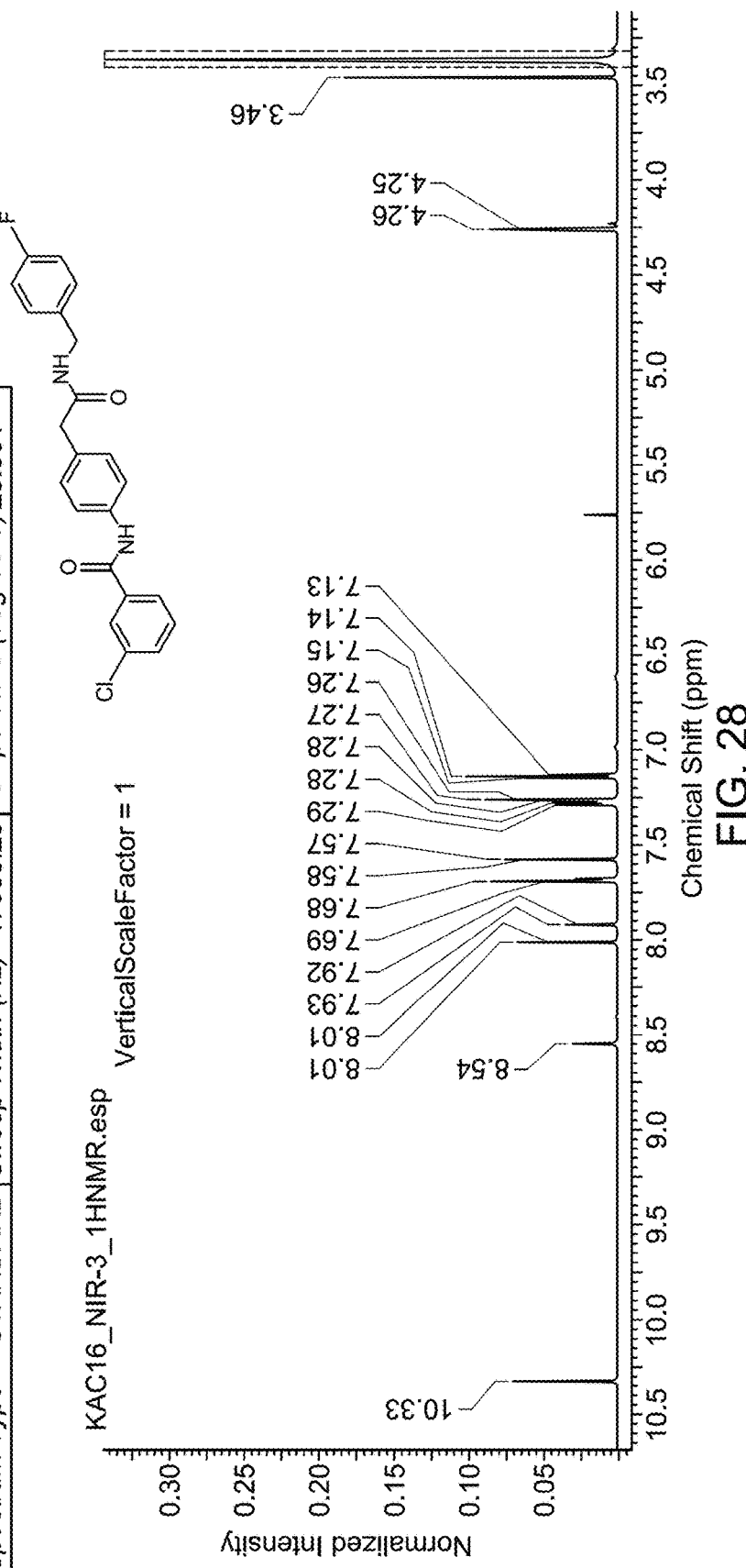
FIG. 28 is a $^1$H NMR spectrum of compound KAC-16 in DMSO-d$_6$.
Figure 29:
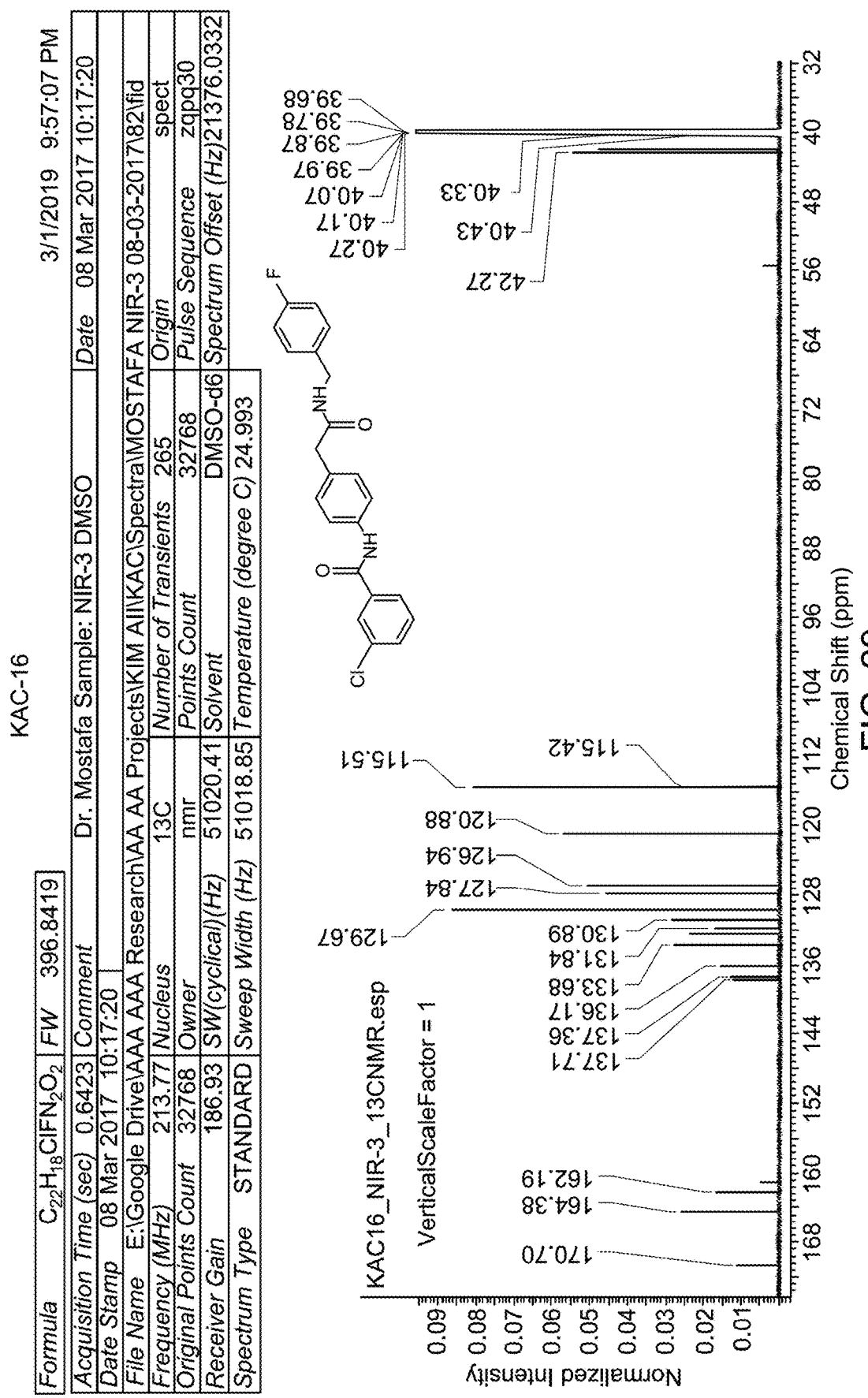
FIG. 29 is a $^{13}$C NMR spectrum of compound KAC-16 in DMSO-d$_6$.
Figure 30:
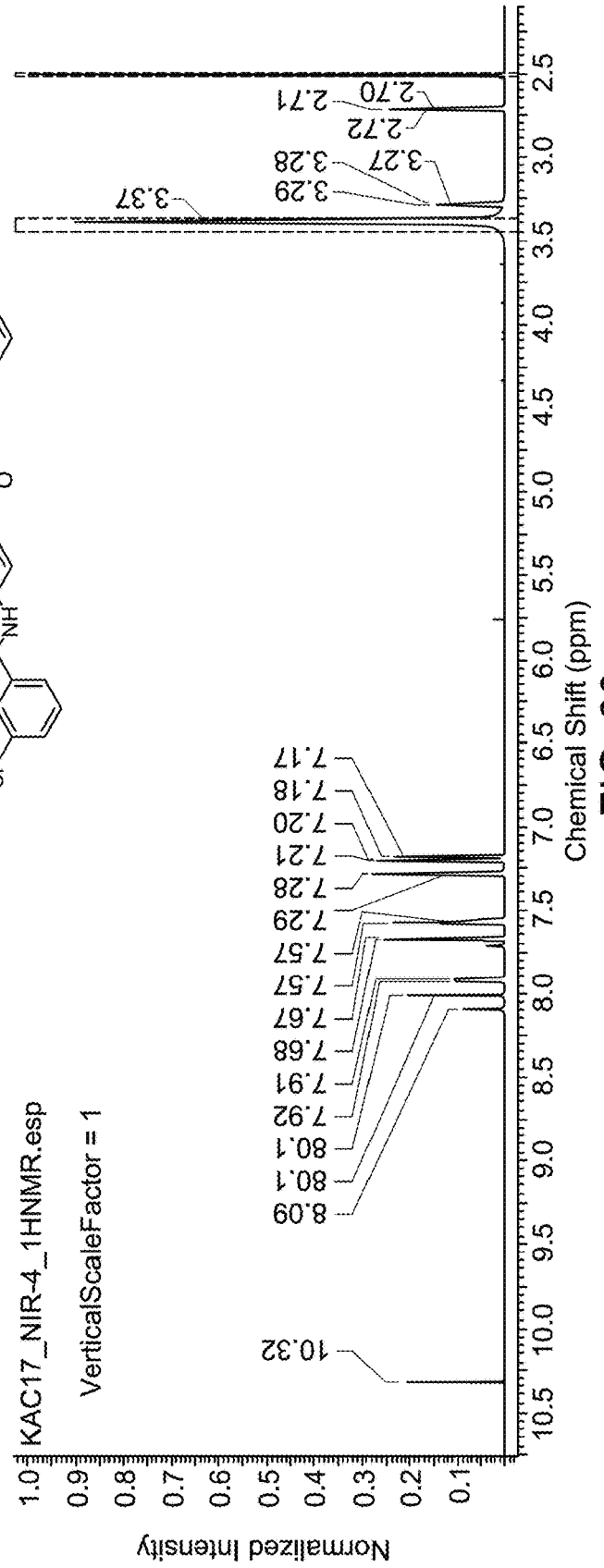
FIG. 30 is a $^1$H NMR spectrum of compound KAC-17 in DMSO-d$_6$.
Figure 31:
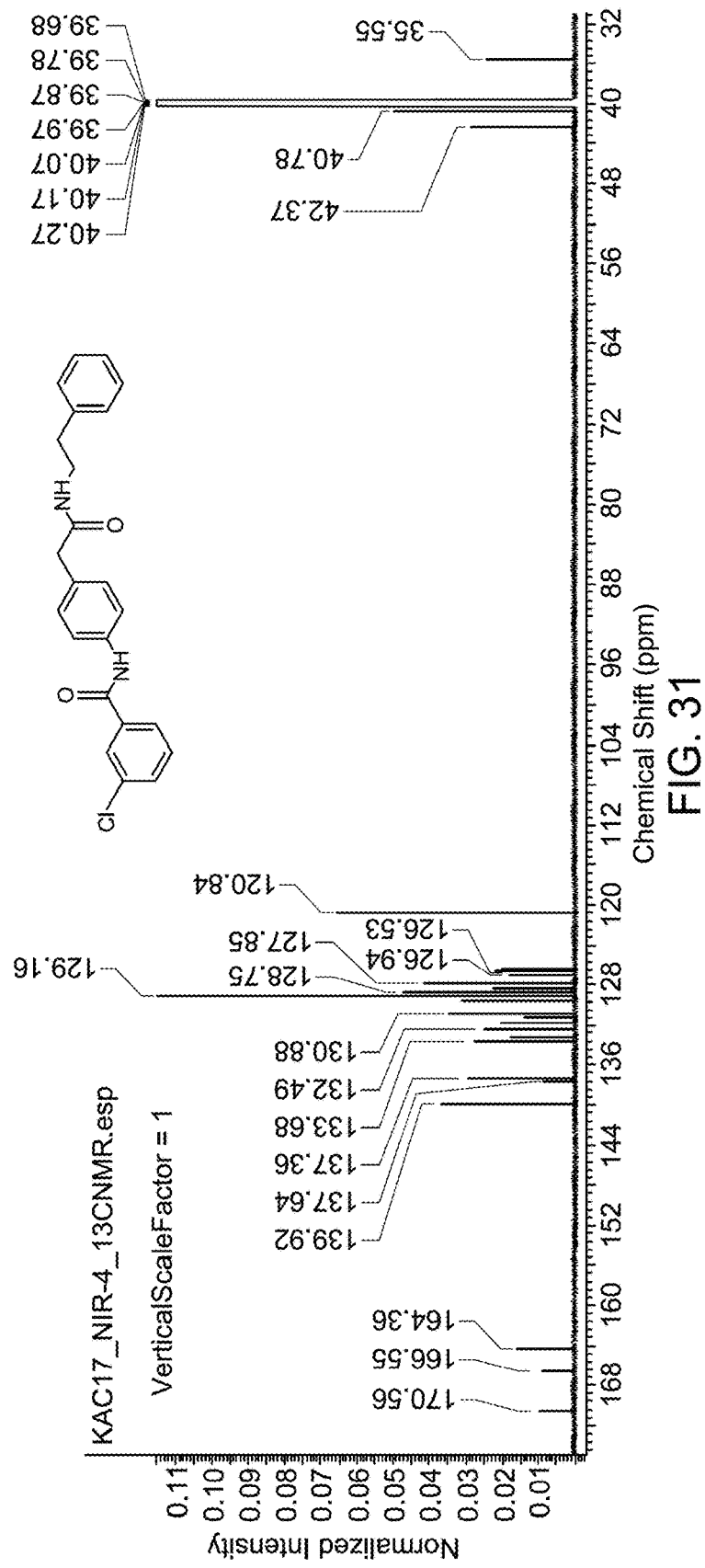
FIG. 31 is a $^{13}$C NMR spectrum of compound KAC-17 in DMSO-d$_6$.
Figure 32:
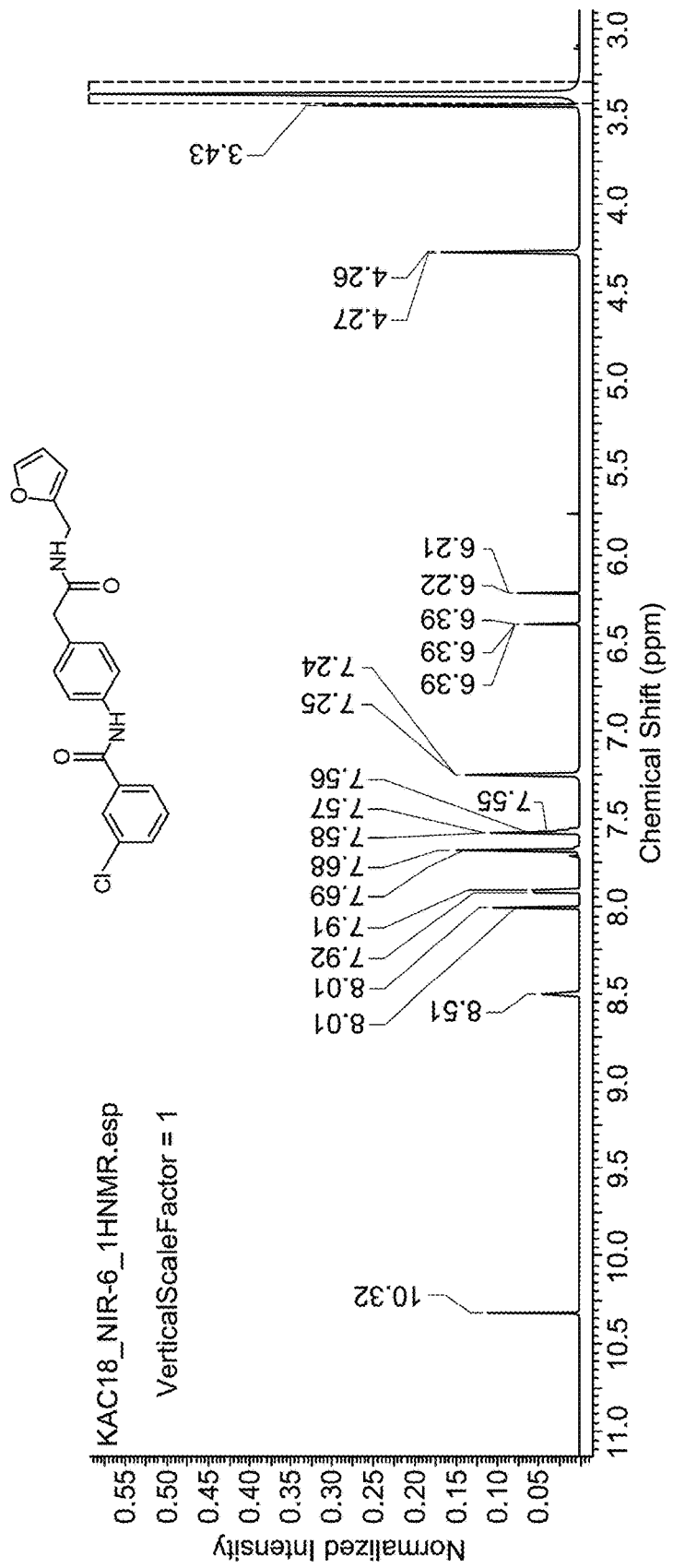
FIG. 32 is a $^1$H NMR spectrum of compound KAC-18 in DMSO-d$_6$.
Figure 33:
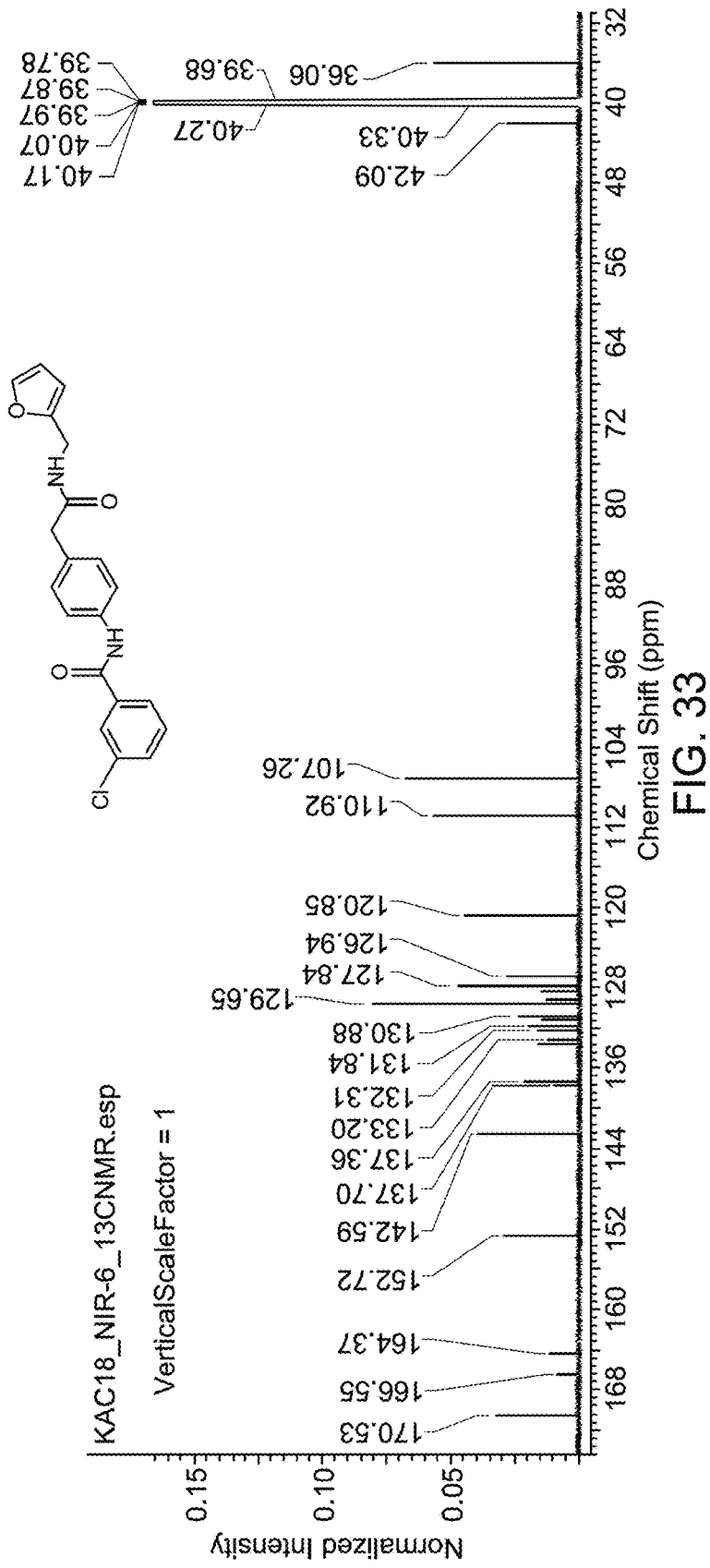
FIG. 33 is a $^{13}$C NMR spectrum of compound KAC-18 in DMSO-d$_6$.
Figure 34:
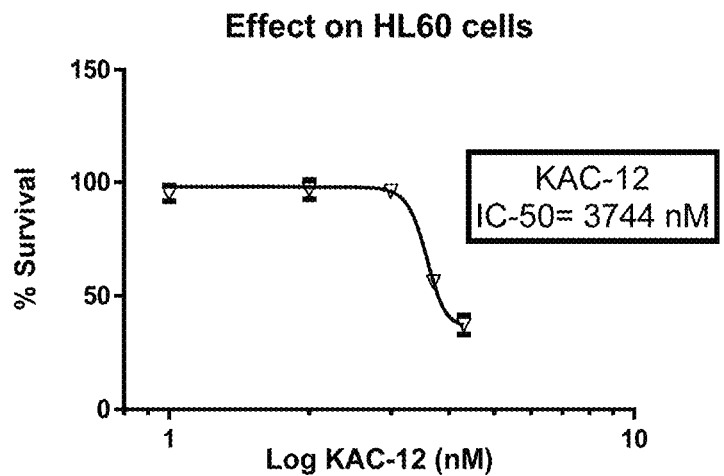
FIG. 34 shows the cytotoxicity of compound KAC-12 against H60 leukemia cell line.
Figure 35A:
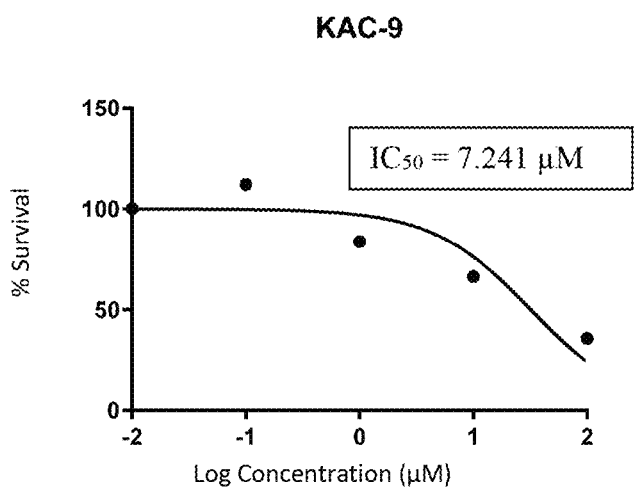
FIG. 35A shows the cytotoxicity of compound KAC-09 against N87 stomach cancer cells.
Figure 35B:
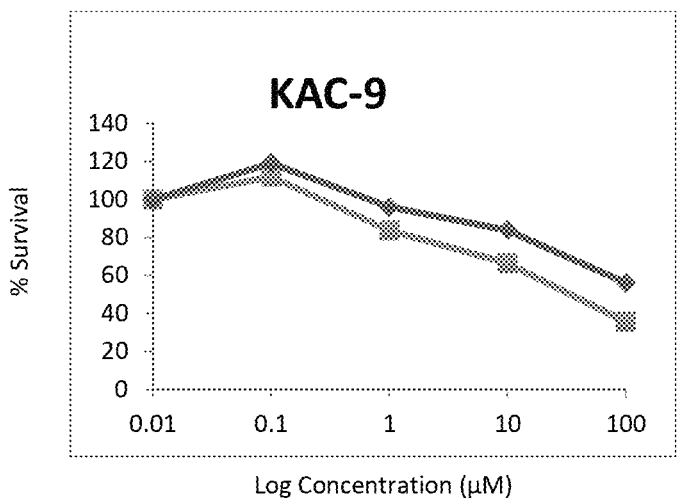
FIG. 35B shows the reproducibility of the cytotoxicity tests of compound KAC-09 against N87 stomach cancer cells.
Figure 36A:
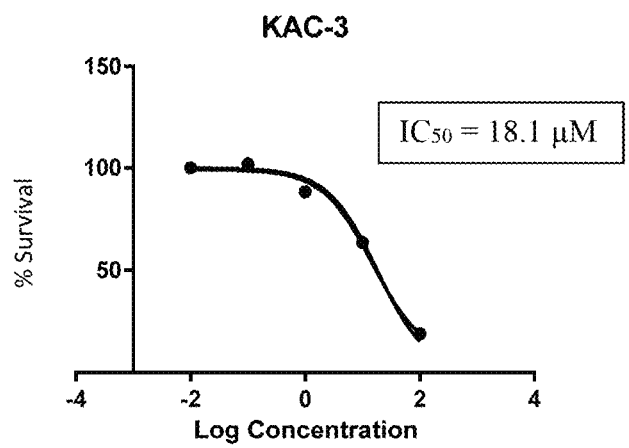
FIG. 36A shows the cytotoxicity of compound KAC-03 against N87 stomach cancer cells.
Figure 36B:
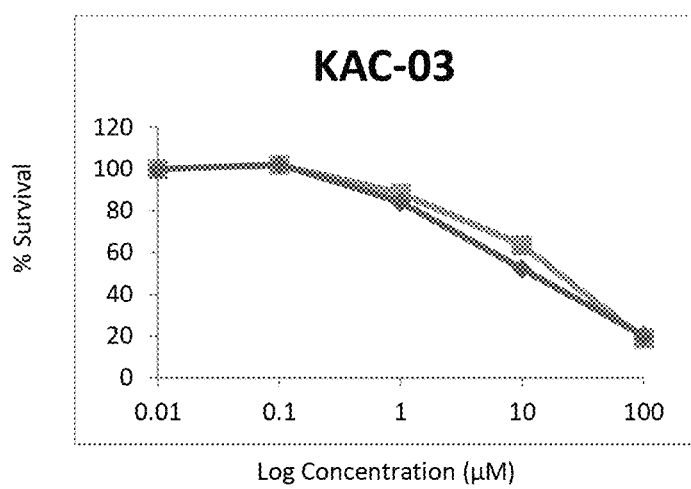
FIG. 36B shows the reproducibility of the cytotoxicity tests of compound KAC-03 against N87 stomach cancer cells.
Figure 37:
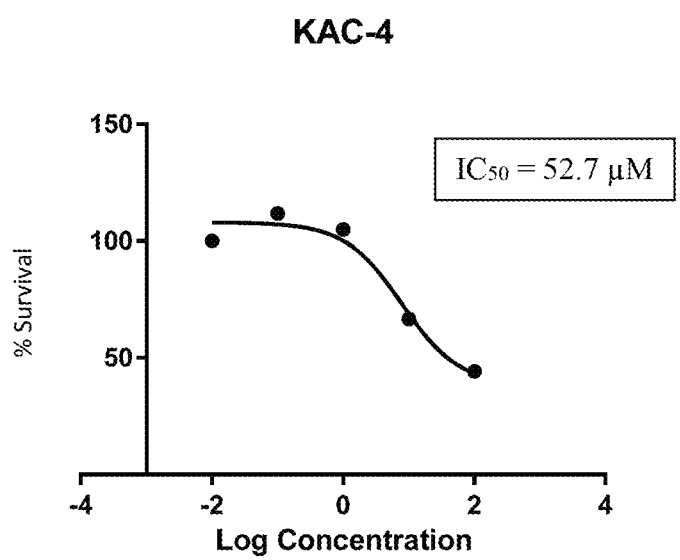
FIG. 37 shows the cytotoxicity of compound KAC-04 against N87 stomach cancer cells.
Figure 38:
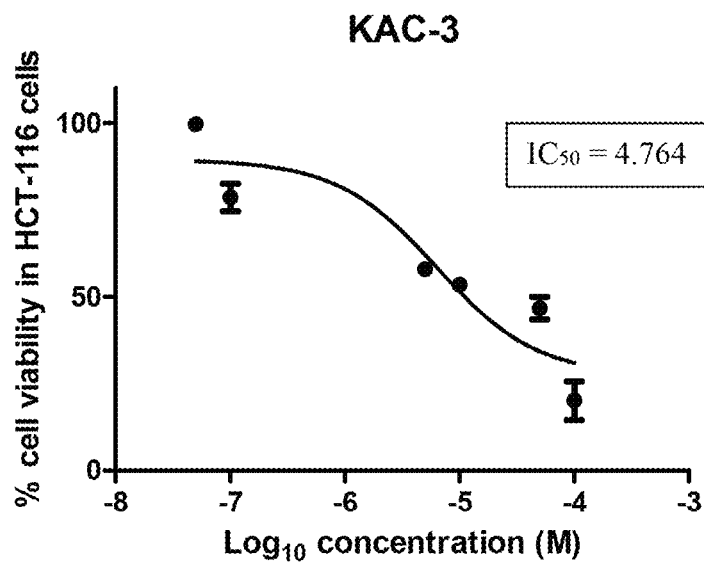
FIG. 38 shows the cytotoxicity of compound KAC-03 against HCT116 colon cancer cell line.
Figure 39:
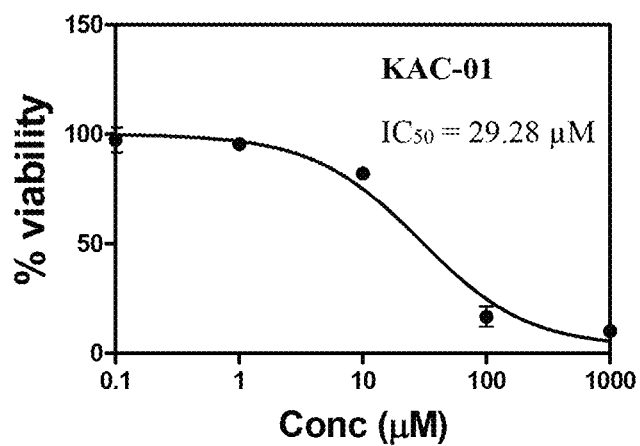
FIG. 39 shows the cytotoxicity of compound KAC-01 against MCF7 breast cancer cell line.
Figure 40:
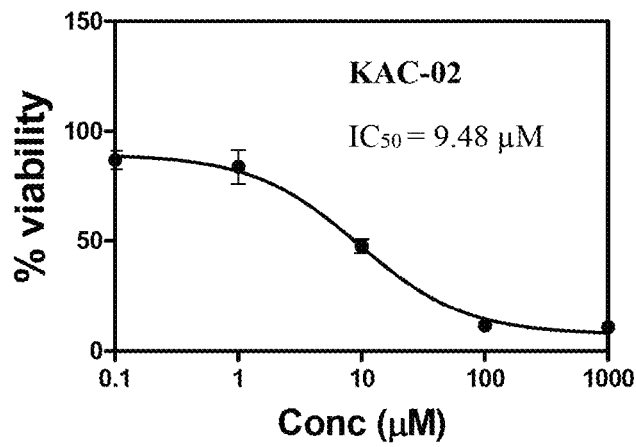
FIG. 40 shows the cytotoxicity of compound KAC-02 against MCF7 breast cancer cell line.
Figure 41:
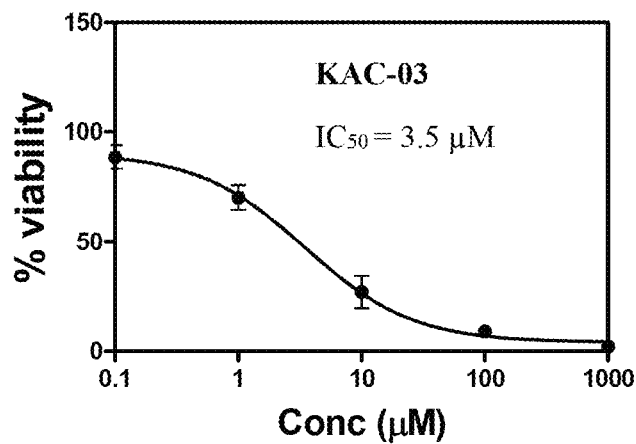
FIG. 41 shows the cytotoxicity of compound KAC-03 against MCF7 breast cancer cell line.

In general, G2/M cell cycle arrest is strongly associated with inhibition of tubulin polymerization. The effect of KX-01 analogue, KAC-3, was investigated with colon cancer HCT-116 cells by flow cytometry at two concentrations (5 µM and 10 µM) for 24 and 48 hours. As shown in FIGS. 9 and 10, it was clearly demonstrated that KAC-3 caused a significant G2/M arrest in a time- and concentration-dependent manner consistent with the behavior of the tubulin targeting agents. The percentage of cells in G2/M phase after 24 h was 13.3% and 41.7% at concentrations of 5 µM and 10 respectively compared to the control (9.0%) (see FIG. 9). Moreover, there was an increase in the number of cells in G2/M phase after 48 h with 30.7 and 32.8% at concentrations of 5 µM and 10 µM, respectively with a concomitant decrease of cells in GO/G1 phase (FIG. 10). After 48 h, there was an increase of apoptosis as indicated by the population in the sub-G1 phase with 8.7 and 11.6% at concentrations of 5 µM and 10 µM, respectively compared to the control (0.9%). The cell cycle analysis results for KAC-3 are typical for tubulin targeting agents, which characteristically cause G2/M blockade followed by apoptosis [Perez, E. A., Microtubule inhibitors: Differentiating tubulin-inhibiting agents based on mechanisms of action, clinical activity, and resistance. *Molecular cancer therapeutics* 2009, 8 (8), 2086-2095]. These finding are in agreement from the novel dual inhibitor of Src and tubulin KX-01 that induced significant G2M phase arrest in MDA-MB-231 and BT-549 and MDA-MB-468 cells [Kim, S.; Min, A.; Lee, K.-H.; Yang, Y.; Kim, T.-Y.; Lim, J. M.; Park, S. J.; Nam, H.-J.; Kim, J. E.; Song, S.-H.; Han, S.-W.; Oh, D.-Y.; Kim, J. H.; Kim, T.-Y.; Hangauer, D.; Lau, J. Y.-N.; Im, K.; Lee, D. S.; Bang, Y.-J.; Im, S.-A., Antitumor Effect of KX-01 through Inhibiting Src Family Kinases and Mitosis. *Cancer research and treatment: official journal of Korean Cancer Association* 2017, 49 (3), 643-655; and Anbalagan, M.; Carrier, L.; Glodowski, S.; Hangauer, D.; Shan, B.; Rowan, B. G., KX-01, a novel Src kinase inhibitor directed toward the peptide substrate site, synergizes with tamoxifen in estrogen receptor a positive breast cancer. *Breast cancer research and treatment* 2012, 132 (2), 391-409]. Paclitaxel and imatinib (both positive controls at 1 µM) have shown a gradual increase in apoptosis of 7.7% (FIG. 11) and 6.4% (FIG. 12), respectively at 48 h with no significant difference in the other cell cycle phases as G2/M phase or GO/G1 arrest [Lv, C.; Qu, H.; Zhu, W.; Xu, K.; Xu, A.; Jia, B.; Qing, Y.; Li, H.; Wei, H. J.; Zhao, H. Y., Low-Dose Paclitaxel Inhibits Tumor Cell Growth by Regulating Glutaminolysis in Colorectal Carcinoma Cells. *Frontiers in pharmacology* 2017, 8, 244].

Example 33

New derivatives of 4-(acylamino)-N-benzylphenylacetamide as a pharmacophore for developing novel anticancer agents are presented herein using rational design (Scaffold Hopping) (see FIG. 1). The compounds showed cytotoxic activities against a variety of cancer cell lines such as N87 (Stomach cancer), HCT116 (Colon cancer), and HL60 (Leukemia).

The disclosure introduces new chemical compounds to inhibit cancer cell growth which can be further developed for clinical applications in the treatment of several types of solid and liquid tumors. These compounds affect cell division at the mitosis stage and also promote apoptotic cell death. Therefore, it is likely that the compounds function dually via inhibitions of both Src kinase and tubulin.

The invention claimed is:

1. A pharmaceutical composition having an antiproliferative effect on leukemia cells, stomach cancer cells, breast cancer cells and/or colon cancer cells, comprising:

at least one compound selected from the group consisting of

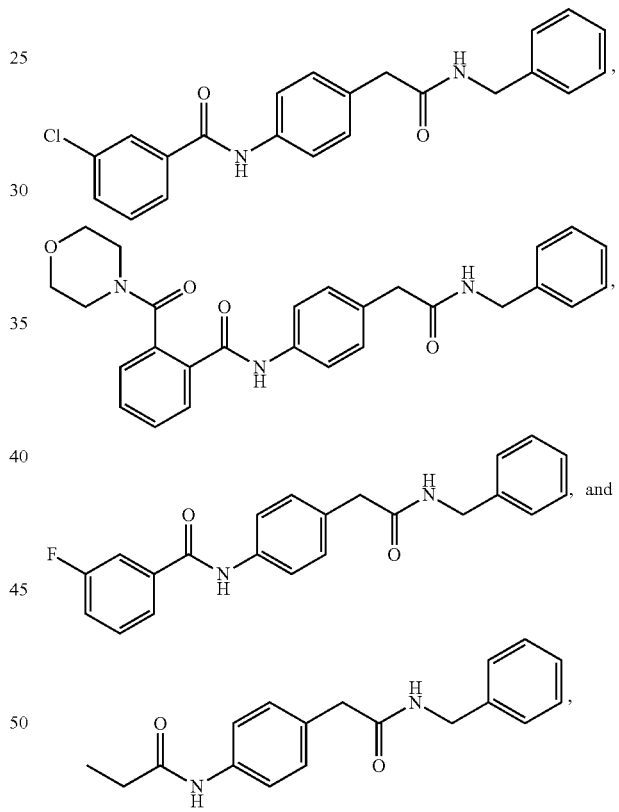

and a pharmaceutically acceptable carrier and/or excipient.

2. The pharmaceutical composition of claim 1, wherein the pharmaceutically acceptable carrier and/or excipient is at least one selected from the group consisting of a buffer, an inorganic salt, a fatty acid, a vegetable oil, a synthetic fatty ester, a surfactant, and a polymer.

3. The pharmaceutical composition of claim 1, which comprises 0.1-90 wt % of the compound relative to a total weight of the pharmaceutical composition.

* * * * *